(12) United States Patent
Lundemose et al.

(10) Patent No.: US 10,143,737 B2
(45) Date of Patent: Dec. 4, 2018

(54) METHOD FOR THE VACCINATION AGAINST HIV

(71) Applicant: Bionor Immuno AS, Skien (NO)

(72) Inventors: Anker Lundemose, Oslo (NO); Mats Ökvist, Oslo (NO); Arnt Ove Hovden, Oslo (NO); Maja Sommerfelt Grønvold, Oslo (NO)

(73) Assignee: BIONOR PHARMA ASA, Oslo (NO)

( * ) Notice: Subject to any disclaimer, the term of this patent is extended or adjusted under 35 U.S.C. 154(b) by 0 days.

(21) Appl. No.: 15/114,298

(22) PCT Filed: Jan. 27, 2015

(86) PCT No.: PCT/EP2015/051628
§ 371 (c)(1),
(2) Date: Jul. 26, 2016

(87) PCT Pub. No.: WO2015/110666
PCT Pub. Date: Jul. 30, 2015

(65) Prior Publication Data
US 2017/0000876 A1    Jan. 5, 2017

(30) Foreign Application Priority Data

Jan. 27, 2014 (EP) .................................... 14152659

(51) Int. Cl.
| | | |
|---|---|---|
| *C07K 16/00* | (2006.01) | |
| *C07K 14/47* | (2006.01) | |
| *C07K 14/435* | (2006.01) | |
| *C12N 5/00* | (2006.01) | |
| *G01N 33/53* | (2006.01) | |
| *A61K 39/12* | (2006.01) | |
| *G01N 33/569* | (2006.01) | |
| *A61K 45/06* | (2006.01) | |
| *C12N 7/00* | (2006.01) | |
| *A61K 39/00* | (2006.01) | |

(52) U.S. Cl.
CPC .............. *A61K 39/12* (2013.01); *A61K 45/06* (2013.01); *C12N 7/00* (2013.01); *G01N 33/56988* (2013.01); *A61K 2039/55522* (2013.01); *C12N 2740/16034* (2013.01); *G01N 2333/162* (2013.01); *G01N 2469/20* (2013.01)

(58) Field of Classification Search
CPC .... C07K 14/47; C07K 14/4702; A61K 38/00; A61K 48/00; C07H 21/04
See application file for complete search history.

(56) References Cited

FOREIGN PATENT DOCUMENTS

| | | |
|---|---|---|
| WO | WO 00/52040 A1 | 9/2000 |
| WO | WO 2011/000962 A2 | 1/2011 |
| WO | WO 2011/000962 A3 | 1/2011 |
| WO | WO 2011/000962 A9 | 1/2011 |
| WO | WO 2012/0782088 A1 | 6/2012 |
| WO | WO 2012/092934 A1 | 7/2012 |
| WO | WO 2013/182660 A1 | 12/2013 |
| WO | WO 2013/182662 A1 | 12/2013 |

OTHER PUBLICATIONS

Åsjö, B., et al., Phase I Trial of a Therapeutic HIV Type 1 Vaccine, Vacc-4x, in HIV Type 1-Infected Individuals with or without Antiretroviral Therapy, *AIDS Research and Human Retroviruses*, 2002, vol. 18(18), pp. 1357-1365.
Ellefsen-Lavoie, K., et al., "Quality of T-cell responses versus reduction in viral load: results from an exploratory phase II clinical study of VACC-4x, a therapeutic HIV vaccine," *Retrovirology*, 2012, vol. 9(Suppl 2), pp. 066.
Sommerfelt, MA, et al., "Vacc-4x and Vacc-C5: Two peptide-based therapeutic HIV vaccine candidates," *Journal of Acquired Immunodeficiency Syndromes*, 2013, vol. 62(Suppl 1), B109—abstract.

*Primary Examiner* — Barry A Chestnut
(74) *Attorney, Agent, or Firm* — Womble Bond Dickinson (US) LLP

(57) ABSTRACT

The present invention relates to novel compositions of active agents and methods for the treatment of HIV infection and AIDS. In particular, the present invention relates to novel methods to select HIV infected patients with improved responses to HIV-specific vaccine peptides.

22 Claims, 1 Drawing Sheet
Specification includes a Sequence Listing.

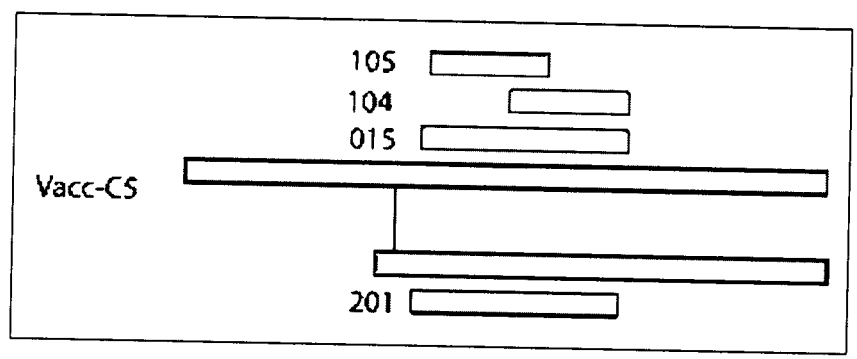

METHOD FOR THE VACCINATION AGAINST HIV

CROSS-REFERENCE TO RELATED APPLICATIONS

This application is a national stage filing under 35 U.S.C. 371 of PCT/EP2015/051628, filed Jan. 27, 2015, which International Application was published by the International Bureau in English on Jul. 30, 2015, and application claims priority from European Application No. 14152659.0, filed Jan. 27, 2014.

FIELD OF THE INVENTION

The present invention relates to methods for treating reducing and/or delaying pathological effects of human immunodeficiency virus I (HIV) in a human infected with HIV or for reducing the risk of developing acquired immunodeficiency syndrome (AIDS) in a human.

BACKGROUND OF THE INVENTION

HIV-1 infection is today perceived as an incurable chronic viral infection in which lifelong combination antiretroviral therapy (cART) is needed to avoid disease (Egger, Hirschel et al. 1997, Palella, Delaney et al. 1998). Very early during acute HIV infection a latent reservoir is established and despite effective cART, HIV-1 persists in latently infected cells (Dai, Agosto et al. 2009, Carter, Onafuwa-Nuga et al. 2010, Wightman, Solomon et al. 2010). Upon treatment interruption, the virus quickly replicates, and viremia rebounds to pre-treatment levels. In the inactive, resting state latently infected cells are unrecognizable to the immune system and unresponsive to antiretroviral drugs (Chun, Stuyver et al. 1997, Finzi, Hermankova et al. 1997). The size of the reservoir likely varies between individuals and may be influenced by a number of different factors such as host immune constitution, time from diagnosis to initiation, level of persistent immune activation, antiretroviral treatment regimens used and individual response to treatment. Earlier studies employing viral outgrowth assays indicated that the number of latent CD4 T cells harboring replication-competent virus was approximately 1 per 106 cells.

A broad range of bioanalytical assays have been used in the attempt to quantify the reservoir but it is currently unclear which assay(s) should be used to monitor HIV-1 reservoirs in clinical studies of eradication strategies (Eriksson, Graf et al. 2013). Upon activation, resting T cells carrying replication competent integrated proviral DNA are capable of resuming HIV transcription (Chun, Finzi et al. 1995, Chun, Carruth et al. 1997, Eriksson, Graf et al. 2013). One of the proposed ways of curing HIV-1 is to activate and kill latently infected cells in the presence of antiretroviral therapy (Deeks 2012). Epigenetic modulation of the molecular mechanisms that block transcription of integrated HIV DNA can reactivate HIV-1 expression in resting infected memory CD4 T cells and disrupt latency (Rasmussen, Schmeltz Sogaard et al. 2013, Rasmussen, Tolstrup et al. 2013). Histone deacetylase inhibitors (HDACi) turn on genes by promoting acetylation of lysine residues on histones (Van Lint, Emiliani et al. 1996, Tyagi, Pearson et al. 2010). This induces chromatin relaxation and transcriptional activation. The HDACi romidepsin (Celgene) potently activates HIV-1 expression in latently infected cell lines and primary T cells (Geleziunas 2013).

Vacc-4x is a peptide-based HIV-1 therapeutic vaccine that aims to improve immune responses to p24Gag since this has been associated with slower disease progression and improved virus control (Kiepiela 2007; Zuniga 2006). The primary objective of Vacc-4x immunization is to strengthen the immune system's response to HIV p24. The enhanced immune response to HIV-1 following immunization with Vacc-4x could improve the host immune system as part of an HIV functional cure treatment strategy.

In one of the largest randomized, placebo controlled HIV therapeutic vaccine trials conducted to date (study CT-BI/Vacc-4x/2007/1), Vacc-4x and rhuGM-CSF (Leukine®) as adjuvant showed a significant reduction in viral load (VL) set point in the Vacc-4x group as compared to placebo and a significant reduction in VL set point from historic preART values, despite higher preART values being present in the Vacc-4x group as compared to placebo. Additionally Vacc-4x was shown to be immunogenic, inducing proliferative responses in both CD4 and CD8 T-cell.

New HIV p24 peptides are described in WO91/13360, wherein the peptides are used in a method of discriminating between a false and true diagnosed HIV-positive serum sample.

Johnson R. P., et al., The Journal of Immunology, Vol. 147, p. 1512-1521, No. 5, Sep. 1, 1991 describe an analysis of the fine specificity of gag-specific CTL-responses in three HIV-1 seropositive individuals, the gag-specific CTL-responses were found to be mediated by CD3+CD8+ lymphocytes which are HLA class I restricted.

EP-A-0 356 007 discloses antigenic determinants, in particular it relates to synthetic polypeptide sequences which are related to proteins present in the HIV-1 and which can be used as a basis for a potential vaccine against AIDS.

Rosenberg E. S. et al., Science, Vol. 278, 21 Nov. 1997, p. 1447-1450 describe that virus specific CD4+ T helper lymphocytes are critical to the maintenance of effective immunity in a number of chronic viral infections, but are characteristically undetectable in chronic human immunodeficiency virus-type 1 (HIV-1) infection. HIV-1-specific proliferative responses to p24 were inversely related to viral load. They conclude that the HIV-1-specific helper cells are likely to be important in immunotherapeutic interventions and vaccine development.

EP 0 230 222, EP 0 270 114, DE 37 11 016 and GB 2 188 639 all in the name of F. Hoffmann-La Roche & Co. Aktiengesellschaft concern recombinant expression and purification of an HTLVIII Gag/Env gene protein or fusion-proteins. The proteins consisting of native sequences can be purified to homogeneity and used as a basis for diagnostic tests for detection of antibodies against viruses associated with AIDS. The gag/env protein may also be formulated for use as a vaccine for protection against AIDS through prophylactic immunization.

International Patent Application WO00/52040 discloses methods for treating HIV infections by administering e.g. HIV specific peptides based on conserved regions of HIV gag p24.

There is a need to provide improved methods for the treatment of HIV infections and AIDS.

OBJECT OF THE INVENTION

It is an object of embodiments of the invention to provide a more efficient method for reducing and/or delaying pathological effects of human immunodeficiency virus I (HIV) in a human infected with HIV or for reducing the risk of developing acquired immunodeficiency syndrome (AIDS)

in a human, wherein the human potential subject for treatment is tested for antibodies against HIV envelope glycoprotein gp120 and/or gp41 to identify subjects having most benefit of a treatment with a composition, that elicit a cell-mediated immune response in a subject, such as a composition comprising one or more peptide, such as a HIV-specific peptide.

SUMMARY OF THE INVENTION

It has been found that a specific subgroup of human patients infected with HIV has an improved response to an HIV vaccine. In particular, it was found that human patients infected with HIV and which patients has an amount of antibodies against a defined region of HIV envelope glycoprotein gp120 and/or gp41 above background level of uninfected humans, such as above 0.5 μg/ml, such as above 0.6 μg/ml, such as above 0.7 μg/ml, such as above 0.8 μg/ml, such as above 0.9 μg/ml, such as above 1.0 μg/ml, such as above 1.5 μg/ml, such as above 2 μg/ml, such as above 3 μg/ml, such as above 4 μg/ml, such as above 5 μg/ml, such as above 6 μg/ml, such as above 7 μg/ml, such as above 8 μg/ml, such as above 9 μg/ml, such as above 10 μg/ml of measured antibodies corresponding to an amount of antibodies against Vacc-C5 in serum as measured by an ELISA assay as described in example 33, these patients has an improved response to a treatment with one or more peptide(s) to stimulate a cell-mediated immune response and/or a compound that stimulate a humoral response in said human.

It is to be understood that the effect seen in this specific subgroup of human patients infected with HIV is increased not just because these patients respond better to the vaccination or are the best patients suited in general for vaccinations. This is very specific to the vaccination regime according to the present invention.

So, in a first aspect of the present invention is provided a method for reducing and/or delaying pathological effects of human immunodeficiency virus I (HIV) or for reducing the risk of developing acquired immunodeficiency syndrome (AIDS) in a human infected with HIV, the method comprising the steps of:

a) measuring in a biological sample, such as serum or plasma, from a human infected with HIV the amount of antibodies against one or more epitope of HIV envelope glycoproteins gp120 and/or gp41 in a suitable assay;

b) selecting a subgroup of humans from a), wherein the amount of said measured antibodies corresponds to an amount of above background level, such as above 1 μg/ml of antibodies against Vacc-C5 in serum as measured by an ELISA assay as described in example 33;

c) treating said humans infected with HIV selected under b) with one or more peptide(s) to stimulate a cell-mediated immune response and/or a compound that stimulate a humoral response in said human.

Said measured antibodies corresponding to an amount above background in step b) is understood to mean above 0.5 μg/ml, such as above 0.6 μg/ml, such as above 0.7 μg/ml, such as above 0.8 μg/ml, such as above 0.9 μg/ml, such as above 1.0 μg/ml, such as above 1.5 μg/ml, such as above 2 μg/ml, such as above 3 μg/ml, such as above 4 μg/ml, such as above 5 μg/ml, such as above 6 μg/ml, such as above 7 μg/ml, such as above 8 μg/ml, such as above 9 μg/ml, such as above 10 μg/ml of measured antibodies corresponding to an amount of antibodies against Vacc-C5 in serum as measured by an ELISA assay as described in example 33.

In a second aspect of the present invention is provided a kit for reducing and/or delaying pathological effects of human immunodeficiency virus I (HIV) or for reducing the risk of developing acquired immunodeficiency syndrome (AIDS) in a human infected with HIV, which kit comprises a) a test assay for measuring in a biological sample, such as serum or plasma, of said human infected with HIV the amount of antibodies against HIV envelope glycoprotein gp120 and/or gp41; and b) one or more peptide to stimulate a cell-mediated immune response and/or a compound that stimulate a humoral response in said human, optionally c) one or more immunomodulatory compound and/or a reservoir purging agent, such as any one described herein.

In a third aspect of the present invention there is provided an effective amount of one or more peptide to stimulate a cell-mediated immune response and/or a compound that stimulate a humoral response for use in method for reducing and/or delaying pathological effects of human immunodeficiency virus I (HIV) or for reducing the risk of developing acquired immunodeficiency syndrome (AIDS) in a human infected with HIV, the method comprising the steps of:

a) measuring in a biological sample, such as serum or plasma, of said human infected with HIV the amount of antibodies against HIV envelope glycoprotein gp120 and/or gp41 in a suitable assay;

b) selecting humans infected with HIV, wherein the amount of said measured antibodies corresponds to an amount of above background level of uninfected humans, such as above 1 μg/ml of antibodies against Vacc-C5 in serum as measured by an ELISA assay as described in example 33;

c) treating said humans infected with HIV selected under b) with one or more peptide to stimulate a cell-mediated immune response and/or a compound that stimulate a humoral response in said human.

In a fourth aspect of the present invention is provided a method for reducing and/or delaying pathological effects of human immunodeficiency virus I (HIV) or for reducing the risk of developing acquired immunodeficiency syndrome (AIDS) in a human infected with HIV, the method comprising the steps of:

a) measuring in a biological sample, such as serum or plasma, of said human infected with HIV the amount of antibodies against HIV envelope glycoprotein gp120 and/or gp41 in a suitable assay;

b) selecting humans infected with HIV, wherein said amount of antibodies is above background level in uninfected humans and below 1 μg/ml of antibodies against Vacc-C5 in serum as measured by an ELISA assay as described in example 33;

c) treating said humans infected with HIV selected under b) with a compound that stimulate a humoral response in said human;

d) optionally having a maturation period, such as a period of up to 4 weeks;

e) optionally repeating the measurement in a) and selecting humans infected with HIV, wherein the amount of said measured antibodies corresponds to an amount of above background level of uninfected humans, such as above 1 μg/ml of antibodies against Vacc-C5 in serum as measured by an ELISA assay as described in example 33;

f) treating said humans infected with HIV selected under b) or e) with one or more peptide to stimulate a cell-mediated immune response and/or a compound that stimulate a humoral response in said human.

In some embodiments, the method comprises the steps of:

a) measuring in a biological sample, such as serum or plasma, of said human infected with HIV the amount of antibodies against HIV envelope glycoprotein gp120 and/or gp41 in a suitable assay;

b) selecting humans infected with HIV, wherein said amount of antibodies is above background level in uninfected humans and below 1 µg/ml of antibodies against Vacc-C5 in serum as measured by an ELISA assay as described in example 33;

c) treating said humans infected with HIV selected under b) with a compound that stimulate a humoral response in said human;

d) optionally having a maturation period, such as a period of up to 4 weeks;

e) treating said humans infected with HIV selected under b) with one or more peptide to stimulate a cell-mediated immune response and/or a compound that stimulate a humoral response in said human.

In some embodiments, the method comprises the steps of fected humans and below 1 µg/ml of antibodies against Vacc-C5 in serum as measured by an ELISA assay as described in example 33;

c) treating said humans infected with HIV selected under b) with a compound that stimulate a humoral response in said human;

d) having a maturation period, such as a period of up to 4 weeks;

e) repeating the measurement in a) and selecting humans infected with HIV, wherein the amount of said measured antibodies corresponds to an amount of above background level of uninfected humans, such as above 1 µg/ml of antibodies against Vacc-C5 in serum as measured by an ELISA assay as described in example 33;

f) treating said humans infected with HIV selected under b) or e) with one or more peptide to stimulate a cell-mediated immune response and/or a compound that stimulate a humoral response in said human.

BRIEF DESCRIPTION OF THE DRAWINGS

FIG. 1 shows the location of peptides within the Vacc C5 antigen.

DETAILED DISCLOSURE OF THE INVENTION

The present invention is based on the finding that human patients, infected with HIV and which patients has an amount of antibodies against a defined region of HIV envelope glycoprotein gp120 and/or gp41 above 2 µg/ml, has an improved response to a HIV vaccine treatment with one or more peptide to stimulate a cell-mediated immune response and/or a compound that stimulate a humoral response in said human.

Definitions

The term "biological sample" refers to any body fluid or subfraction thereof that may be obtained from the body of a mammal. Included within this definition are cerebrospinal fluids, blood, such as blood from the circulatory system or from the umbilical cord, serum, lymph fluid, plasma, pleura exudates, peritoneal exudates, bone marrow exudates, extracellular fluids, fluids from the joints, amniotic fluids.

In some embodiments the body fluid is blood, such as peripheral blood or any component derived from blood, such as the serum or plasma fraction.

The phrase "the amount of antibodies against one or more epitope of HIV envelope glycoproteins gp120 and/or gp41 in a suitable assay" as used herein refers to the amount of antibodies specifically binding one or more epitopes present in HIV envelope glycoproteins gp120 and/or gp41, such as those present in Vacc-C5 as defined herein, which may be measured in the assay described in example 33. It is to be understood that Vacc-C5 is a dimeric peptide consisting of peptides derived from both gp120 and gp41 and accordingly comprising epitopes derived therefrom. The specific amounts may vary somewhat depending on the specific assay used. It is also to be understood that a humoral immune response to one or more epitope of HIV envelope glycoproteins gp120 and/or gp41 may be measured with other antigens derived from gp120 and/or gp41 and that Vacc-C5 is just one measure for antibodies against one or more epitope of HIV envelope glycoproteins gp120 and/or gp41. The threshold values are set corresponding to values obtained when using antibodies against Vacc-C5 in serum as a standard and when using the specific assay described herein. This does not exclude that other assays may be used or that other specific epitopes derived from HIV envelope glycoproteins gp120 and/or gp41 may be used to detect an elevated level of antibodies against one or more epitope of HIV envelope glycoproteins gp120 and/or gp41.

When terms such as "one", "a" or "an" are used in this disclosure they mean "at least one", or "one or more" unless otherwise indicated. Further, the term "comprising" is intended to mean "including" and thus allows for the presence of other constituents, features, conditions, or steps than those explicitly recited.

"HIV" unless otherwise indicated generally denotes human immunodeficiency virus I.

"HIV disease" is composed of several stages including the acute HIV infection which often manifests itself as a flu-like infection and the early and medium stage symptomatic disease, which has several non-characteristic symptoms such as skin rashes, fatigue, night sweats, slight weight loss, mouth ulcers, and fungal skin and nail infections. Most HIV infected will experience mild symptoms such as these before developing more serious illnesses. It is generally believed that it takes five to seven years for the first mild symptoms to appear. As HIV disease progresses, some individuals may become quite ill even if they have not yet been diagnosed with AIDS (see below), the late stage of HIV disease. Typical problems include chronic oral or vaginal thrush (a fungal rash or spots), recurrent herpes blisters on the mouth (cold sores) or genitals, ongoing fevers, persistent diarrhea, and significant weight loss. "AIDS" is the late stage HIV disease and is a condition which progressively reduces the effectiveness of the immune system and leaves individuals susceptible to opportunistic infections and tumors.

When using the term "gp120" herein is meant the ≈120 kDa N-terminal glycoprotein enzymatic cleavage product of gp160, which in turn is the sole expression product of the HIV env gene. gp120 forms the "spikes" on infective HIV virions and is non-covalently bound to gp41.

"gp41" denotes the ≈41 kDa glycoprotein C-terminal enzymatic cleavage product of gp160. gp41 is located in the membrane of HIV infected cells or virions. gp41 has an N-terminal transmembrane domain which binds non-covalently to gp120. This transmembrane domain is termed "the transmembrane domain of gp41" or "tm-gp41" herein. The term includes within its scope naturally occurring mutated versions of the sequence as e.g. those set forth in Formula III.

"C5" or the "C5 domain" denotes the 13 C-terminal amino acid residues of gp120.

"C2" or the "C2 domain" denotes a conserved region in gp120. Regions in C2 form an antiparallel β-sheet with C5 in the inner proximal domain of gp12.

"Reducing and/or delaying pathological effect of HIV" is in the present context meant to denote that use of the methods of the invention provides for a statistically significant reduction and/or delay in morbidity seen in individual infected with HIV which are treated according to the present invention. That is, the time of onset of manifest disease symptoms characterizing AIDS is later compared to non-treated controls and/or the number of pathological manifestations is reduced to controls not receiving the treatment of the present invention.

The expression "association of the C5 domain of HIV gp120 with the transmembrane domain of gp41 and/or with the constant C2 domain of gp120" means that C5 can interact non-covalently with both or one of the tm-g41 and C2. The interaction with tm-gp41 is intermolecular, whereas the interaction with C2 is intramolecular.

An "agent capable of stabilising" association of the C5 domain of HIV gp120 with the transmembrane domain of gp41 and/or with the constant C2 domain of gp120 is a composition of matter which prevents or statistically reduces release of C5 from its intermolecular binding to gp41 and/or from its intramolecular binding to C2. Generally, such an agent is any substance of matter capable of exerting this effect, but important examples are antibodies, antibody fragments, and antibody analogues. However, also other molecules having proper binding affinity for a complex between C5 on the one hand and tm-gp41 and/or C2 on the other, is an agent according the present invention—the precise molecular format is less important than the binding characteristics, and it is according to the invention also possible that such an agent may be a receptor or a receptor analogue, but also small molecule stabilisers are capable of functioning as an agent of the present invention.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity, i.e. to function as an agent described above. Various techniques relevant to the production of antibodies are provided in, e.g., Harlow, et al., Antibodies: A Laboratory Manual, Cold Spring Harbor Laboratory Press, Cold Spring Harbor, N.Y., (1988).).

An "antibody fragment or antibody analogue" comprises a portion of a full-length antibody, preferably antigen-binding or variable regions thereof. Examples of antibody fragments/analogues include Fab, Fab', F(ab)$_2$, F(ab')$_2$, F(ab)$_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

The term "antibody derivative", as used herein, comprises a full-length antibody or a fragment of an antibody, preferably comprising at least antigen-binding or variable regions thereof, wherein one or more of the amino acids are chemically modified, e.g., by alkylation, PEGylation, acylation, ester formation or amide formation or the like, e.g., for linking the antibody to a second molecule. This includes, but is not limited to, PEGylated antibodies, cysteine-PEGylated antibodies, and variants thereof.

A "conjugate" as used herein comprises an agent to be used according to the invention such as an antibody derivative associated with or linked to a second agent, such as a cytotoxic agent, a detectable agent, etc. A conjugate may be constituted of covalently linked peptides (an example of a conjugate is a fusion peptide comprising two peptides linked via peptide bonds so that the conjugate in that case may be an expression product from a nucleic acid fragment), but a conjugate can also be a combination of peptides covalent linked via chemical conjugation (a traditional example is conjugation using glutaraldehyde). Another example of a more complex conjugation is the example where an agent or peptide multimer or other chemical substance of the present invention is linked to a carrier molecule, which in turn i coupled to other agents, peptide multimers or other chemical substances of the present invention (e.g. when such chemical substances are bound to a poly-lysine carrier (a lysine "tree")).

A "humanized" antibody is a human/non-human chimeric antibody that contains a minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992), WO 92/02190, US Patent Application 20060073137, and U.S. Pat. Nos. 6,750,325, 6,632,927, 6,639,055, 6,548,640, 6,407,213, 6,180,370, 6,054,297, 5,929,212, 5,895,205, 5,886,152, 5,877,293, 5,869,619, 5,821,337, 5,821,123, 5,770,196, 5,777,085, 5,766,886, 5,714,350, 5,693,762, 5,693,761, 5,530,101, 5,585,089, and 5,225,539.

An antibody having a "biological characteristic" of a reference antibody, is one that possesses one or more of the biological characteristics of that antibody that distinguish it from other antibodies that bind to the same antigen.

The term "peptide" is in the present context intended to mean both short peptides of from 2 to 10 amino acid residues, oligopeptides of from 11 to 100 amino acid residues, and polypeptides of more than 100 amino acid residues. When referring to amino acids in peptides, it is intended that the amino acids are L-amino acids, unless other information is provided. Amino acids are referred to by their standard three letter or one letter designations unless otherwise stated. Some unusual amino acids referred to herein includes homoarginine usually abbreviated by Har, norleucine usually abbreviated as Nle or Nl, N-ε-methylated Lys usually abbreviated Lys(Me), Citrulline usually abbreviated Cit or with the single letter "B", diaminopropionic acid usually abbreviated with Dpr and serinyl diaminopropionic acid usually abbreviated Dpr(Ser).

A "protein" is intended to denote a functional biomolecule comprising at least one peptide; when comprising at least two peptides, these may form complexes, be covalently linked, or may be non-covalently linked. The polypeptide(s) in a protein can be glycosylated and/or lipidated and/or comprise prosthetic groups.

A "peptide multimer" denotes a molecule which is constituted by at least two peptides in a non-natural configuration relative to each other. Examples are peptides from the same or from different proteins which are covalently linked via the side chains of at least one of their amino acids, or which are linked via their termini (e.g. via peptide bonds) but in a configuration which does not appear in nature. Typical examples of peptide multimers are detailed below.

A "variant" or "analogue" of a peptide refers to a peptide having an amino acid sequence that is substantially identical to a reference peptide, typically a native or "parent" polypeptide. The peptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). A particular form of conservative amino acid substitutions include those with amino acids, which are not among the normal 20 amino acids encoded by the genetic code. Since preferred embodiments of the present invention entail use of synthetic peptides, it is unproblematic to provide such "non-naturally occurring" amino acid residues in the peptides disclosed herein, and thereby it is possible to exchange the natural saturated carbon chains in the side chains of amino acid residues with shorter or longer saturated carbon chains—for instance, lysine may be substituted with an amino acid having an the side chain $—(CH_2)_nNH_3$, where n is different from 4, and arginine may be substituted with an amino acid having the side chain $—(CH_2)_nNHC(=NH_2)NH_2$, where n is different from 3, etc. Similarly, the acidic amino acids aspartic acid and glutamic acid may be substituted with amino acid residues having the side chains $—(CH_2)_nCOOH$, where n>2.

A "retro form" of a peptide is a form of a peptide where the order of the amino acids in N- to C-terminal direction has been inverted. For instance, the retro form of ALDFR is the peptide RFDLA.

The term "substantially identical" in the context of two amino acid sequences means that the sequences, when optimally aligned, such as by the programs GAP or BESTFIT using default gap weights, share at least about 50, at least about 60, at least about 70, at least about 80, at least about 90, at least about 95, at least about 98, or at least about 99 percent sequence identity. In one embodiment, residue positions that are not identical differ by conservative amino acid substitutions. Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA or ClustalW, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms, or when deducing the is the computer program BLAST, especially blastp, using default parameters. See, e.g., Altschul et al., 3. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, typically using default parameters.

The term "subsequence" in general means any consecutive stretch of at least 3 amino acids or, when relevant, of at least 3 nucleotides, derived directly from a naturally occurring amino acid sequence or nucleic acid sequence, respectively. However, when discussing peptide multimers of the present invention, the subsequence may be as short as 1 or 2 amino acids. This is because the inventive peptide multimers include amino acids from different peptide domains, where the amino acids together at least form a conformational epitope for an antibody. Hence, such a conformational epitope could be composed of 4 amino acids from C5, but only 1 or 2 from tm-gp41—the important point is here that this combined epitope from 2 domains is capable of being stabilised, i.e. that antibody binding to the same epitope in vivo will stabilise the configuration between C5 and tm-gp41 and/or C2.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome-binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%-99% homogeneity for antibody molecules in the context of all present peptide species in the composition or at least with respect to substantially active peptide species in the context of proposed use.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The term antigen denotes a substance of matter which is recognized by the immune system's specifically recognizing components (antibodies, T-cells).

The term "immunogen" is in the present context intended to denote a substance of matter, which is capable of inducing an adaptive immune response in an individual, where said adaptive immune response targets the immunogen. In other words, an immunogen is an antigen, which is capable of inducing immunity.

The terms "epitope", "antigenic determinant" and "antigenic site" are used interchangeably herein and denotes the region in an antigen or immunogen which is recognized by antibodies (in the case of antibody binding epitopes, also known as "B-cell epitopes") or by T-cell receptors when the epitope is complexed to an MHC molecule (in the case of T-cell receptor binding epitopes, i.e. "T-cell epitopes").

The term "immunogenically effective amount" has its usual meaning in the art, i.e. an amount of an immunogen, which is capable of inducing an immune response, which significantly engages pathogenic agents, which share immunological features with the immunogen.

The term "vaccine" is used for a composition comprising an immunogen and which is capable of inducing an immune response which is either capable of reducing the risk of developing a pathological condition or capable of inducing a therapeutically effective immune response which may aid in the cure of (or at least alleviate the symptoms of) a pathological condition.

The term "pharmaceutically acceptable" has its usual meaning in the art, i.e. it is used for a substance that can be accepted as part of a medicament for human use when treating the disease in question and thus the term effectively excludes the use of highly toxic substances that would worsen rather than improve the treated subject's condition.

A "T helper lymphocyte epitope" (a $T_H$ epitope) is peptide, which binds an MHC Class II molecule and can be presented on the surface of an antigen presenting cell (APC) bound to the MHC Class II molecule. An "immunological carrier" is generally a substance of matter which includes one or many $T_H$ epitopes, and which increase the immune response against an antigen to which it is coupled by ensuring that T-helper lymphocytes are activated and proliferate. Examples of known immunological carriers are the tetanus and diphtheria toxoids and keyhole limpet hemocyanin (KLH).

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

Peptides that Stimulate Cell-Mediated Immunity (CMI)

Vaccination aims to stimulate the immune response to a specific pathogen in advance of infection. When an individual is exposed to that pathogen, a memory response is triggered which prevents the establishment of infection. Vaccines therefore stimulate the adaptive immune response which unlike innate immunity, is long lived and has memory.

There are two major arms to the adaptive immune system. Humoral immunity which involves the development of antibodies that can bind virus particles and certain antibodies that can neutralize infection. Cell mediated immunity that leads to the development of cytotoxic T-cells that kill infected cells exposing viral epitopes in the context of human leukocyte antigen (HLA) class I, in this way eliminating infected cells.

As used herein a peptide that elicits a cell-mediated immune response refers to any peptide that elicits an activation of antigen-specific cytotoxic T-lymphocytes. These peptides elicit a Cytotoxic T-lymphocyte immune (CTL) response that leads to the development of cytotoxic T-cells that kill infected cells exposing viral epitopes in the context of human leukocyte antigen (HLA) class I, in this way eliminating infected cells. Cell-mediated immunity (CMI) may also involve the activation of phagocytes, natural killer cells (NK), antigen-specific cytotoxic T-lymphocytes, and the release of various cytokines in response to an antigen.

These peptides may be a helper T lymphocyte (HTL) inducing peptide comprising HTL epitopes. A "HTL inducing peptide" is a HLA Class II binding peptide that is capable of inducing a HTL response. Also the peptides may in other embodiments be CTL inducing peptides comprising CTL epitopes in addition to or as an alternative to being a HTL inducing peptide. A "CTL inducing peptide" is a HLA Class I binding peptide that is capable of inducing a CTL response.

A peptide that elicit a cell-mediated immune response as used according to the present invention includes but is not limited to any peptide described in any one of international patent applications WO0052040, WO 2012/092934 or WO 2012/072088, which patent applications are hereby incorporated by reference.

HIV-Specific Peptides

In some aspects, the compositions according to the present invention comprise one or more peptide that elicits a cell-mediated immune response. In some embodiments, this peptide is at least one HIV-specific peptide.

One aspect of the peptides that elicits a cell-mediated immune response relates to HIV-specific peptides based on conserved regions of HIV gag p24, antigens in free or carrier-bound form comprising at least one of the said peptides.

The HIV-specific peptides to be used according to the invention may originate from conserved areas of the HIV-1 core protein p24, having the properties of maintaining the uniqueness (sensitivity and specificity) of the HIV-1-epitope. Further the new peptides to be used according to the invention possess no recognized cytotoxic T lymphocyte (CTL) antagonistic effect and shall have at least one potential CTL epitope.

In some embodiments, the HIV-specific peptides, to be used according to the present invention, and which have met the above criteria are selected from the following groups;

(SEQ ID NO: 47)

$Xaa_1$ $Xaa_2$ $Xaa_3$ $Xaa_4$ $Xaa_5$ $Xaa_6$ Ala $Xaa_8$ $Xaa_9$ Gln

Thr Pro Trp $Xaa_{14}$ $Xaa_{15}$ $Xaa_{16}$ $Xaa_{17}$ $Xaa_{18}$ Val $Xaa_{20}$;

Wherein Xaa in position 1 of the peptide derivate is Lys or Arg,
Xaa in position 2 is Ala, Gly, Ser or Arg,
Xaa in position 3 is Leu or Met,
Xaa in position 4 is Gly or Arg,
Xaa in position 5 is Pro, Thr, Val, Ser, Gln or Ala,
Xaa in position 6 is Gly, Ala, Lys, Arg, Gln or Glu,
Xaa in position 8 is Thr or Ser,
Xaa in position 9 is Leu or Ile,
Xaa in position 14 is Thr, Ser or Val,
Xaa in position 15 is Ala or Ser,
Xaa in position 16 is Cys or Ser,
Xaa in position 17 is Gln or Leu,
Xaa in position 18 is Gly, Glu or Arg, and
Xaa in position 20 is Gly or Arg;

(SEQ ID NO: 50)
$Xaa_1$ $Xaa_2$ $Xaa_3$ $Xaa_4$ $Xaa_5$ Gly Leu Asn Pro Leu Val $[Gly]_n$ $Xaa_{12}$ $Xaa_{13}$ Tyr $Xaa_{15}$ Pro $Xaa_{17}$ $Xaa_{18}$ Ile

Leu $Xaa_{21}$ $Xaa_{22}$ wherein Xaa in position 1 is Arg, Lys, Asp or none
Xaa in position 2 is Trp, Gly, Lys or Arg,
Xaa in position 3 is Ile, Leu, Val or Met
Xaa in position 4 is Ile, Val or Leu
Xaa in position 5 Leu, Met, Val or Pro
Xaa in position 12 is Arg, Lys
Xaa in position 13 is Met or Leu,
Xaa in position 15 is Ser, Cys or Gln,
Xaa in position 17 is Thr, Val, Ile, Ser or Ala,
Xaa in position 18 is Ser, Gly or Thr,
Xaa in position 21 is Asp, Glu, Cys or Gly,
Xaa in position 22 is Gly or none, and
n=0, 1, 2 or 3;

(SEQ ID NO: 55)
$Xaa_1$ $Xaa_2$ $Xaa_3$ Pro Ile Pro $Xaa_7$ $Xaa_8$ $Xaa_9$ $Xaa_{10}$ $Xaa_{11}$ $Xaa_{12}$ $[Gly]_n$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ $Xaa_{22}$ $Xaa_{23}$ $Xaa_{24}$ wherein Xaa in position 1 is Asn, Ser, Gly, His, Ala, Pro, Arg or none
Xaa in position 2 is Asn, Ala or Lys
Xaa in position 3 is Pro, Gln, Gly, Ile or Leu
Xaa in position 7 is Val or Ala
Xaa in position 8 is Gly or Lys
Xaa in position 9 is Glu, Asp, Lys, Phe or Thr
Xaa in position 10 is Ile, Met, Val or Leu
Xaa in position 11 is Tyr, Leu or none
Xaa in position 12 is Ser or none
Xaa in position 13 is Arg or none
Xaa in position 14 is Asp, Arg, Trp, Ala or none
Xaa in position 15 is Ile or none
Xaa in position 16 is Tyr or none
Xaa in position 17 is Lys or Arg
Xaa in position 18 is Arg, Lys or Asp
Xaa in position 19 is Trp or Gly
Xaa in position 20 is Ile, Met, Val, Gln or Ala
Xaa in position 21 is Ile, Val or Ala
Xaa in position 22 is Leu, Met or Val
Xaa in position 23 is Gly or Cys
Xaa in position 24 is Leu or none,
n=1, 2 or 3, and (SEQ ID NO: 61)
$Xaa_1$ $Xaa_2$ Ile Ile $Xaa_5$ $Xaa_6$ $Xaa_7$ $Xaa_8$ $Xaa_9$ Leu $Xaa_{11}$ $[Gly]_n$ $[Arg]_m$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ $Xaa_{22}$ $Xaa_{23}$ $Xaa_{24}$ $Xaa_{25}$ wherein the Xaa in position 1 is Pro, Lys, Arg or none
Xaa in position 2 is Glu, Arg, Phe or Lys
Xaa in position 5 is Pro or Thr
Xaa in position 6 is Met, Thr or Nleu
Xaa in position 7 is Phe or Leu
Xaa in position 8 is Ser, Thr, Ala or Met
Xaa in position 9 is Ala, Glu or Leu
Xaa in position 11 is Ser or none
Xaa in position 12 is Ala, Arg or none
Xaa in position 13 is Ile, Leu or none
Xaa in position 14 is Ser, Ala, Leu or none
Xaa in position 15 is Tyr, Glu or Asp
Xaa in position 16 is Gly or Asp
Xaa in position 17 is Ala or Leu
Xaa in position 18 is Thr, Ile, Val, Leu or Asn,
Xaa in position 19 is Pro, Thr or Ser
Xaa in position 20 is Tyr, Phe, Nleu, His or Gln
Xaa in position 21 is Asp, Asn, Leu or Ala
Xaa in position 22 is Leu, Ile, Val or Asn
Xaa in position 23 is Asn, Tyr, Cys or Gly
Xaa in position 24 is Thr, Met, Ile, Ala, Val or none
Xaa in position 25 is Gly or none
n=1, 2 or 3 and m=0, 1, 2 or 3 independent of each other, the terminal ends of each HIV specific peptide may be free carboxyl- or amino groups, amides, acyls, acetyls or salts thereof.

The HIV-specific peptide sequences have the potential to serve as a good antigen wherein the antigen comprises at least one peptide selected from the group of sequences of SEQ ID NO:47, SEQ ID NO:50, SEQ ID NO:55 or SEQ ID NO:61. The antigenicity may be adapted through adjusting the ratio or concentration of different peptides or size of the peptides by for instance dimerisation or polymerisation and/or immobilisation to a solid phase. The antigen comprises two or more polypeptide sequences, to be used according to the invention, which are either linked by a bridge for instance a disulphide bridge between the Cys residues of the chains or bridges like $C_1$-$C_8$ alkylen possibly intervened by one or more heteroatoms like O, S, or N or preferably they are unlinked. The chains may be immobilized to a solid phase in monomeric, dimeric or oligomeric forms. Further amino acids may be added to the ends in order to achieve an «arm» to facilitate immobilization.

All amino acids in the HIV-specific peptides to be used according to the invention can be in both D- or L-form, although the naturally occurring L-form is preferred.

The C- and N-terminal ends of the HIV-specific peptide sequences could deviate from the natural sequences by modification of the terminal $NH_2$-group and/or COOH-group, they may for instance be acylated, acetylated, amidated or modified to provide a binding site for a carrier or another molecule.

The HIV-specific peptides to be used according to the invention are consisting of 6 to 50 amino acids, preferably between 10 and 30 amino acids. They are covering all natural variation of amino acids in the identified positions.

The polypeptide antigen to be used according to the invention is either in a free or in a carrier-bound form. The carrier or solid phase to which the peptide is optionally bound can be selected from a wide variety of known carriers. It should be selected with regard to the intended use of the immobilized polypeptide as a diagnostic antigen or as an immunizing component in a vaccine.

Examples of carriers that can be used for e.g. diagnostic purposes are magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatine or polysaccharide particles or other protein particles, red blood cells, mono- or polyclonal antibodies or fab fragments of such antibodies.

In one embodiment of the vaccine according to the present invention comprises antigens containing the peptides of the SEQ ID NO:47, 50, 55 and 61, more preferred the peptides occur in the ratio 1:1:1:1.

In a further preferred embodiment the vaccine composition contains the antigens;

RALGPAATLQTPWTASLGVG-NH$_2$ (SEQ ID NO: 49)

RWLLLGLNPLVGGGRLYSPTSILG-NH$_2$ (SEQ ID NO: 52)

RAIPIPAGTLLSGGGRAIYKRTAILG-NH$_2$ (SEQ ID NO: 57)
and

RFIIPNIFTALSGGRRALLYGATPYAIG-NH$_2$. (SEQ ID NO: 64)
(NI in position 6 is Norleucine).

One of the sequences contains a B-cell epitope and will activate the humoral immune system, whereas the other sequences contribute with CTL-epitopes and the amino acid changes implemented within the frame of the CTL-epitope are designed to achieve enhanced binding. Other amino acid changes have been conducted in order to facilitate the synthesis of the peptide and/or increase the solubility of the peptide.

Compound that Stimulate a Humoral Response in a Subject, Such as C5 Related Compounds:

The present invention also relates to the use of compounds that stimulate the humoral immunity in a subject. Humoral immunity involves the development of antibodies that can bind virus particles and certain antibodies that can neutralize infection.

A peptide that stimulate the humoral immunity in a subject as used according to the present invention includes but is not limited to any peptide described in any one of international patent applications WO2011/000962, WO0052040, WO 2012/092934 or WO 2012/072088, which patent applications are hereby incorporated by reference.

In some embodiments these compounds are agents capable of stabilising the association of the C5 domain of HIV gp120 with the transmembrane domain of gp41 and/or with the constant C2 domain of gp120. In other embodiments these compounds are immunogens, which induces antibodies that stabilise association of the C5 domain of HIV gp120 with the transmembrane domain of gp41 and/or with the constant C2 domain of gp120.

One aspect of the invention relates to compositions and method for reducing and/or delaying pathological effects of human retrovirus infection, such as immunodeficiency virus I (HIV) in a human infected with such virus, such as HIV, the method including administering an effective amount of an agent capable stabilising association of the C5 domain of HIV gp120 with the transmembrane domain of gp41 and/or with the constant C2 domain of gp120.

Another aspect is much similar, but relates to compositions and methods of reducing the risk of developing acquired immunodeficiency syndrome (AIDS), the method including administering an effective amount of an agent capable of stabilising association of the C5 domain of HIV gp120 with the transmembrane domain of gp41 and/or with the constant C2 domain of gp120.

These aspects primarily aim at treating retrovirus infections, such as HIV infected individuals with agents, which can mimic the antibodies which according to the present invention are characteristic for HIV infected long-term non-progressors—this is the most straightforward therapeutic utilisation of the findings underlying the present invention. Where the one aspect aims at reducing pathological effects of retrovirus infections, such as HIV or prolonging the time it takes to develop manifest AIDS, the other aspect aims at reducing the risk of developing AIDS altogether and may therefore be used in individuals which are currently treated prophylactically with antiretroviral therapy.

In one embodiment, the agent in these first aspects of the invention is a molecule comprising at least one amino acid sequence selected independently from an amino acid sequence derived from the transmembrane domain of gp41 and an amino acid sequence derived from the C2 domain, wherein the at least one amino acid sequence binds the C5 domain and optionally comprises at least one D-amino acid; in certain embodiments all the amino acids in the amino acid sequence are D-amino acids. The molecule is preferably a peptide, and in certain embodiments this peptide consists of the at least one amino acid sequence. The amino acid sequences typically include at most 10 amino acid residues, such as at most 9, at most 8, at most 7, at most 6, and at most 5 amino acid residues. Preferred molecules are therefore peptides having 4, 5, 6, 7, 8, 9, or 10 amino acid residues. Specific embodiments of the at least one molecule are therefore the peptides having or comprising SEQ ID NO:34, 35, 36, 37, 39, 40, 42, 43 and 45, which may all be composed partly or entirely of D-amino acids. Also molecules comprising peptides having Formula III are interesting embodiments of the at least one molecule.

In one embodiment, the agent in these first aspects of the invention is selected from an antibody, an antibody fragment or an antibody analogue. The antibody may be a fully human antibody, a humanized antibody, or a chimeric antibody, or a derivative thereof. Typically, the antibody is an IgA, an IgD, an IgG, an IgE or an IgM—the antibody may be both monoclonal and polyclonal. The antibody fragment is typically selected from a Fab fragment, a Fab' fragment, a Fab'-SH fragment, a F(ab)2 fragment, a F(ab')2 fragment, an Fv fragment, a Heavy chain Ig (a llama or camel Ig), a V$_{HH}$ fragment, a single domain FV, and a single-chain antibody fragment, and the antibody analogue is typically selected from a scFV, a dsFV, a minibody, a diabody, a triabody, a kappa body, an IgNAR, a tandAb, a BITE, and a multispecific antibody.

In one embodiment of these first aspects of the invention, the agent binds to and stabilises association between one or more amino acid residues in the amino acid stretch TZ$^1$AKRRVVZ$^2$REKR, where Z$^1$ is K, R or E and where Z$^2$ is Q or E, and one or more amino acid residues in an amino acid stretch in the transmembrane domain of gp41 and/or in the constant C2 domain of gp120. This amino acid stretch from C5 is highly conserved across the multiple HIV clades known and effective interaction with this stretch by the agent is therefore believed to be highly advantageous.

A further aspect of the invention relates to a method for reducing the risk of or reducing and/or delaying pathological effects of human immunodeficiency virus I (HIV) in a human infected with HIV, the method including administering an effective amount of an immunogen, which induces antibodies that stabilise association of the C5 domain of HIV gp120 with the transmembrane domain of gp41 and/or with the constant C2 domain of gp120, whereas other aspects relates to a prophylactic method using the same means. In other words, one aspect relates to therapeutic active immunotherapy, whereas another aspect relates to prophylactic immunotherapy of HIV disease, including AIDS. This also entails prophylaxis of HIV infection.

These particular aspects are based on the realisation that it is feasible to induce the same type of antibody repertoire in the average HIV infected individual as the one that is found in the HIV LTNP individuals. By carefully selecting peptide regions in both C5 and in tm-gp41 and/or C2 in order to prepare peptide multimers that mimic the antibody binding epitopes present in HIV composed of these regions, it becomes possible to prepare vaccines which will induce the desired immunity—interestingly, this approach does not aim at vaccinating so as to obtain neutralizing antibodies in the classical sense.

In one embodiment the immunogen is selected from a peptide multimer detailed below when discussing these aspects of the invention, a composition detailed below, a nucleic acid fragment discussed in relation to other aspects, a virus or plasmid vector compositions discussed elsewhere.

In common for the first aspects is that they all include embodiments where the targeted association between the C5 domain and C2 and/or the transmembrane domain of gp41 involves at least one amino acid in the sequence TZ$^1$AKRRVVZ$^2$REKR, where Z$^1$ is K, R or E and where Z$^2$ is Q or E and an amino acid and involves at least one amino acid in the transmembrane domain of gp41 or at least one amino acid in the constant C2 domain of gp120. As explained above, this particular sequence is extremely well-conserved across known HIV clades, and therefore it is the interaction between this sequence and tm-gp41 or C2 it is most feasible to target.

Another aspect relates to a composition comprising (1) a peptide multimer, said multimer comprising
  a first peptide comprising the amino acid sequence of the 13 amino acid residue amino acid sequence of the C5 domain of HIV gp120 including between 0 and 4 amino acid substitutions, a subsequence thereof, or an amino acid sequence comprising the inverso-, retro- or retro-inverso form of said amino acid sequence or subsequence, and
  at least one second peptide comprising an amino acid stretch present in the transmembrane domain of gp41 or present in the constant C2 domain of gp120 or comprising an amino acid stretch present in any one of SEQ ID NOs. 6-13 or comprising an inverso-, retro- or retro-inverso form of an amino acid stretch present in the transmembrane domain of gp41 or present in the constant C2 domain of gp120,
  wherein said peptide multimer is capable of inducing an antibody which can bind and stabilise the association of the C5 domain of HIV gp120 with the transmembrane domain of gp41 and/or with the constant C2 domain of gp120, and wherein said peptide multimer lacks amino acids N-terminal of C5 in gp120.

In other words, this aspect relates to peptide multimers which have a resemblance in 3 dimensions with the epitopes which characterise the interacting areas in C5 on the one hand and tm-gp41 and/or C2 on the other. The peptide multimers to be used according to the invention are useful immunogens that can induce antibodies having the same characteristics as the antibodies found in HIV LTNP individuals, but the peptide multimers also are promising as diagnostic/prognostic tools. The inclusion of retro-, inverso-, and retro-inverso peptides i.a. enables production of proteolytically stable peptides as well as peptides are truly foreign compared to the HIV counterpart.

In one embodiment of the peptide multimer, said first peptide comprises the amino acid sequence having formula I:

$$X^1\text{-}X^2\text{-}X^3\text{-}X^4\text{-}X^5\text{-}X^6\text{-}X^7\text{-}X^8\text{-}X^9\text{-}X^{10}\text{-}X^{11}\text{-}X^{12}\text{-}X^{13} \quad (I)$$

wherein $X^1$ is Thr, $X^2$ is selected from Lys, Arg, Har and Glu, $X^3$ is selected from Ala and Val,
$X^4$ is selected from Arg, Har, Lys and Cit (citrulline), $X^5$ is selected from Arg, Har, Lys and Cit,
$X^6$ is selected from Arg, Har, Lys and Cit, $X^7$ is selected from Val, Leu, Ile and Nle (norleucin),
$X^8$ is selected from Val, Leu Ile and Nle, $X^9$ is selected from Gln, Glu, Asn and Asp, $X^{10}$ is selected from Arg, Har and Cit, $X^{11}$ is selected from Glu and Asp, $X^{12}$ is Lys, and $X^{13}$ is selected from Arg, Har and Cit,
or comprises a subsequence the amino acid sequence of formula I, or comprising the inverso-, retro- or retro-inverso form of said amino acid sequence or subsequence. The first peptide may further comprise the dipeptide Ala-Pro linked to the N-terminus of the amino acid sequence having formula I and/or the first peptide may further comprise the dipeptide $X^{14}\text{-}X^{15}$ linked to the C-terminus of the amino acid sequence having formula I, wherein $X^{14}$ is selected from Ala and Val, and wherein $X^{15}$ is selected from Val, Leu and Nle.

Particularly interesting peptides derived from C5 are set forth in the preamble to the Examples and constitute embodiments of a first peptide of the peptide multimers to be used according to the invention.

A number of naturally occurring mutants of gp41 and gp120 has been observed, so when stating that the second peptide comprises an amino acid stretch present in the transmembrane domain of gp41 or present in the constant C2 domain of gp120, this is intended to denote that the amino acid stretch is present in any such naturally occurring form. So, the at least second peptide, when derived from gp41, is in certain embodiments one which includes the amino acid sequence having the formula:

$$Z^1\text{-}Z^2\text{-}Z^3\text{-}Z^4\text{-}Z^5\text{-}Z^6\text{-}Z^7\text{-}Z^8\text{-}Z^9\text{-}Z^{10}\text{-}Z^{11}\text{-}Z^{12}\text{-}Z^{13}\text{-}Z^{14}\text{-}Z^{15}\text{-}Z^{16}\text{-}Z^{17} \quad (III)$$

wherein $Z^1$ is Asp, $Z^2$ is Arg, $Z^3$ is Pro, $Z^4$ is Glu or Gly, $Z^5$ is Gly or Arg, $Z^6$ is Ile, $Z^7$ is Glu, $Z^8$ is Glu, $Z^9$ is Glu, $Z^{10}$ is Gly, $Z^{11}$ is Gly, $Z^{12}$ is Glu or is absent, $Z^{13}$ is Arg or Gln, $Z^{14}$ is Asp or Gly, $Z^{15}$ is Arg or Lys, $Z^{16}$ is Asp or Gly and $Z^{12}$ is Arg,
or includes a subsequence of formula (III), such as a subsequence having at least 5 amino acid residues (such as at least 6, at least 7, at least 8, at least 9, at least 10, at least 11, at least 12, at least 13, at least 14, at least 15, and at least 16 amino acid residues). Further, this embodiment of the second peptide may contain amino acid substitutions which result in a sequence identity of at least 80% with a corresponding amino acid sequence found in gp41.

Particularly interesting peptides derived from C2 and gp41, and gp120 are set forth in the preamble to the Examples and constitute embodiments of a second peptide of the peptide multimers to be used according to the invention.

In certain embodiments of the peptide multimer, the first peptide and the at least one second peptide are associated via a linker; the linker can be any peptide linker, such as a glycine, a lysine or an arginine linker, a polyhistidinyl tag, Protein G, and Protein A but it is also possible to use a bis-maleimide linker, a disulfide linker, or a polyethylene glycol (PEG) linker. In practice, any linker found useful in peptide chemistry is also useful as a linker according to the present invention. Thus, the invention contemplates the use of "simple" linear peptides which are conjugated or fused to each other, but also peptide multimers where the individual peptides derived from C5 and other regions of gp120 or gp41 are linked via non-peptide linkers e.g. complementary nucleic acids, nucleic acid derivatives or analogues e.g. PNA, LNA. Use of multiple linker types are also within the scope of the present invention, and it is e.g. also a part to be used according to the invention to utilise linear peptides which include intrachain disulphide linkers.

Particularly interesting peptide multimers to be used according to the invention are set forth in the preamble to the examples.

In certain embodiments, at least one of the first and at least one second peptides in the peptide multimer comprises an N- or C-terminal modification, such as an amidation, acylation, or acetylation.

Since the peptide multimers are contemplated as vaccine agents or diagnostic agents, they are in certain embodiments coupled to a carrier molecule, such as an immunogenic carrier. The peptides of the peptide multimers may thus be linked to other molecules either as recombinant fusions (e.g. via CLIP technology) or through chemical linkages in an oriented (e.g. using heterobifunctional cross-linkers) or non-oriented fashion. Linking to carrier molecules such as for example diphtheria toxin, latex beads (convenient in diagnostic and prognostic embodiments), and magnetic beads (also convenient in diagnostic and prognostic embodiments), polylysine constructs etc, are all possible carrier molecules to be used according to the invention.

The immunogenic carrier is conveniently selected from carrier proteins such as those conventionally used in the art (e.g. diphtheria or tetanus toxoid, KLH etc.), but it is also possible to use shorter peptides (T-helper epitopes) which can induce T-cell immunity in larger proportions of a population. Details about such T-helper epitopes can e.g. be found in WO 00/20027, which is hereby incorporated by reference herein—all immunolgic carriers and "promiscuous" (i.e. universal) T-helper epitopes discussed therein are useful as immunogenic carriers in the present invention.

In certain embodiments, the carrier is a virus like particle, i.e. a particle sharing properties with virions without being infectious. Such virus-like particles may be provided chemically (e.g. Jennings and Bachmann Ann Rev Pharmacol. Toxicol. 2009. 49:303-26 Immunodrugs: Therapeutic VLP-based vaccines for chronic diseases) or using cloning techniques to generate fusion proteins (e.g. Peabody et al. J. Mol. Biol. 2008; 380: 252-63. Immunogenic display of diverse peptides on virus-like particles of RNA phage MS2). Another example is "Remune", an HIV vaccine originally made by Immune Response Corporation, which consists of formalin inactivated HIV that has been irradiated to destroy the viral genome. The company was started by Jonas Salk who used the same technique to generate the killed polio vaccine in widespread use today. However, on fixation of HIV, gp120 fell off leaving only gp41 on the virion surface. This opens for the possibility of directly admixing C5-derived peptides disclosed herein with Remune particles, because it should still be possible to obtain the binding between C5 and gp41 on a Remune particle.

Embodiments of the aspect related to peptide multimers also include those wherein the first peptide is selected from the group consisting of SEQ ID NO:1, 2, 3, 4, and 5 or a fragment thereof, or the inverso-, retro- or retro-inverso form of a peptides selected from SEQ ID NO:1, 2, 3, 4, and 5 or a fragment thereof, and wherein the second peptide is selected from the group consisting of SEQ ID NO:6, 7, 8, 9, 10, 11, 12, 13, or 46 or a fragment thereof or the inverso-, retro- or retro-inverso form of a peptides selected from SEQ ID NO:6, 7, 8, 9, 10, 11, 12, 13, or 46 or a fragment thereof. As mentioned above, in such a case the fragment may be very short, as long as the peptide multimer provides for the ability to induce antibodies which will stabilise association between C5 and gp41 and/or C2. A number of interesting peptide multimers of the present invention are listed in the Preamble to the Examples.

In an embodiment, the peptide multimer to be used according to the invention comprises at most 70 amino acids, such as the most 69, at most 68, at most 67, at most 66, at most 65, at most 64, at most 63, at most 62, at most 61, at most 60, at most 59, at most 58, at most 57, at most 56, at most 55, at most 54, at most 53, at most 52, at most 51, at most 50, at most 49, at most 48, at most 47, at most 46, at most 45, at most 44, at most 43, at most 42, at most 41, at most 40, at most 39, at most 38, at most 37, at most 36, at most 35, at most 34, at most 33, at most 32, at most 31, at most 30, at most 29, at most 28, at most 27, at most 26, at most 25, at most 24, at most 23, at most 22, at most 21, at most 20, at most 19, at most 18, at most 17, at most 16, at most 15, at most 14, at most 13, at most 12, at most 11, at most 10, at most 9, at most 8, and at most 7 amino acids.

In an embodiment, the peptide multimer to be used according to the invention comprises at least 6 amino acid residues, such as at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, and at least 69 amino acid residues.

In one embodiment, the peptide multimer to be used according to the invention consists of 6 amino acid residues or 7 amino acid residues or 8 amino acid residues or 9 amino acid residues or 10 amino acid residues or 11 amino acid residues or 12 amino acid residues or 13 amino acid residues or 14 amino acid residues or 15 amino acid residues or 16 amino acid residues or 17 amino acid residues or 18 amino acid residues or 19 amino acid residues or 20 amino acid residues or 21 amino acid residues or 22 amino acid residues or 23 amino acid residues or 24 amino acid residues or 25 amino acid residues or 26 amino acid residues or 27 amino acid residues or 28 amino acid residues or 29 amino acid residues or 30 amino acid residues or 31 amino acid residues or 32 amino acid residues or 33 amino acid residues or 34 amino acid residues or 35 amino acid residues or 36 amino acid residues or 37 amino acid residues or 38 amino acid residues or 39 amino acid residues or 40 amino acid residues or 41 amino acid residues or 42 amino acid residues or 43 amino acid residues or 44 amino acid residues or 45 amino acid residues or 46 amino acid residues or 47 amino acid residues or 48 amino acid residues or 49 amino acid residues or 50 amino acid residues or 51 amino acid residues or 52 amino acid residues or 53 amino acid residues or 54 amino acid residues or 55 amino acid residues or 56 amino acid residues or 57 amino acid residues or 58 amino acid residues or 59 amino acid residues or 60 amino acid residues or 61 amino acid residues or 62 amino acid residues or 63 amino acid residues or 64 amino acid residues or 65 amino acid residues or 66 amino acid residues or 67 amino acid residues or 68 amino acid residues or 69 amino acid residues or 70 amino acid residues.

In one embodiment, the peptide multimer to be used according to the invention is selected from the group consisting of disulphide linked peptides between SEQ ID NO:28 and any one of SEQ ID NOs: 29, 31, and 33, between SEQ ID NO:30, and any one of SEQ ID NO:29, 31, and 33, or between SEQ ID NO:32 and any one of SEQ ID NO:29, 31, and 33; or selected from the group consisting of cysteine-lysine linked peptides between SEQ ID NO:38 and any one of SEQ ID NO:39, SEQ ID NO:40; SEQ ID NO:42, SEQ ID NO:43, and SEQ ID NO:68, or between SEQ ID NO:41 and any one of SEQ ID NO:39, SEQ ID NO:40; SEQ ID NO:42, and SEQ ID NO:43.

In one embodiment, the peptide multimer to be used according to the invention is selected from the group consisting of:

```
CGGAKRRVVGGAKRRVVGQREKRAV (SEQ ID NO: 28)
|
CGGGDQQLLGGAEEEIVGGIEEEGGERDRDR, (SEQ ID NO: 29)

CGGAKRRVVGGAKRRVVGGQREKR (SEQ ID NO: 30)
|
CGGGDQQLLGGAEEEIVGGIEEEGG, (SEQ ID NO: 31)

CGGAEEEVVGGDQQLL (SEQ ID NO: 32)
|
GCGGAKRRVVGGAKRRVV, (SEQ ID NO: 33)

GAKRRVVGGCGGAKRRVVQREKRAGEREKRA (SEQ ID NO: 38)
          |
      GKGGIEEEGGRDRDRGGEQDRDR, (SEQ ID NO: 39)

GAKRRVVGGCGGAKRRVVQREKRAGEREKRA (SEQ ID NO: 38)
          |
      GKGGIEEEGGERDRDRGGQDRDR, (SEQ ID NO: 40)

GAKRRVVGGCGGAKRRVVEREKRAGQREKRA (SEQ ID NO: 41)
          |
      GKGGIEEEGGQDRDRGGRDRDR, (SEQ ID NO: 42)

GAKRRVVGGCGGAKRRVVEREKRAGQREKRA (SEQ ID NO: 41)
          |
      GKGGIEEEGGEQDRDRGGERDRD (SEQ ID NO: 43)
and GAKRRVVGGCGGAKRRVVQREKRAGEREKRA (SEQ ID NO: 38)
          |
      GKGGIEEEGGRDRDRGGQDRDR (SEQ ID NO: 68)
```

In one embodiment, the peptide multimer to be used according to the invention is (H-Gly-Ala-Lys-Arg-Arg-Val-Val-Gly-Gly-Cys(2-oxo-ethyl)-Gly-Gly-Ala-Lys-Arg-Arg-Val-Val-Gln-Arg-Glu-Lys-Arg-Ala-Gly-Glu-Arg-Glu-Lys-Arg-Ala-NH2) (H-Gly-Lys-Gly-Gly-Ile-Glu-Glu-Glu-Gly-Gly-Arg-Asp-Arg-Asp-Arg-Gly-Gly-Gln-Asp-Arg-Asp-Arg-NH2), acetate salt (amide bond between Cys(2-oxo-ethyl)10 (A-chain) and Lys2 (B-chain)).

Another aspect relates to the use of an immunogenic composition (such as a vaccine composition) comprising a composition described herein in combination with a pharmaceutically acceptable diluent or vehicle and optionally one or more immunological adjuvant.

In some aspects the present invention relates to the use of one or more peptide that stimulate a cell-mediated immune response, such as with at least one HIV-specific peptide selected from the group of amino acid sequences:

(SEQ ID NO: 47)
$Xaa_1$ $Xaa_2$ $Xaa_3$ $Xaa_4$ $Xaa_5$ $Xaa_6$ Ala $Xaa_8$ $Xaa_9$ Gln

Thr Pro Trp $Xaa_{14}$ $Xaa_{15}$ $Xaa_{16}$ $Xaa_{17}$ $Xaa_{18}$ Val $Xaa_{20}$;

Wherein Xaa in position 1 of the peptide derivate is Lys or Arg,
Xaa in position 2 is Ala, Gly, Ser or Arg,
Xaa in position 3 is Leu or Met,
Xaa in position 4 is Gly or Arg,
Xaa in position 5 is Pro, Thr, Val, Ser, Gln or Ala,
Xaa in position 6 is Gly, Ala, Lys, Arg, Gln or Glu,
Xaa in position 8 is Thr or Ser,
Xaa in position 9 is Leu or Ile,
Xaa in position 14 is Thr, Ser or Val,
Xaa in position 15 is Ala or Ser,
Xaa in position 16 is Cys or Ser,
Xaa in position 17 is Gln or Leu
Xaa in position 18 is Gly, Glu or Arg, and
Xaa in position 20 is Gly or Arg;

(SEQ ID NO: 50)
$Xaa_1$ $Xaa_2$ $Xaa_3$ $Xaa_4$ $Xaa_5$ Gly Leu Asn Pro Leu Val $[Gly]_n$ $Xaa_{12}$ $Xaa_{13}$ Tyr $Xaa_{15}$ Pro $Xaa_{17}$ $Xaa_{18}$ Ile Leu $Xaa_{21}$ $Xaa_{22}$ wherein Xaa in position 1 is Arg, Lys, Asp or none
Xaa in position 2 is Trp, Gly, Lys or Arg,
Xaa in position 3 is Ile, Leu, Val or Met
Xaa in position 4 is Ile, Val or Leu
Xaa in position 5 Leu, Met, Val or Pro
Xaa in position 12 is Arg, Lys
Xaa in position 13 is Met or Leu,
Xaa in position 15 is Ser, Cys or Gln,
Xaa in position 17 is Thr, Val, Ile, Ser or Ala,
Xaa in position 18 is Ser, Gly or Thr,
Xaa in position 21 is Asp, Glu, Cys or Gly,
Xaa in position 22 is Gly or none, and
n=0, 1, 2 or 3;

(SEQ ID NO: 55)
$Xaa_1$ $Xaa_2$ $Xaa_3$ Pro Ile Pro $Xaa_7$ $Xaa_8$ $Xaa_9$ $Xaa_{10}$ $Xaa_{11}$ $Xaa_{12}$ $[Gly]_n$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ $Xaa_{22}$ $Xaa_{23}$ $Xaa_{24}$ wherein Xaa in position 1 is Asn, Ser, Gly, His, Ala, Pro, Arg or none
Xaa in position 2 is Asn, Ala or Lys
Xaa in position 3 is Pro, Gln, Gly, Ile or Leu
Xaa in position 7 is Val or Ala
Xaa in position 8 is Gly or Lys
Xaa in position 9 is Glu, Asp, Lys, Phe or Thr Xaa in position 10 is Ile, Met, Val or Leu
Xaa in position 11 is Tyr, Leu or none
Xaa in position 12 is Ser or none
Xaa in position 13 is Arg or none
Xaa in position 14 is Asp, Arg, Trp, Ala or none
Xaa in position 15 is Ile or none
Xaa in position 16 is Tyr or none
Xaa in position 17 is Lys or Arg
Xaa in position 18 is Arg, Lys or Asp
Xaa in position 19 is Trp or Gly
Xaa in position 20 is Ile, Met, Val, Gln or Ala
Xaa in position 21 is Ile, Val or Ala
Xaa in position 22 is Leu, Met or Val
Xaa in position 23 is Gly or Cys
Xaa in position 24 is Leu or none,
n=1, 2 or 3, and (SEQ ID NO: 61)
$Xaa_1\ Xaa_2\ Ile\ Ile\ Xaa_5\ Xaa_6\ Xaa_7\ Xaa_8\ Xaa_9\ Leu\ Xaa_{11}$ $[Gly]_n\ [Arg]_m\ Xaa_{12}\ Xaa_{13}\ Xaa_{14}\ Xaa_{15}\ Xaa_{16}\ Xaa_{17}\ Xaa_{18}$ $Xaa_{19}\ Xaa_{20}\ Xaa_{21}\ Xaa_{22}\ Xaa_{23}\ Xaa_{24}\ Xaa_{25}$ wherein the Xaa in position 1 is Pro, Lys, Arg or none
Xaa in position 2 is Glu, Arg, Phe or Lys
Xaa in position 5 is Pro or Thr
Xaa in position 6 is Met, Thr or Nleu
Xaa in position 7 is Phe or Leu
Xaa in position 8 is Ser, Thr, Ala. or Met
Xaa in position 9 is Ala, Glu or Leu
Xaa in position 11 is Ser or none
Xaa in position 12 is Ala, Arg or none
Xaa in position 13 is Ile, Leu or none
Xaa in position 14 is Ser, Ala, Leu or none
Xaa in position 15 is Tyr, Glu or Asp
Xaa in position 16 is Gly or Asp
Xaa in position 17 is Ala or Leu
Xaa in position 18 is Thr, Ile, Val, Leu or Asn,
Xaa in position 19 is Pro, Thr or Ser
Xaa in position 20 is Tyr, Phe, Nleu, His or Gln
Xaa in position 21 is Asp, Asn, Leu or Ala
Xaa in position 22 is Leu, Ile, Val or Asn
Xaa in position 23 is Asn, Tyr, Cys or Gly
Xaa in position 24 is Thr, Met, Ile, Ala, Val or none
Xaa in position 25 is Gly or none
n=1, 2 or 3 and m=0, 1, 2 or 3 independent of each other, the terminal ends of each HIV specific peptide may be free carboxyl- or amino groups, amides, acyls, acetyls or salts thereof.

In some embodiments two or more of the Cys residues of said HIV-specific peptide may form part of an intrachain- or interchain disulphide binding, a —S—$(CH_2)_p$—S— or a —$(CH_2)_p$— bridge wherein p=1-8 optionally intervened by one or more heteroatoms such as O, N and S and/or the said peptide sequences are immobilized to a solid support.

In some embodiments the amino acid sequence of SEQ ID NO:47 is selected from the groups of SEQ ID NO:48 and SEQ ID NO:49.

In some embodiments the amino acid sequence of SEQ ID NO:50 is selected from the groups of SEQ ID NO:51, SEQ ID NO:52, SEQ ID NO:53 and SEQ ID NO:54.

In some embodiments the amino acid sequence of SEQ ID NO:55 is selected from the groups of SEQ ID NO:56, SEQ ID NO:57, SEQ ID NO:58, SEQ ID NO:59 and SEQ ID NO:60.

In some embodiments the amino acid sequence of SEQ ID NO:61 is selected from the groups of SEQ ID NO:62, SEQ ID NO:63, SEQ ID NO:64, SEQ ID NO:65 and SEQ ID NO:66.

In some embodiments the at least one HIV-specific peptide comprises at least, two, three, or four peptides selected from each of the groups of SEQ ID NO:47, SEQ ID NO:50, SEQ ID NO:55 and SEQ ID NO:61.

In some embodiments the at least one HIV-specific peptide consist of or comprises the peptides of the SEQ ID NO:49, SEQ ID NO:52, SEQ ID NO:57 and SEQ ID NO:64.

In some embodiments the one or more peptide is in the form of an acetate salt.

In some embodiments one, two, three or four peptides are used in the therapeutic HIV-1 immunization phase.

In some embodiments the all four peptide as acetate salts are used in the therapeutic HIV-1 immunization phase.

In some embodiments the peptides have amide C-terminal ends of formula —C(O)NH2, or acetate salts thereof.

In some embodiments all four peptide are used in the ratio of 1:1:1:1 w/w.

In some embodiments one, two, three or four peptide acetate salts are in a dissolved liquid state. In some embodiments this liquid is water.

Specific Aspects and Embodiments of the Invention

One aspect of the present invention relates to the use of one or more HIV-specific peptide as defined above.

In certain embodiments, peptides comprise an N- or C-terminal modification, such as an amidation, acylation, or acetylation. When the C-terminal end of a peptide is an amide, suitable amides included those having the formula —C(O)—$NR^xR^y$, wherein $R^x$ and $R^y$ are independently selected from hydrogen and $C_{1-6}$ alkyl, which alkyl group may be substituted with one of more fluoro atoms, for example —$CH_3$, —$CH_2CH_3$ and —$CF_3$, a particular amide group which may be mentioned is —$C(O)NH_2$. When the N-terminal end of the peptide is acetylated, suitable acetylated N-terminal ends include those of formula —NH—C(O)$R^z$, wherein $R^z$ is hydrogen, $C_{1-6}$ alkyl, which alkyl group may be substituted with one of more fluoro atoms, for example —$CH_3$, —$CH_2CH_3$ and —$CF_3$, or phenyl.

Since the peptides are contemplated as vaccine agents or diagnostic agents, they are in certain embodiments coupled to a carrier molecule, such as an immunogenic carrier. The peptides may thus be linked to other molecules either as recombinant fusions (e.g. via CLIP technology) or through chemical linkages in an oriented (e.g. using heterobifunctional cross-linkers) or nonoriented fashion. Linking to carrier molecules such as for example diphtheria toxin, latex beads (convenient in diagnostic and prognostic embodiments), and magnetic beads (also convenient in diagnostic and prognostic embodiments), polylysine constructs etc, are all possible according to the invention.

The immunogenic carrier is conveniently selected from carrier proteins such as those conventionally used in the art (e.g. diphtheria or tetanus toxoid, KLH etc.), but it is also possible to use shorter peptides (T-helper epitopes) which can induce T-cell immunity in larger proportions of a population. Details about such T-helper epitopes can e.g. be found in WO 00/20027, which is hereby incorporated by reference herein—all immunolgic carriers and "promiscuous" (i.e. universal) T-helper epitopes discussed therein are useful as immunogenic carriers in the present invention.

In certain embodiments, the carrier is a virus like particle, i.e. a particle sharing properties with virions without being infectious. Such virus-like particles may be provided chemically (e.g. Jennings and Bachmann Ann. Rev. Pharmacol. Toxicol. 2009. 49:303-26 Immunodrugs: Therapeutic VLP-based vaccines for chronic diseases) or using cloning techniques to generate fusion proteins (e.g. Peabody et al. J. Mol. Biol. 2008; 380: 252-63. Immunogenic display of diverse peptides on virus-like particles of RNA phage MS2). Another example is "Remune", an HIV vaccine originally made by Immune Response Corporation, which consists of formalin inactivated HIV that has been irradiated to destroy the viral genome. The company was started by Jonas Salk who used the same technique to generate the killed polio vaccine in widespread use today.

Preparation of immunogenic compositions includes the use of state-of-the-art constituents such as immunological adjuvants. Apart from these adjuvants, which are detailed, by way of example, below, immunogenic compositions are prepared as generally taught in the art:

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines; cf. the detailed discussion of adjuvants below.

The vaccines are conventionally administered parenterally, by injection, for example, either subcutaneously, intracutaneously, intradermally, subdermally or intramuscularly. Additional formulations which are suitable for other modes of administration include suppositories and, in some cases, oral, nasal, buccal, sublingual, intraperitoneal, intravaginal, anal, epidural, spinal, and intracranial formulations. For suppositories, traditional binders and carriers may include, for example, polyalkalene glycols or triglycerides; such suppositories may be formed from mixtures containing the active ingredient in the range of 0.5% to 10% (w/w), preferably 1-2% (w/w). Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and may contain 10-95% (w/w) of active ingredient, preferably 25-70% (w/w).

The peptides may be formulated into a vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and organic bases such as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of immunity desired. Suitable dosage ranges are of the order of several hundred micrograms of active ingredient per vaccination with a preferred range from about 0.1 µg to 2,000 µg (even though higher amounts in the 1-10 mg range are contemplated), such as in the range from about 0.5 µg to 1,000 µg, preferably in the range from 1 µg to 500 µg and especially in the range from about 10 µg to 100 µg. Suitable regimens for initial administration and booster shots are also variable but are typified by an initial administration followed by subsequent inoculations or other administrations.

Some of the peptides are sufficiently immunogenic in a vaccine, but for some of the others the immune response will be enhanced if the vaccine further comprises an adjuvant substance. The immunogenic molecules described herein can therefore be formulated with adjuvants:

The adjuvants to be combined are known to induce humoral responses and include: i) Salt suspensions (e.g. varieties of salts containing aluminum ions or calcium ions), ii) Oil-in-water emulsions (e.g. varieties of squalane-based or squalene-based emulsions), iii) Water-in-oil emulsions (e.g. Montanide ISA51 or ISA720), iv) Neutral liposomes, v) Cationic liposomes, vi) Microspheres, vii) Immunostimulating complexes (e.g. ISCOMs or ISCOMATRIX), viii) Pattern-recognition receptor agonists (e.g. agonists for C-type lectin receptors (CLRs), NOD-like receptors (NLRs), RIG-like helicases (RLHs), Triggering receptor expressed on myeloid cells (TREMs) and Toll-like receptors (TLRs)), ix) Saponins (i.e. Any saponin derived from *Quillaja saponaria* or *Platycodon grandiflorum*), x) Virosomes/Virus-like particles, xi) Enterotoxins (i.e. Cholera toxin, CTA1-DD or *Escherichia coli* heat-labile enterotoxin), and combinations thereof.

For a further enhancement of the vaccine antigenic properties, they could be combined with a well known adjuvant with an oral immune modulant or adjuvant such as a Cox-2 inhibitor or a immunomodulating compound.

A further aspect of the invention is the use of the vaccine combined with adjuvant, with one or more further therapeutic agents, such as an (oral) immunomodulating agent and/or a second reservoir purging agent.

The terms "therapeutic agent", such as "immunomodulating agent" or virus reservoir purging agent as used herein, includes but is not limited to cytokines, such as interferons, monoclonal antibodies, such as anti-PD1 antibodies, cyclophosphamide, Thalidomide, Levamisole, and Lenalidomide.

"A virus reservoir purging agent", includes but is not limited to auranofin, IL-7, prostratin, bryostatin, HDAC inhibitors, such as vorinostat, Disulfiram and any suitable agent disclosed in any one of WO2013050422, WO2012051492 A3 and in Barton et al., Clinical Pharmacology & Therapeutics (2013); 93 1, 46-561, including but not limited to a NF-kappa-B-inducer selected from the group comprising: PMA, prostratin, bryostatin and TNF-alpha, and/or b) a histone deacetylase inhibitor selected from the different families (hydroxamates, cyclic peptides, aliphatic acids, and benzamides) including: TSA, SAHA, MS-275, aminosuberoyl hydroxamic acids, M-Carboxycinnamic acid bishydroxamate, LAQ-824, LBH-589, belinostat (PXD-101), Panobinostat (LBH-589), a cinnamic hydroxamic acid analogue of M-carboxycinnamic acid bishydroxamate, IF2357, aryloxyalkanoic acid hydroxamides, depsipeptide, apicidin, cyclic hydroxamic acid-containing peptide group of molecules, FK-228, red FK, cyclic peptide mimic linked by an aliphatic chain to a hydroxamic acid, butyrate, phenylbutyrate, sodium butyrate, valproic acid, pivaloyloxymethyl butyrate, 5 NOX-275, and MGCD0103. Any of the above virus reservoir purging agents may be used alone or in combination with any one other suitable virus reservoir purging agent, such as with another class of HIV inducers.

DNA methylation, probably together with repressive histone modifications, may also contribute to a "lock" in a silent state of the provirus and makes its return to an active state difficult. These observations suggest that HDAC or HMT or DNA methylation inhibitors together with efficient cART constitute good anti-latency drug candidates aimed at reducing/eliminating the pool of latent reservoirs to a level bearable by the host immune system.

Accordingly suitable immunomodulatory compounds or purging agents may be DNA methylation inhibitors selected from the two classes (non-nucleoside and nucleoside demethylating agents) including: 5-azacytidine (azacitidine), Sinefungin, 5-aza-2'-deoxycytidine (5-aza-CdR, decitabine), 1-3-Darabinofuranosyl-5-azacytosine (fazarabine) and dihydro-5-azacytidine (DHAC), 5-fluorodeoxycytidine (FdC), oligodeoxynucleotide duplexes containing 2-H pyrimidinone, zebularine, antisense oligodeoxynucleotides (ODNs), MG98, (−)-epigallocatechin-3-gallate, hydralazine, procaine and procainamide.

Other suitable immunomodulatory compounds or purging agents to be used according to the present invention includes histone deacetylase inhibitor selected from the different families of HDACI (hydroxamates, cyclic peptides, aliphatic acids, and benzamides) including TSA, SAHA, MS-275, aminosuberoyl hydroxamic acids, M-Carboxycinnamic acid bishydroxamate, LAQ-824, LBH-589, belinostat (PXD-101), Panobinostat (LBH-589), a cinnamic hydroxamic acid analogue of M-carboxycinnamic acid bishydroxamate, IF2357, aryloxyalkanoic acid hydroxamides, depsipeptide, apicidin, cyclic hydroxamic acid-containing peptide group of molecules, FK-228, red FK, cyclic peptide mimic linked by an aliphatic chain to a hydroxamic acid, butyrate, phenylbutyrate, sodium butyrate, valproic acid, pivaloyloxymethyl butyrate, 5 NOX-275, and MGCD0103.

Other suitable immunomodulatory compounds or purging agents to be used according to the present invention includes histone methyltransferase inhibitors (chaetocin and BIX-01294); Inhibitors of Enhances of Zeste 2 (EZH2)—such as 3-deazaneplanocin A (DZNep) used alone or in combination with other classes of immunomodulatory compounds or purging agents.

Other suitable adjuvants include response-selective C5a agonists, such as EP54 and EP67 described in Hung C Y et al. An agonist of human complement fragment C5a enhances vaccine immunity against *Coccidioides* infection. Vaccine (2012) and Kollessery G et al. Tumor-specific peptide based vaccines containing the conformationally biased, response-selective C5a agonists EP54 and EP67 protect against aggressive large B cell lymphoma in a syngeneic murine model. Vaccine (2011) 29: 5904-10.

Various methods of achieving adjuvant effect for the vaccine are thus known. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generation Immunological Adjuvants", 1995, Gregoriadis G et al. (eds.), Plenum Press, New York, ISBN 0-306-45283-9, both of which are hereby incorporated by reference herein, but a number of later publications also deal with the technology of incorporating adjuvants: Roestenberg M et al., PLoS One. 2008; 3(12):e3960. Epub 2008 Dec. 18; Relyveld E and Chermann J C, Biomed Pharmacother. 1994; 48(2):79-83; Hsu F J et al., Blood. 1997 May 1; 89(9):3129-35; Galli G et al., Proc Natl Acad Sci USA. 2009 May 12; 106(19):7962-7. Epub 2009 Apr. 27; Bojang K A et al., Lancet. 2001 Dec. 8; 358(9297):1927-34; Odunsi K et al., Proc Natl Acad Sci USA. 2007 Jul. 31; 104(31):12837-42. Epub 2007 Jul. 25; Patel G B and Sprott G D; Crit Rev Biotechnol. 1999; 19(4):317-57. Review; Agger E M et al., PLoS One. 2008 Sep. 8; 3(9):e3116; Kirby D J et al. J Drug Target. 2008 May; 16(4):282-93; Florindo H F et al., Vaccine. 2008 Aug. 5; 26(33):4168-77. Epub 2008 Jun. 17; Sun H X et al., Vaccine. 2009 May 28; Guy B, Nat Rev Microbiol. 2007 July; 5(7):505-17. Review.; Vandepapeliére P et al., Vaccine. 2008 Mar. 4; 26(10):1375-86. Epub 2008 Jan. 14; Ghochikyan A et al. Vaccine. 2006 Mar. 20; 24(13): 2275-82. Epub 2005 Dec. 5; Xie Y et al., Vaccine. 2008 Jun. 25; 26(27-28):3452-60. Epub 2008 May 1; Chung Y C et al., Vaccine. 2008 Mar. 28; 26(15):1855-62. Epub 2008 Feb. 25; Maier M et al., Vaccine. 2005 Oct. 25; 23(44):5149-59; Sundling C et al., J Gen Virol. 2008 December; 89(Pt 12):2954-64.

In the methods of the invention the one or more peptide to stimulate a cell-mediated immune response and/or a compound that stimulate a humoral response in a human, may be administered in combination with one or more further immunomodulatory compound and/or a reservoir purging agent, such as a histone deacetylase (HDAC) inhibitor.

The term "immunomodulating compound" or "reservoir purging agent" as used herein, includes but is not limited to cytokines, such as interferons, monoclonal antibodies, such as ant-PD1 antibodies, cyclophosphamide, Thalidomide, Levamisole, and Lenalidomide.

"A reservoir purging agent", includes but is not limited to auranofin, IL-7, prostratin, bryostatin, HDAC inhibitors, such as vorinostat, and Disulfiram, and the further agents described herein.

The failure of antiretroviral therapy (ART) to eradicate HIV-1 infection lies in the observation that HIV-1 remains quiescent in latent reservoirs. Latently infected resting CD4+ cells (either naive or long lived memory cells) carry transcriptionally silent HIV-1 and represent the predominant reservoir of HIV-1 infection. Other cells may also act as reservoirs (Reviewed in Alexaki et al., 2008, Curr. HIV Res. 6:388-400), such as macrophages, dendritic cells and astrocytes (where HIV-1 infection occurs via a CD4-independent mechanism). It is these latent reservoirs that represent the major challenge to eradication of HIV-1 infection. Approaches towards eradication include attempts to purge reservoirs by selective activation of latently infected cells (such as memory cells) in the presence of ART such that released virus may not infect and replicate in neighbouring cells (Richman et al., 2009, Science 323:1304-1307). Agents include histone deacetylase inhibitors, cytokines, such as IL-2 and IL-7, as well as bryostatin, the protein kinase C activator (Kovochich et al., 2011, PLoS ONE 6 (4):e18270). Therapeutic vaccines have the advantage of being able to penetrate sanctuary sites less well accessed by ART such as lymphoid tissue (Pantaleo et al., 1991, Proc. Natl. Acad. Sci. USA 88:9838-42; Fox et al., 1991, J. Infect. Dis. 164:1051-57) and the central nervous system (Alexaki et al., 2008, Curr. HIV Res. 6:388-400), that represent regions for viral persistence. This relates to therapeutic interventions targeting both the virus itself as well as HIV-associated immune activation.

A number of studies have been conducted with the aim of providing compounds that can safely and effectively be used to treat diseases associated with abnormal production of TNF-α. See, e.g., Marriott, J. B., et al, Expert Opin. Biol. Ther. (4): 1-8 (2001); G. W. Muller, et al, Journal of Medicinal Chemistry, 39(17): 3238-3240 (1996); and G. W. Muller, et al, Bioorganic & Medicinal Chemistry Letters, 8: 2669-2674 (1998). Some studies have focused on a group of compounds selected for their capacity to potently inhibit TNF-α production by LPS stimulated PBMC. L. G. Corral, et al, Ann. Rheum. Dis., 58 (suppl I): 1107-1113 (1999). These compounds, often referred to as immunomodulatory compounds, show not only potent inhibition of TNF-α, but also marked inhibition of LPS induced monocyte IL1B and IL12 production. LPS induced IL6 is also inhibited by immunomodulatory compounds, albeit partially. These compounds are potent stimulators of LPS induced IL10. Particular examples include, but are not limited to, the substituted 2-(2,6-dioxopiperidin-3-yl)phthalimides and substituted 2-(2,6-dioxopiperidin-3-yl)-1-oxoisoindoles as described in U.S. Pat. No. 6,281,230 and U.S. Pat. No. 6,316,471. Monocyte/macrophage function is part of the Innate Immune System that serves as a first line of defense against an infection. By modulating the host's monocytes and macrophages, immunomodulatory compounds can change the dynamics of the response to a viral infection, such as influenza.

Histone deacetylases (HDAC) are a class of enzymes that remove acetyl groups from N-acetylated lysines amino acid on histone proteins. Currently 18 HDACs have been identified in mammals. They have been divided into four classes based on cellular localization, function, and sequence similarity. Class I includes HDACs 1, 2, 3, and 8 which are found primarily in the nucleus. Class II HDACs (HDACs 4, 5, 6, 7 9, and 10) are found primarily in the cytoplasm but may be able to shuttle between the nucleus and the cytoplasm; class IIa comprises four HDACs (HDACs 4, 5, 7 and 9) while class IIb comprises two HDACs (HDACs 6 and 10) which are expressed only in the cytoplasm. HDAC11, which is ubiquitously expressed, shares sequence similarities with both class I and class II HDACs and represents Class IV. Class III (also called "sirtuin family") groups NAD+-dependent proteins which do not act primarily on histones.

The immunomodulatory compounds may be selected from anti-PD1 antibodies, such as MDX-1106 (Merck), THALOMID® (thalidomide), anti-PD1 antibodies, cyclophosphamide, Levamisole, lenalidomide, CC-4047 (pomalidomide), CC-11006 (Celgene), and CC-10015 (Celgene), and immunomodulatory compound described in any one of WO2007028047, WO2002059106, and WO2002094180. The immunomodulatory compound may be selected from 4-(amino)-2-(2,6-dioxo(3-piperidyl))-isoindoline-1,3-dione and 3-(4-amino-1-oxo-1,3-dihydro-isoindol-2-yl)-piperidine-2,6-dione. In particular the immunomodulatory compound is lenalidomide. The immunomodulatory compound may be enantiomerically pure. The second reservoir purging agent, such as a histone deacetylase (HDAC) inhibitor, may be selected from M344 (4-(dimethylamino)-N-[7-(hydroxyamino)-7-oxoheptyl] benzamide), chidamide (CS055/HBI-800), 4SC-202, (4SC), Resminostat (4SC), hydroxamic acids such as vorinostat (SAHA), belinostat (PXD101), LAQ824, trichostatin A and panobinostat (LBH589); benzamides such as entinostat (MS-275), CI994, and mocetinostat (MGCD0103), cyclic tetrapeptides (such as trapoxin, such as trapoxin B), and the depsipeptides, such as romidepsin (Istodax® (Celgene)), electrophilic ketones, and the aliphatic acid compounds such as phenylbutyrate, valproic acid, Oxamflatin, ITF2357 (generic givinostat), Apicidin, MC1293, CG05, and CG06; compounds that activate transcription factors including NF-KappaB, Prostratin, auranofin, bryostatin, a nontumorigenic phorbol ester, DPP (12-deoxyphorbol-13-phenylacetate), PMA, and Phorbol 12-myristate 13-acetate (PMA); Compounds that activate HIV mRNA elongation including P-TEF-b kinase and hexamethylbisacetamide (HMBA); IL-7; T-cell stimulating factors including anti-CD3/CD28–T-cell stimulating Ab's; Kinase inhibitors including Tyrphostin A, Tyrphostin B, and Tyrphostin C; PTEN (phosphatase and tensin homologue) gene inhibitors including SF1670 (Echelon Bioscience), Disulfiram (DSF), an inhibitor of acetaldehyde dehydrogenase, Protein Tyrosine Phosphatase Inhibitors including bpV(HOpic), bpV(phen), and bpV(pic) (Calbiochem; EMD Millipore), Toll-like receptors agonists including Toll-like receptor-9 (TLR9) and Toll-like receptor-7 (TLR9) agonists, quercetin, lipoic acid, sodium butyrate, TNF-alpha, PHA, Tat.

In the methods of the invention the components of the at least one HIV-specific peptide and/or the one or more further therapeutically active agents, may be administered simultaneously, sequentially or separately in any order.

Thus the invention provides a pharmaceutical composition comprising one, two or more components of the at least one HIV-specific peptide and/or the one or more further therapeutically active agents optionally in combination with one or more pharmaceutically acceptable adjuvants, diluents or carriers.

Similarly, the invention also provides a combination product comprising of components of the at least one HIV-specific peptide and/or the one or more further therapeutically active agents, wherein each of component is formulated in admixture with a pharmaceutically-acceptable adjuvant, diluent or carrier. In this aspect of the invention, the combination product may be either a single (combination) pharmaceutical formulation or a kit-of-parts. In a kit-of-parts some or all of the components may be formulated separately and may each be provided in a form that is suitable for administration in conjunction with the other(s).

The component(s) may also be provided for use, e.g. with instructions for use, in combination with one or more further component(s) as defined above.

The peptides for use in the invention may be produced synthetically using art recognised methods. Further details for the synthetic production of such peptides are found in the Examples. Alternatively the peptides may be produced recombinantly. When recombinantly producing the peptides for use in the invention by means of transformed cells, it is convenient, although far from essential, that the expression product is either exported out into the culture medium or carried on the surface of the transformed cell.

When an effective producer cell has been identified it is preferred, on the basis thereof, to establish a stable cell line which carries the vector of the invention and which expresses the nucleic acid fragment of the invention. Preferably, this stable cell line secretes or carries the peptide expression product, thereby facilitating purification thereof.

In general, plasmid vectors containing replicon and control sequences which are derived from species compatible with the host cell are used in connection with the hosts. The vector ordinarily carries a replication site, as well as marking sequences which are capable of providing phenotypic selection in transformed cells. For example, E. coli is typically transformed using pBR322, a plasmid derived from an E. coli species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the prokaryotic microorganism for expression.

Those promoters most commonly used in recombinant DNA construction include the β-lactamase (penicillinase) and lactose promoter systems (Chang et al., 1978; Itakura et al., 1977; Goeddel et al., 1979) and a tryptophan (trp) promoter system (Goeddel et al., 1979; EP-A-0 036 776). While these are the most commonly used, other microbial promoters have been discovered and utilized, and details concerning their nucleotide sequences have been published.

In addition to prokaryotes, eukaryotic microbes, such as yeast cultures may also be used, and also here the promoter should be capable of driving expression. *Saccharomyces cerevisiae*, or common baker's yeast is the most commonly used among eukaryotic microorganisms, although a number of other strains are commonly available. For expression in *Saccharomyces*, the plasmid YRp7, for example, is commonly used (Stinchcomb et al., 1979; Kingsman et al., 1979; Tschemper et al., 1980).

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also incorporated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. Examples of such useful host cell lines are VERO and HeLa cells, Chinese hamster ovary (CHO) cell lines, and W138, BHK, COS-7 293, *Spodoptera frugiperda* (SF) cells, *Drosophila melanogaster* cell lines (such as Schneider 2 ($S_2$)), and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., other Polyoma viruses, Adeno, VSV, BPV) or may be provided by the host cell chromosomal re-application mechanism. If the vector is integrated into the host cell chromosome, the latter is often sufficient.

As for routes of administration and administration schemes of polypeptide based vaccines which have been detailed above, these are also applicable for the nucleic acid vaccines of the invention and all discussions above pertaining to routes of administration and administration schemes for polypeptides apply mutatis mutandis to nucleic acids. To this should be added that nucleic acid vaccines can also be administered intravenously and intraarterially. Furthermore, it is well-known in the art that nucleic acid vaccines can be administered by use of a so-called gene gun and/or by use of electroporation, and hence also these and equivalent modes of administration are regarded as part of the present invention.

Under normal circumstances, the nucleic acid fragment is introduced in the form of a vector wherein expression is under control of a viral promoter. For more detailed discussions of vectors according to the invention, cf. the discussion above. Also, detailed disclosures relating to the formulation and use of nucleic acid vaccines are available, cf. Donnelly J J et al, 1997, Annu. Rev. Immunol. 15: 617-648 and Donnelly J J et al., 1997, Life Sciences 60: 163-172. Both of these references are incorporated by reference herein.

An alternative of using peptide immunogens or nucleic acid immunogens is the use of live immunogen technology. This entails administering a non-pathogenic microorganism which has been transformed with a nucleic acid fragment or a vector of the present invention. The non-pathogenic microorganism can be any suitable attenuated bacterial strain (attenuated by means of passaging or by means of removal of pathogenic expression products by recombinant DNA technology), e.g. *Mycobacterium bovis* BCG., non-pathogenic *Streptococcus* spp., *E. coli, Salmonella* spp., *Vibrio cholerae, Shigella*, etc. Reviews dealing with preparation of state-of-the-art live vaccines can e.g. be found in Saliou P, 1995, Rev. Prat. 45: 1492-1496 and Walker P D, 1992, Vaccine 10: 977-990, both incorporated by reference herein. For details about the nucleic acid fragments and vectors used in such live vaccines, cf. the discussion below.

As an alternative to bacterial live immunogens, the nucleic acid fragment of the invention can be incorporated in a non-virulent viral vaccine vector such as a vaccinia strain or any other suitable poxvirus.

Normally, the non-pathogenic microorganism or virus is administered only once to a subject, but in certain cases it may be necessary to administer the microorganism/virus more than once in a lifetime in order to maintain protective immunity. It is even contemplated that immunization schemes as those detailed above for polypeptide vaccination will be useful when using live or virus vaccines.

Alternatively, live or virus immunization is combined with previous or subsequent polypeptide and/or nucleic acid immunization. For instance, it is possible to effect primary immunization with a live or virus vaccine followed by subsequent booster immunizations using the polypeptide or nucleic acid approach.

PREAMBLE TO EXAMPLES

Overview Sequences and Abbreviations:
C5-Sequences:

```
                                     (SEQ ID NO: 1)
APTKAKRRVVQREKRAV (SEQ ID NO: 2)
APTKAKRRVVEREKRAV (SEQ ID NO: 3)
APTRAKRRVVQREKRAV (SEQ ID NO: 4)
APTRAKRRVVEREKRAV (SEQ ID NO: 5)
APTEAKRRVVEREKRAV (SEQ ID NO: 44)
WWGCAKRRVCGGAKRRVVQREKRA
```

(underlined amino acid residues in SEQ ID NO: 44 are linked via a disulphide linker; the N-terminal W is preferably a D-amino acid and the C-terminal A may be amidated; the peptide is termed BI450-AdjBT_1, when having these two modifications).

C5-Complex Forming Sequences:

DRPEGIEEEGGERDR (where amino acid 4 can be G and/or where amino acid 5 can be R and/or where amino acid 13 can be Q and/or where amino acid 14 can be G and/or where amino acid 15 can be K; SEQ ID NO: 6);

DRPEGIENNGGERDR (SEQ ID NO: 7 where amino acid 4 can be G and/or where amino acid 5 can be R and/or where amino acid 13 can be Q and/or where amino acid 14 can be G and/or where amino acid 15 can be K);

DRPEGIENNGGERDRDR (where amino acid 4 can be G and/or where amino acid 5 can be R and/or where amino acid 13 can be Q and/or where amino acid 14 can be G and/or where amino acid 15 can be K and/or where amino acid 16 can be G); SEQ ID NO: 46).

```
                                     (SEQ ID NO: 8)
VERYLKDQQLLG;

(SEQ ID NO: 9)
VERYLKDEELLG;

(SEQ ID NO: 10)
VERYLKDNNLLG;

(SEQ ID NO: 11)
QLLLNGSLAEEEIVI (SEQ ID NO: 12)
QLLLNGSLAEEEVVIV (SEQ ID NO: 13)
QLLLNSLAEEEVVI (SEQ ID NO: 37, also termed 204d herein)
GGAIVNGSLADDDIVI
                                     (SEQ ID NO: 45)
WWGCIEEEGCGGIEEEGGERDR:
``` underlined amino acid residues are linked via a disulphide linker; the N-terminal W is preferably a D-amino acid and the C-terminal R may be amidated; the peptide is termed BI450-AdjBT_2, when having these two modifications).

Polypeptides I:

```
Polypeptides I:
(Z-SEQ_{c5}-Z-SEQ_{c5})_n
n = 1, 2, 3, 4
```

Polypeptides II:
```
(Z-SEQ_{cx}-Z-SEQ_{cx})_n
n = 1, 2, 3, 4
```

Peptide Complexes:

```
(Z-SEQ_{c5}-Z-SEQ_{c5})_n
       |
Bis-maleimide linker
       |
(Z-SEQ_{cx}-Z-SEQ_{cx})_n
n = 1, 2, 3, 4

(Z-SEQ_{c5}-Z-SEQ_{c5})_n
       |
(Z-SEQ_{cx}-Z-SEQ_{cx})_n
n = 1, 2, 3, 4
```

Examples of Polypeptides I can be, but are not Restricted to, the Following Sequences:

```
                                     (SEQ ID NO: 14)
APTKAKRGGGAPTRAKRGGGAPTEAKR (SEQ ID NO: 15)
RVVEREKGGGAKRRVVGGGRVVQREK (SEQ ID NO: 16)
GGAKRRVVGGAKRRVVGQREKRAV (SEQ ID NO: 17)
CGGAKRRVVGGAKRRVVGQREKRAV (SEQ ID NO: 18)
GGAKRRVVGGAKRRVVGGQREKR (SEQ ID NO: 19)
CGGAKRRVVGGAKRRVVGGQREKR (SEQ ID NO: 20)
GGAKRRVVGGAKRRVV (SEQ ID NO: 21)
GCGAKRRVVGGAKRRVV
```

Examples of Polypeptides II can be, but are not Restricted to, the Following Sequences:

```
                                     (SEQ ID NO: 22)
GGGDQQLLGGAEEEIVGGIEEEGGERDRDR (SEQ ID NO: 23)
CGGGDQQLLGGAEEEIVGGIEEEGGERDRDR (SEQ ID NO: 24)
GGDQQLLGGAEEEIVGGGERDR (SEQ ID NO: 25)
CGGGDQQLLGGAEEEIVGGIEEEGG (SEQ ID NO: 26)
GGAEEEVVGGDQQLL (SEQ ID NO: 27)
CGGAEEEVVGGDQQLL
```

Examples of Disulfide Linked Constructs can be, but are not Restricted to, the Following Linked Peptide Sequences:

```
CGGAKRRVVGGAKRRVVGQREKRAV (SEQ ID NO: 28)
|
CGGGDQQLLGGAEEEIVGGIEEEGGERDRDR (SEQ ID NO: 29)

CGGAKRRVVGGAKRRVVGGQREKR (SEQ ID NO: 30)
|
```

-continued

```
CGGGDQQLLGGAEEEIVGGIEEEGG (SEQ ID NO: 31)

CGGAEEEVVGGDQQLL (SEQ ID NO: 32)
|
GCGGAKRRVVGGAKRRVV (SEQ ID NO: 33)
```

The above disulfide linked constructs may e.g. be synthesised by titration of 2-pyridinesulfenyl (SPyr)-protected cysteine-containing peptides with thiol-unprotected peptides. This has proven to be a superior procedure to selectively generate disulfide-linked peptide heterodimers preventing the formation of homodimers (Schutz A et al., Tetrahedron, Volume 56, Issue 24, 9 Jun. 2000, Pages 3889-3891). Similar constructs where SEQ ID NO: 28 is disulphide linked to SEQ ID NOs 31 or 33, or where SEQ ID NO: 30 is disulphide linked to SEQ ID NOs: 29 or 33, or where SEQ ID NO: 32 is disulphide linked to SEQ ID NOs: 29 or 31 are also within the scope of the present invention.

Examples of other linked constructs can be, but are not restricted to, the following linked peptide sequences, which have all been obtained from Bachem (UK) Ltd:

```
GAKRRVVGGCGGAKRRVVQREKRAGEREKRA (SEQ ID NO: 38)
             |
     GKGGIEEEGGRDRDRGGEQDRDR (SEQ ID NO: 39)
```

(the peptides are linked via the underlined Cys and Lys residues; the entire construct is termed BI400-B herein).

```
GAKRRVVGGCGGAKRRVVQREKRAGEREKRA (SEQ ID NO: 38)
             |
     GKGGIEEEGGERDRDRGGQDRDR (SEQ ID NO: 40)
```

(the peptides are linked via the underlined Cys and Lys residues; the entire construct is termed BI400-Bu1 herein).

```
GAKRRVVGGCGGAKRRVVEREKRAGQREKRA (SEQ ID NO: 41)
             |
     GKGGIEEEGGQDRDRGGRDRDR (SEQ ID NO: 42)
```

(the peptides are linked via the underlined Cys and Lys residues; the entire construct is termed BI400-Bu2 herein).

```
GAKRRVVGGCGGAKRRVVEREKRAGQREKRA (SEQ ID NO: 41)
             |
     GKGGIEEEGGEQDRDRGGERDRD (SEQ ID NO: 43)
```

(the peptides are linked via the underlined Cys and Lys residues; the entire construct is termed BI400-Bu3 herein).

The Cys-Lys linker is typically established in the form of an amide bond between (2-oxo-ethyl) derivatized cysteine in one peptide and lysine in the other peptide.

Similar constructs where SEQ ID NO: 38 is Cys-Lys linked to SEQ ID NOs 42 or 43, or where SEQ ID NO: 41 is Cys-Lys linked to SEQ ID NOs: 39 or 40 are also within the scope of the present invention.

Small Molecule Inhibitors:

```
DQQLL     (SEQ ID NO: 34)

AKRRVV    (SEQ ID NO: 35)

AEEEVV    (SEQ ID NO: 36)
```

SEQ ID NOs 34-36 are preferably composed partly or completely of D-amino acids.

One preferred agent capable of stabilising association of the C5 domain of HIV gp120 with the transmembrane domain of gp41 and/or with the constant C2 domain of gp120 is a compound of the following structure:

(H-Glycyl-L-alanyl-L-lysyl-L-arginyl-L-arginyl-L-valyl-L-valyl-glycyl-glycyl-L-cysteinyl(2-oxo-ethyl)-glycyl-glycyl-L-alanyl-L-lysyl-L-arginyl-L-arginyl-L-valyl-L-valyl-L-glutaminyl-L-arginyl-L-glutamyl-L-lysyl-L-arginyl-L-alanyl-glycyl-L-glutamyl-L-arginyl-L-glutamyl-L-lysyl-L-arginyl-L-alanyl-NH$_2$) (H-Glycyl-L-lysyl-glycyl-glycyl-L-isoleucyl-L-glutamyl-L-glutamyl-L-glutamyl-glycyl-glycyl-L-arginyl-L-aspartyl-L-arginyl-L-aspartyl-L-arginyl-glycyl-glycyl-L-glutaminyl-L-aspartyl-L-arginyl-L-aspartyl-L-arginyl-NH$_2$), acetate salt (amide bond between Cys(2-oxo-ethyl)$^{10}$ (A-chain) and Lys$^2$ (B-chain))

This compound may also be referred to as Vacc-C5 with the following formula:

(H-Gly-Ala-Lys-Arg-Arg-Val-Val-Gly-Gly-Cys(2-oxo-ethyl)-Gly-Gly-Ala-Lys-Arg-Arg-Val-Val-Gln-Arg-Glu-Lys-Arg-Ala-Gly-Glu-Arg-Glu-Lys-Arg-Ala-NH$_2$) (H-Gly-Lys-Gly-Gly-Ile-Glu-Glu-Glu-Gly-Gly-Arg-Asp-Arg-Asp-Arg-Gly-Gly-Gln-Asp-Arg-Asp-Arg-NH$_2$), acetate salt (amide bond between Cys(2-oxo-ethyl)$^{10}$ (A-chain) and Lys$^2$ (B-chain))

This preferred C5 compound consists of two linear peptide amide chains with 31 amino acids (A-chain) and 22 amino acids (B-chain). Each chain has a free amino group at the N-terminus and an amide group at the C-terminus. The chains are covalently linked via an amide bond between Cys(2-oxo-ethyl)$^{10}$ of the A-chain and Lys$^2$ of the B-chain. All amino acid residues except the achiral Gly are in the L-configuration.

H-Gly-Ala-Lys-Arg-Arg-Val-Val-Gly-Gly-Cys-Gly-Gly-Ala-Lys-Arg-Arg-Val-Val-Gln-Arg-Glu-Lys-Arg-Ala-Gly-Glu-Arg-Glu-Lys-Arg-Ala-NH$_2$

H-Gly-Lys-Gly-Gly-Ile-Glu-Glu-Glu-Gly-Gly-Arg-Asp-Arg-Asp-Arg-Gly-Gly-Gln-Asp-Arg-Asp-Arg-NH$_2$

The preferred C5 compound may be provided as an acetate salt. The counter ion acetate is bound in ionic form to basic groups of the peptide molecule.

HIV-Specific Peptides According to the Invention

The present invention relates to agents capable of stabilising the association of the C5 domain of HIV gp120 with the transmembrane domain of gp41 and/or with the constant C2 domain of gp120 in combination with peptides based on conserved regions of HIV gag p24, antigens in free or carrier-bound form comprising at least one of the said peptides.

The HIV-specific peptides according to the invention are originating from the four different conserved areas of the HIV-1 core protein p24 which are described above, having the properties of maintaining the uniqueness (sensitivity and specificity) of the HIV-1-epitope. Further the new peptides according to the invention possess no recognized cytotoxic T lymphocyte (CTL) antagonistic effect and shall have at least one potential CTL epitope.

The HIV-specific peptides, according to the invention, which have met the above criteria are selected from the following groups;

(SEQ ID NO: 47)
$Xaa_1$ $Xaa_2$ $Xaa_3$ $Xaa_4$ $Xaa_5$ $Xaa_6$ Ala $Xaa_8$ $Xaa_9$ Gln Thr

Pro Trp $Xaa_{14}$ $Xaa_{15}$ $Xaa_{16}$ $Xaa_{17}$ $Xaa_{18}$ Val $Xaa_{20}$;

Wherein Xaa in position 1 of the peptide derivate is Lys or Arg,
Xaa in position 2 is Ala, Gly, Ser or Arg,
Xaa in position 3 is Leu or Met,
Xaa in position 4 is Gly or Arg,
Xaa in position 5 is Pro, Thr, Val, Ser, Gln or Ala,
Xaa in position 6 is Gly, Ala, Lys, Arg, Gln or Glu,
Xaa in position 8 is Thr or Ser,
Xaa in position 9 is Leu or Ile,
Xaa in position 14 is Thr, Ser or Val,
Xaa in position 15 is Ala or Ser,
Xaa in position 16 is Cys or Ser,
Xaa in position 17 is Gln or Leu,
Xaa in position 18 is Gly, Glu or Arg, and
Xaa in position 20 is Gly or Arg;

(SEQ ID NO: 50)
$Xaa_1$ $Xaa_2$ $Xaa_3$ $Xaa_4$ $Xaa_5$ Gly Leu Asn Pro Leu

Val $[Gly]_n$ $Xaa_{12}$ $Xaa_{13}$ Tyr $Xaa_{15}$ Pro $Xaa_{17}$ $Xaa_{18}$

Ile Leu $Xaa_{21}$ $Xaa_{22}$ wherein Xaa in position 1 is Arg, Lys, Asp or none
Xaa in position 2 is Trp, Gly, Lys or Arg,
Xaa in position 3 is Ile, Leu, Val or Met
Xaa in position 4 is Ile, Val or Leu
Xaa in position 5 Leu, Met, Val or Pro
Xaa in position 12 is Arg, Lys
Xaa in position 13 is Met or Leu,
Xaa in position 15 is Ser, Cys or Gln,
Xaa in position 17 is Thr, Val, Ile, Ser or Ala,
Xaa in position 18 is Ser, Gly or Thr,
Xaa in position 21 is Asp, Glu, Cys or Gly,
Xaa in position 22 is Gly or none, and
n=0, 1, 2 or 3;

(SEQ ID NO: 55)
$Xaa_1$ $Xaa_2$ $Xaa_3$ Pro Ile Pro $Xaa_7$ $Xaa_8$ $Xaa_9$ $Xaa_{10}$ $Xaa_{11}$ $Xaa_{12}$ $[Gly]_n$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ $Xaa_{22}$ $Xaa_{23}$ $Xaa_{24}$ wherein Xaa in position 1 is Asn, Ser, Gly, His, Ala, Pro, Arg or none
Xaa in position 2 is Asn, Ala or Lys
Xaa in position 3 is Pro, Gln, Gly, Ile or Leu
Xaa in position 7 is Val or Ala
Xaa in position 8 is Gly or Lys
Xaa in position 9 is Glu, Asp, Lys, Phe or Thr
Xaa in position 10 is Ile, Met, Val or Leu
Xaa in position 11 is Tyr, Leu or none
Xaa in position 12 is Ser or none
Xaa in position 13 is Arg or none
Xaa in position 14 is Asp, Arg, Trp, Ala or none
Xaa in position 15 is Ile or none
Xaa in position 16 is Tyr or none
Xaa in position 17 is Lys or Arg
Xaa in position 18 is Arg, Lys or Asp
Xaa in position 19 is Trp or Gly
Xaa in position 20 is Ile, Met, Val, Gln or Ala
Xaa in position 21 is Ile, Val or Ala
Xaa in position 22 is Leu, Met or Val
Xaa in position 23 is Gly or Cys
Xaa in position 24 is Leu or none,
n=1, 2 or 3, and (SEQ ID NO: 61)
$Xaa_1$ $Xaa_2$ Ile Ile $Xaa_5$ $Xaa_6$ $Xaa_7$ $Xaa_8$ $Xaa_9$ Leu $Xaa_{11}$ $[Gly]_n$ $[Arg]_m$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ $Xaa_{21}$ $Xaa_{22}$ $Xaa_{23}$ $Xaa_{24}$ $Xaa_{25}$ wherein the Xaa in position 1 is Pro, Lys, Arg or none
Xaa in position 2 is Glu, Arg, Phe or Lys
Xaa in position 5 is Pro or Thr
Xaa in position 6 is Met, Thr or Nleu
Xaa in position 7 is Phe or Leu
Xaa in position 8 is Ser, Thr, Ala. or Met
Xaa in position 9 is Ala, Glu or Leu
Xaa in position 11 is Ser or none
Xaa in position 12 is Ala, Arg or none
Xaa in position 13 is Ile, Leu or none
Xaa in position 14 is Ser, Ala, Leu or none
Xaa in position 15 is Tyr, Glu or Asp
Xaa in position 16 is Gly or Asp
Xaa in position 17 is Ala or Leu
Xaa in position 18 is Thr, Ile, Val, Leu or Asn
Xaa in position 19 is Pro, Thr or Ser
Xaa in position 20 is Tyr, Phe, Nleu, His or Gln
Xaa in position 21 is Asp, Asn, Leu or Ala
Xaa in position 22 is Leu, Ile, Val or Asn
Xaa in position 23 is Asn, Tyr, Cys or Gly
Xaa in position 24 is Thr, Met, Ile, Ala, Val or none
Xaa in position 25 is Gly or none
n=1, 2 or 3 and m=0, 1, 2 or 3 independent of each other,
the terminal ends of each HIV specific peptide may be free carboxyl- or amino groups, amides, acyls, acetyls or salts thereof.

The HIV-specific peptide sequences have the potential to serve as a good antigen wherein the antigen comprises at least one peptide selected from the group of sequences of SEQ ID NO: 47, SEQ ID NO: 50, SEQ ID NO: 55 or SEQ ID NO: 61. The antigenicity may be adapted through adjusting the ratio or concentration of different peptides or size of the peptides by for instance dimerisation or polymerisation and/or immobilisation to a solid phase. The antigen comprises two or more polypeptide sequences, according to the invention, which are either linked by a bridge for instance a disulphide bridge between the Cys residues of the chains or bridges like $C_1$-$C_8$ alkylen possibly intervened by one or more heteroatoms like O, S, or N or preferably they are unlinked. The chains may be immobilized to a solid phase in monomeric, dimeric or oligomeric forms. Further amino acids may be added to the ends in order to achieve an «arm» to facilitate immobilization.

All amino acids in the HIV-specific peptides of the invention can be in both D- or L-form, although the naturally occurring L-form is preferred.

The C- and N-terminal ends of the HIV-specific peptide sequences could deviate from the natural sequences by modification of the terminal NH$_2$-group and/or COOH-group, they may for instance be acylated, acetylated, amidated or modified to provide a binding site for a carrier or another molecule.

The HIV-specific peptides according to the invention are consisting of 6 to 50 amino acids, preferably between 10 and 30 amino acids. They are covering all natural variation of amino acids in the identified positions.

The polypeptide antigen according to the invention is either in a free or in a carrier-bound form. The carrier or solid phase to which the peptide is optionally bound can be selected from a vide variety of known carriers. It should be selected with regard to the intended use of the immobilized polypeptide as a diagnostic antigen or as an immunizing component in a vaccine.

Examples of carriers that can be used for e.g. diagnostic purposes are magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatine or polysaccharide particles or other protein particles, red blood cells, mono- or polyclonal antibodies or fab fragments of such antibodies.

In a preferred embodiment of the vaccine according to the present invention it comprises antigens containing the peptides of the SEQ ID NO: 1, 4, 9 and 15, more preferred the peptides occur in the ratio 1:1:1:1.

In a further preferred embodiment the vaccine composition contains the antigens;

```
                                        (SEQ ID NO: 49)
RALGPAATLQTPWTASLGVG-NH2

(SEQ ID NO: 52)
RWLLLGLNPLVGGGRLYSPTSILG-NH2

(SEQ ID NO: 57)
RAIPIPAGTLLSGGGRAIYKRTAILG-NH2
and (SEQ ID NO: 64)
RFIIPNIFTALSGGRRALLYGATPYAIG-NH2.
(NI in position 6 is Norleucine).
```

One of the sequences contains a B-cell epitope and will activate the humoral immune system, whereas the other sequences contribute with CTL-epitopes and the amino acid changes implemented within the frame of the CTL-epitope are designed to achieve enhanced binding. Other amino acid changes have been conducted in order to facilitate the synthesis of the peptide and/or increase the solubility of the peptide.

EXAMPLE 1

Synthesis of Peptides Using Conventional Techniques for Linear Sequences

Preparation of APTKAKRRVVQREKR

The peptide was synthesized in amide form, from the corresponding starting point according to the general description of F-moc synthesis (Atherton et al. 1978 3. Chem. Soc. Chem Commun 539), which is below termed "the general description of synthesis.

Purity (HPLC): more than 90%.

Mass spectral analysis: Theoretical molecular weight: 1822.2

Experimental molecular weight: 1823.0 ES+

Preparation of APTKAKR

The peptide was synthesized in amide form, from the corresponding starting point according to the general description of synthesis.

Purity (HPLC): more than 90%.

Mass spectral analysis: Theoretical molecular weight: 769.6

Experimental molecular weight: 760.7 ES+

Preparation of APTRAKR

The peptide was synthesized in amide form, from the corresponding starting point according to the general description of synthesis.

Purity (HPLC): more than 90%.

Mass spectral analysis: Theoretical molecular weight: 797.6

Experimental molecular weight: 797.6 ES+

Preparation of APTEAKR

The peptide was synthesized in amide form, from the corresponding starting point according to the general description of synthesis.

Purity (HPLC): more than 90%.

Mass spectral analysis: Theoretical molecular weight: 770.9

Experimental molecular weight: 770.9 ES+

Preparation of RVVEREK

The peptide was synthesized in amide form, from the corresponding starting point according to the general description of synthesis.

Purity (HPLC): more than 90%.

Mass spectral analysis: Theoretical molecular weight: 914.1

Experimental molecular weight: 913.9 ES+

Preparation of RVVQREK

The peptide was synthesized in amide form, from the corresponding starting point according to the general description of synthesis.

Purity (HPLC): more than 90%.

Mass spectral analysis: Theoretical molecular weight: 913.1

Experimental molecular weight: 913.0 ES+

Preparation of AKRRVV

The peptide was synthesized in amide form, from the corresponding starting point according to the general description of synthesis.

Purity (HPLC): more than 90%.

Mass spectral analysis: Theoretical molecular weight: 726.9

Experimental molecular weight: 726.9 ES+

Preparation of DRPEGIEEEGGERDR

The peptide was synthesized in amide form, from the corresponding starting point according to the general description of synthesis.

Purity (HPLC): more than 90%.

Mass spectral analysis: Theoretical molecular weight: 1742.1

Experimental molecular weight: 1742.8

Preparation of VERYLKDQQLLG

The peptide was synthesized in amide form, from the corresponding starting point according to the general description of synthesis.

Purity (HPLC): more than 90%.

Mass spectral analysis: Theoretical molecular weight: 1460.7

Experimental molecular weight: 1460.1

Preparation of VERYLKDEELLG
The peptide was synthesized in amide form, from the corresponding starting point according to the general description of synthesis.
Purity (HPLC): more than 90%.
Mass spectral analysis: Theoretical molecular weight: 1462.6
Experimental molecular weight: 1463.0

Preparation of VERYLKDNNLLG
The peptide was synthesized in amide form, from the corresponding starting point according to the general description of synthesis.
Purity (HPLC): more than 90%.
Mass spectral analysis: Theoretical molecular weight: 1432.6

Preparation of QLLLNGSLAEEEIVI
The peptide was synthesized in amide form, from the corresponding starting point according to the general description of synthesis.
Purity (HPLC): more than 90%.
Mass spectral analysis: Theoretical molecular weight: 1639.9

Preparation of QLLLNGSLAEEEVVI
The peptide was synthesized in amide form, from the corresponding starting point according to the general description of synthesis.
Purity (HPLC): more than 90%.
Mass spectral analysis: Theoretical molecular weight: 1625.9

Preparation of QLLLNSLAEEEVVI
The peptide was synthesized in amide form, from the corresponding starting point according to the general description of synthesis.
Purity (HPLC): more than 90%.
Mass spectral analysis: Theoretical molecular weight: 1568.8

Preparation of APTKAKRGGGAPTRAKRGGGAPTEAKR
The peptide was synthesized in amide form, from the corresponding starting point according to the general description of synthesis.
Purity (HPLC): more than 90%.
Mass spectral analysis: Theoretical molecular weight: 2647.0
Experimental molecular weight: 2646.3 ES+

Preparation of RVVEREKGGGAKRRVVGGGRVVQREK
The peptide was synthesized in amide form, from the corresponding starting point according to the general description of synthesis.
Purity (HPLC): more than 90%.
Mass spectral analysis: Theoretical molecular weight: 2862.3
Experimental molecular weight: 2863.3 ES+

Preparation of GGAKRRVVGGAKRRVVGQREKRAV
The peptide was synthesized in amide form, from the corresponding starting point according to the general description of synthesis.
Purity (HPLC): more than 90%.
Mass spectral analysis: Theoretical molecular weight: 2590.1

Preparation of CGGAKRRVVGGAKRRVVGQREKRAV
The peptide was synthesized in amide form, from the corresponding starting point according to the general description of synthesis.
Purity (HPLC): more than 90%.
Mass spectral analysis: Theoretical molecular weight: 2693.2

Preparation of GGAKRRVVGGAKRRVVGGQREKR
The peptide was synthesized in amide form, from the corresponding starting point according to the general description of synthesis.
Purity (HPLC): more than 90%.
Mass spectral analysis: Theoretical molecular weight: 2476.9

Preparation of CGGAKRRVVGGAKRRVVGGQREKR
The peptide was synthesized in amide form, from the corresponding starting point according to the general description of synthesis.
Purity (HPLC): more than 90%.
Mass spectral analysis: Theoretical molecular weight: 2580.0

Preparation of GGAKRRVVGGAKRRVV
The peptide was synthesized in amide form, from the corresponding starting point according to the general description of synthesis.
Purity (HPLC): more than 90%.
Mass spectral analysis: Theoretical molecular weight: 1665.0

Preparation of GCGAKRRVVGGAKRRVV
The peptide was synthesized in amide form, from the corresponding starting point according to the general description of synthesis.
Purity (HPLC): more than 90%.
Mass spectral analysis: Theoretical molecular weight: 1768.1

Preparation of GGGDQQLLGGAEEEIVGGIEEEGGERDRDR
The peptide was synthesized in amide form, from the corresponding starting point according to the general description of synthesis.
Purity (HPLC): more than 90%.
Mass spectral analysis: Theoretical molecular weight: 3127.2

Preparation of CGGGDQQLLGGAEEEIVGGIEEEGGERDRDR
The peptide was synthesized in amide form, from the corresponding starting point according to the general description of synthesis.
Purity (HPLC): more than 90%.
Mass spectral analysis: Theoretical molecular weight: 3230.4

Preparation of GGDQQLLGGAEEEIVGGGERDR
The peptide was synthesized in amide form, from the corresponding starting point according to the general description of synthesis.
Purity (HPLC): more than 90%.
Mass spectral analysis: Theoretical molecular weight: 2242.4

Preparation of CGGGDQQLLGGAEEEIVGGIEEEGG
The peptide was synthesized in amide form, from the corresponding starting point according to the general description of synthesis.
Purity (HPLC): more than 90%.
Mass spectral analysis: Theoretical molecular weight: 2402.5

Preparation of GGAEEEVVGGDQQLL
The peptide was synthesized in amide form, from the corresponding starting point according to the general description of synthesis.
Purity (HPLC): more than 90%.
Mass spectral analysis: Theoretical molecular weight: 1499.6

Preparation of CGGAEEEVVGGDQQLL
The peptide was synthesized in amide form, from the corresponding starting point according to the general description of synthesis.
Purity (HPLC): more than 90%.
Mass spectral analysis: Theoretical molecular weight: 1602.7

EXAMPLE 2

Synthesis of Complexed Peptides
Preparation of

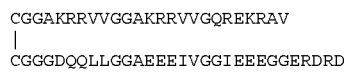

Purity (HPLC): more than 90%.
Mass spectral analysis: Theoretical molecular weight: 5750.4
Experimental molecular weight:
Preparation of

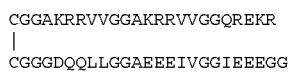

Purity (HPLC): more than 90%.
Mass spectral analysis: Theoretical molecular weight: 4965.6
Experimental molecular weight:
Preparation of

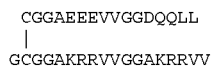

Purity (HPLC): more than 90%.
Mass spectral analysis: Theoretical molecular weight: 3410.9
Experimental molecular weight:

EXAMPLE 3

Recognition of SEQ ID NO: 1 Alone and in Combination with SEQ ID NOs: 6, 8 and 9 by Pooled Human Sera from HIV Chronically Infected Individuals, LTNP and Non-Infected Blood Donors Seroreactivity to SEQ ID NO: 1 alone or in combination with SEQ ID NOs. 6 (with the sequence DRPEGIEEEGG-ERDR), 8 and 9 was determined according to a general ELISA principle either using magnetic particles as a solid support or attachment of peptides to a 96-well tray.

Methods:
In the system described below, peptide was coated on to magnetic particles using generally accepted techniques. 300 μg was coated onto particles for all peptides with the exception of SEQ1 where 600 μg was used. SEQ ID NO: 1 (from C5) and SEQ ID NO: 6, 8 and 9 (from gp41) were preincubated overnight at 4 degrees C. to allow interactions to form between between C5 and gp41 sequences respectively and all combined. Sera were then incubated with the peptide coated beads according to established protocols. Visualisation of antibody binding to C5 peptides was achieved using protein G that can bind immunoglobulins from different species coupled to alkaline phosphatase. The positive control was commercially available serum from a sheep immunised with the C5 derived sequence APT-KAKRRVVQREKR (SEQ ID NO: 1).

Pooled sera from 25 LTNP were tested for seroreactivity to SEQ ID NO: 1 alone and SEQ ID NO: 1 when in combination with SEQ ID NOs: 6 (DRPEGIEEEGGERDR), 8 and 9 respectively and all combined. Pooled sera were also tested from 12 HIV positive, chronically infected individuals and 20 sera from blood donors. The results are shown in Table A:

TABLE A

Results of seroreactivity of pooled sera to SEQ ID NO: 1 and SEQ ID NO: 1 combined with sequences to gp41. Positivity is determined visually.

| Peptide | Blood-donors pool | HIV chronically infected pool | LTNP-pool | Pos. Control |
|---|---|---|---|---|
| APTKAKRRVVQREKR (= SEQ ID NO: 1) (600 μg/ml) | = | 2+ | 4+ | >4+ |
| APTKAKRRVVQREKE (SEQ ID NO: 1) 300 μg/ml + DRPEGIEEEGGERDR (SEQ ID NO: 6) 300 μg/ml + VERYLKDQQLLG (SEQ ID NO: 8) 300 μg/ml + VERYLKDEELLG (SEQ ID NO: 9) 300 μg/ml | (−) | Neg | 3+ | 4+ |
| APTKAKRRVVQREKE (SEQ ID NO: 1) 300 μg/ml + DRPEGIEEEGGERDR (SEQ ID NO: 6) 300 μg/ml | + | + | 2+ | 4+ |
| APTKAKRRVVQREKE (SEQ ID NO: 1) 300 μg/ml + VERYLKDQQLLG (SEQ ID NO: 8) 300 μg/ml | (−) | Neg | 2+ | 4+ |
| APTKAKRRVVQREKE (SEQ ID NO: 1) 300 μg/ml + VERYLKDEELLG (SEQ ID NO: 9) 300 μg/ml | + | Neg | + | 4+ |

Results/Discussion Points:

The results in Table A show that pooled LTNP sera generally provide strong reactivity to SEQ ID NO: 1 from HIV-1 when compared to pooled sera from patients chronically infected with HIV—this has been reported previously. However, combining SEQ ID NO: 1 with other peptides derived from gp41 (e.g. all combined or only SEQ ID NO: 8) reduced the level of background observed in blood donors as well as responses in pooled sera from chronically infected individuals. The response in LTNP remains strong.

EXAMPLE 4

Recognition of SEQ ID NO: 1 and SEQ ID NO: 1 in Combination with SEQ ID NO: 6 by Individual Human Sera from HIV Chronically Infected, LTNP, Blood Donors Seroreactivities of individual LTNP patient sera to SEQ ID NO: 1 (16 µg) alone and in combination with SEQ ID NO: 6 (16 μg) were determined using an ELISA plate as a solid support. Sheep anti-05 antibodies were used as a positive control. Optical density (OD) at 280 nm was used as a read out following the enzymatic reaction from protein G coupled to alkaline phosphatase.

Results have shown that a greater proportion of LTNP sera (n=8, 2 most right-hand, grey bars) have reactivity to SEQ ID NO: 1 when it is in combination (i.e. >80% ratio) with SEQ ID NO: 6 (DRPEGIEEEGGERDR) when compared to the reactivity against SEQ ID NO: 1 alone (n=6, most left-hand hatched bar, <0% ratio). For LTNP sera that only had a low response to SEQ ID NO: 1, this effect was enhanced when SEQ ID NOs: 1 and 6 were combined. This demonstrates that the C5:gp41 complex has the ability to capture and increase the response dramatically, even when the response from C5 alone is low; Results have shown that the OD was high in the serum samples that only showed binding to SEQ ID NO: 1. However, when combined with the gp41 sequence, the responses to C5 alone were reduced since antibodies now preferably bound the combination.

Data has been made showing the magnitude of responses in individual sera from LTNP, chronically infected patients and blood donors to SEQ ID NO: 1 alone and SEQ ID NO: 1 in combination with SEQ ID NO: 6 (DRPEGIEEEGGERDR). There was a greater response to SEQ ID NO: 1 alone and SEQ ID NO: 1 combined with SEQ ID NO: 6 (DRPEGIEEEGGERDR). among LTNP patients compared to patients chronically infected with HIV. The median OD value for binding to SEQ ID NO: 1 and SEQ ID NO: 6 in combination is higher than binding to SEQ ID NO: 1 alone for both LTNP and patients chronically infected with HIV, showing that combination with SEQ ID NO:6 improved seroreactivity. Responses in blood donors are consistently low, there is a very tight interquartile range and no difference in seroreactivity to C5 alone or in combination with SEQ ID NO: 6 (DRPEGIEEEGGERDR) in this negative control.

A Wilcoxon rank-test performed on the OD-values derived from SEQ ID NOs: 1 and 6 combined on LTNP-sera and the OD-values derived from SEQ ID NOs: 1 and 6 combined on HIV-sera, gives that the true median differs within a 25% confidence-interval.

EXAMPLE 5

Immunological Studies

Rabbit Immunizations

New Zealand White female rabbits (n=3) were immunized intradermally at weeks 0, 2 & 6 with 1 ml of BI400-B vaccine consisting of 500 μg BI400-B in 50% V/V Freund's adjuvant (i.e. Complete Freund's adjuvant used for priming, followed by boostings with Incomplete Freund's adjuvant). Individual blood serum was isolated for ELISA.

Direct ELISA for Human Sera 50-100 μl of a mixture of BI400-015 and -201 (pre-incubated in Coating buffer—0.05M $Na_2CO_3$ pH9.6; denoted CB—in cold at 16 μg/ml for each peptide 1-3 days prior to coating) or just CB (background control) was used for coating wells in microtiter plates at 4° C. overnight. The microtiter plates were then washed 3x with washing buffer (PBS+1% v/v Triton-X100; denoted WB), followed by 2 h blocking at room temperature (RT) with 200 μl/well of blocking buffer (PBS+1% w/v BSA). Plates were then washed 3x with WB, followed by 1 h incubation at 37° C. with 50-70 ul/well of added human (serial dilutions ranging from 1:1-1:250 in dilution buffer (PBS+1% v/v Triton-X100+1% w/v BSA; denoted DB)). Plates were then washed 6x with WB, followed by 1 h incubation at RT with 70 μl/well of Alkaline Phosphatase-conjugated Protein G (3 μg/ml in DB; Calbiochem 539305). Plates were then washed 6x with WB, followed by 10-60 min incubation at room temperature with 100 μl/well of 0.3% w/v of Phenophtalein monophosphate (Sigma P-5758). Plates were finally quenched by adding 100 μl/well of Quench solution (0.1M TRIS+0.1M EDTA+0.5M NaOH+0.01% w/v $NaN_3$; pH14), followed by ELISA reader (ASYS UVM 340) at 550 nm.

Competitive ELISA for Rabbit Sera after Immunization with BI400-B 50-100 μl of a mixture of BI400-015 and -201 (pre-incubated in Coating buffer—0.05M $Na_2CO_3$ pH9.6; denoted CB—in cold at 16 μg/ml for each peptide 1-3 days prior to coating) or just CB (background control) was used for coating wells in microtiter plates at 4° C. overnight. Plates were then washed 3x with washing buffer (PBS+1% v/v Triton-X100; denoted WB), followed by 2 h blocking at room temperature (RT) with 200 μl/well of blocking buffer (PBS+1% w/v BSA). Plates were then washed 3x with WB, followed by 1 h incubation at 37° C. with 60-100 μl/well of added rabbit serum samples (diluted 1:10-1:250 final concentration) preincubated together (4° C. overnight) with serial dilutions (ranging from 10-1000 μM final concentration) of 400-SEQ.B, BI400-015, BI400-201, BI400-204d, recombinant gp41 (Shin-Won Scientific, SWO 102 gp41), BI301-23 (irrelevant protein; control), no peptide (i.e. PBS; control), LTNP-sera pools (diluted 1:10 final concentration), or Blood donor sera-pools (diluted 1:10 final concentration; control). Plates were then washed 6x with WB, followed by 1 h incubation at RT with 70 μl/well of Alkaline Phosphatase-conjugated Goat-anti-Rabbit-Ig (6 μg/ml; Dako D0487). Plates were then washed 6x with WB, followed by 10-60 min incubation at RT with 100 μl/well of 0.3% w/v of Phenoftalein monophosphate (Sigma P-5758). Plates were finally quenched by adding 100 μl/well of Quench solution (0.1M TRIS+0.1M EDTA+0.5M NaOH+0.01% w/v $NaN_3$; pH14), followed by ELISA reader (ASYS UVM 340) at 550 nm.

Results

Data have been made that demonstrates that sera from rabbits immunized with the vaccine antigen 400 SEQ-B bound to peptides corresponding to C5/gp41 (015/201) in the presence of PBS. This binding could be inhibited by recombinant gp41 as well as by peptides derived from C5 (015), gp41 (201), and C2 (204d) as well as by 400-SEQ-B itself. The binding could not be inhibited using an irrelevant peptide (B301-23).

Anti-05/gp41 sera from BI400-B immunized rabbits is competitively inhibited by LTNP-sera pools, but not with BD control sera.

Also, antibodies against C5/gp41 were observed in 26/43 natural virus suppressor HIV patients with viral loads <15000 copies/ml) and in 4/15 HIV patients with viral loads above 15000 copies/ml. Furthermore, significantly (p=0.018 when using a Mann-Whitney test) higher anti-05 IgG responses (i.e. grouped with respect to OD-value measured at same serum dilution) were observed in HIV-1 patients with viral load below 15000 copies/ml (n=43) compared to patients with viral load above 15000 copies/ml (n=15).

To conclude, the results from the immunization studies with BI400-B demonstrate that it is possible to generate peptides that elicit antibody responses to C5 and gp41/C2 not only as individual components but also as complexes. The specificity of these antibody responses is confirmed in blocking studies using specific peptide antigens. Furthermore, antibodies generated to these peptides in animal models are comparable with antibodies elicited in natural HIV infection and associated with longterm nonprogression. These results show that these peptides are suitable for diagnostics as well as the development of a vaccine targeting HIV-induced immune activation. The finding that BI400-B elicits antibodies that bind to the complex between gp41 and C5, and that these antibodies compete with antisera against the same complex epitopes in LTNP HIV patients indicates that it is possible to stimulate immune responses against these epitopes and thereby induce an LTNP-like condition in patients which do not themselves raise antibodies of this type against HIV.

EXAMPLE 6

In the following, a summary of the procedures for the synthesis and purification of C5-Peptide is given. Experience is still limited which may eventually lead to improvements in the manufacture and quality of this product.

The SPPS synthesis was started with 15 mmoles (A-chain) and 30 mmoles (B-chain) of the resin. After purification of a part of the crude C5-Peptide, 16.6 g of final product were obtained.

Stage 1: Solid Phase Peptide Synthesis

The amino acid sequences of the A-chain (H-Gly-Ala-Lys-Arg-Arg-Val-Val-Gly-Gly-Cys-Gly-Gly-Ala-Lys-Arg-Arg-Val-Val-Gln-Arg-Glu-Lys-Arg-Ala-Gly-Glu-Arg-Glu-Lys-Arg-Ala-NH$_2$) and the B-chain (H-Gly-Lys-Gly-Gly-Ile-Glu-Glu-Glu-Gly-Gly-Arg-Asp-Arg-Asp-Arg-Gly-Gly-Gln-Asp-Arg-Asp-Arg-NH$_2$) are assembled by standard solid phase peptide synthesis (SPPS) using the Fmoc-strategy. (W. C. Chan and P. D. White; Solid Phase Peptide Synthesis—A Practical Approach, Oxford University Press Inc., New York, 2000, ISBN 978-0-19-963724-9)

The solid phase is transferred into an SPPS reactor and the synthesis cycle is started with the Fmoc-deprotection. Following the deprotection step, the peptide chain is elongated by the coupling of the following N-α-protected AA derivative or the dipeptide according to the amino acid sequence in the presence of suitable activating agents. To avoid the formation of long peptide sequences as by-products, a systemic acetylation of unreacted peptide chains (capping procedure) can be performed after every coupling step.

For each single step, the solvents and/or reagents are added, and the reaction mixture is stirred and then filtered to remove solvents and/or reagents from the resin. Single steps of the SPPS cycle may be repeated in case the reaction is incomplete. The SPPS cycle is repeated until the solid phase carries the complete amino acid sequence of the A-chain or the B-chain.

For the A-chain, a final Fmoc-deprotection is performed and the SPPS is completed by drying the peptide resin under reduced pressure.

The B-chain is further modified with a bromoacetyl linker at Lys$^2$. This procedure consists of selectively cleaving the side-chain protecting group of Lys$^2$ and coupling bromoacetic acid to Lys$^2$ in the presence of a suitable activating agent. If the coupling reaction is incomplete, recoupling procedures can be performed. The SPPS is then completed by drying the peptide resin under reduced pressure.

Stage 2: Cleavage from the Resin Including Cleavage of the Acid Labile Protecting Groups Cleavage of the peptides from the resin and concomitant cleavage of the acid labile protecting groups is accomplished by treatment with TFA in the presence of water. Scavengers are added as needed to trap reactive cations and to avoid alkylation of side-chain functions. After filtering off and washing the resin with TFA, the products are precipitated in IPE. They are filtered off, washed with IPE, and dried under reduced pressure.

Stage 3: Purification of the Intermediates by Preparative HPLC (TFA System)

The A-chain and the B-chain obtained in the previous stage are purified by preparative HPLC on reversed phase columns with ACN gradient elution (TFA system) and UV detection at A=220 nm.

Portions of the peptides are dissolved in water or a mixture of water and acetic acid and loaded onto the column. Subsequently, the ACN gradient of the TFA system is started. The collected fractions are checked by analytical HPLC and pooled accordingly.

Side fractions can be repurified with the TFA system. Finally, the pooled fractions with adequate purity are lyophilized.

Stage 4: Coupling of A-Chain and B-Chain

The coupling of the two peptide chains is performed by the addition of a solution of the B-chain (1 equivalent) in aqueous TFA to a solution of the A-chain (1 equivalent) in TRIS buffer (adjusted to pH 8.5 by the addition of hydrochloric acid). Additional TRIS buffer is added to maintain a pH >8 in the reaction mixture. The reaction mixture is then stirred and the reaction progress is monitored by analytical HPLC. Upon completion, the pH of the reaction mixture is lowered to approx. pH 3 by the addition of TFA.

Stage 5: Purification by Preparative HPLC (TFA System)

The C5-peptide obtained in the previous stage is purified by preparative HPLC on reversed phase columns with ACN gradient elution (TFA system) and UV detection at A=220 nm.

Portions of the C5-peptide are directly loaded onto the column. Subsequently, the ACN gradient of the TFA system is started. The collected fractions are checked by analytical HPLC and pooled accordingly.

Side fractions can be repurified with the TFA system. Finally, the pooled fractions with adequate purity are lyophilized.

Stage 6: Ion Exchange, Microfiltration, and Lyophilization

The last stage of the manufacture of C5-Peptide is the ion exchange from the TFA salt, obtained in the previous stage, into the acetate salt.

The lyophilized material from the TFA purification is dissolved in 5% acetic acid and the solution loaded onto the ion exchange resin (acetate form). The elution is performed with 5% acetic acid and checked by TLC. The product solution is filtered through a 0.2 µm membrane filter and lyophilized to yield the final product as a white to off-white material.

EXAMPLE 7

Preparation of HIV-Specific Peptides According to the Invention

Description of the Preparation of the Peptides

The peptides of the invention can be produced by any known method of producing a linear amino acid sequence, such as recombinant DNA techniques. A nucleic acid sequence which encodes a peptide of the invention or a multimer of the said peptides, is introduced into an expression vector. Suitable expression vectors are for instance plasmids, cosmids, viruses and YAC (yeast artifical chromosome) which comprise necessary control regions for replication and expression. The expression vector may be stimulated to expression in a host cell. Suitable host cells are for example bacteria, yeast cells and mammal cells. Such techniques are well known in the art and described for instance by Sambrook et al., Molecular Cloning: A Laboratory Manual, Cold Spring Harbor Laboratory Press, Cold Spring Harbor, 1989. Other well-known techniques are degradation or synthesis by coupling of one amino acid residue to the next one in liquid phase or preferably on a solid phase (resin) for instance by the so-called Merrifield synthesis. See for instance Barany and Merrifield in the Peptides, Analysis, Synthesis, Biology, Vol. 2, E. Gross and Meinhofer, Ed. (Acad.Press, N.Y., 1980), Kneib-Coronier and Mullen Int. 3. Peptide Protein Res., 30, p. 705-739 (1987) and Fields and Noble Int. J. Peptide Protein Res., 35, p. 161-214 (1990).

In case a linked or cyclic peptide is desired, the amino acid sequence is subjected to a chemical oxidation step in order to cyclize or link the two cysteine residues within one or between two peptide sequences, when the appropriate linear amino acid sequences are synthesized, see Akaji et al., Tetrahedron Letter, 33, 8, p. 1073-1076, 1992.

General Description of Synthesis

All peptide derivatives prepared in the Examples given below were synthesized on a Milligen 9050 Peptide Synthesizer using a standard program. The resin used was Tenta Gel P RAM with a theoretical loading of 0.20 meq/g (RAPP POLYMERE GmbH, Tubingen). The final product of the synthesis was dried in vacuo overnight. The peptide was then cleaved from the resin by treatment with 90% trifluoroacetic acid in the presence of ethandithiol (5%) and water (5%) as scavengers (1.5 hours at RT). Then the resin was filtered and washed on filter with additional trifluoroacetic acid (100%) (2×20 ml). The combined filtrates were evaporated in vacuo (water bath at RT) and the residue was triturated with ethyl ether (200 ml) and the precipitated product filtered off. The solid was promptly dissolved on filter with glacial acetic acid (100 ml) and added to 1.5 l of 20% acetic acid in methanol and treated with 0.1 M solution of iodine in methanol until a faint brown colour remained. Then Dowex 1×8 ion exchange in acetate form (15 g) (Bio-Rad, Richmond, Calif.) was added and the mixture filtered. The filtrate was evaporated and the residue freeze-dried from acetic acid. The product was then purified by reversed phase liquid chromatography on a column filled with Kromasil® 100-5 C8 (EKA Nobel, Surte, Sweden) in a suitable system containing acetonitrile in 0.1% trifluoroacetic acid water solution. The samples collected from the column were analyzed by analytical high performance liquid chromatography (HPLC) (Beckman System Gold, USA) equipped with a Kromasil® 100-5 C8 Column (EKA Nobel, Surte, Sweden). Fractions containing pure substance were pooled, the solvent was evaporated and the product freeze-dried from acetic acid. The final HPLC analysis was performed on final product, and the structure of the peptide was confirmed by amino acid analysis and mass spectrometry (LDI-MS).

All amino acids used during the synthesis were L-amino acids and they were protected with a fluorenylmethoxycarbonyl group at the α-amino function. The side chains were protected as follows:

Cys (Trt), Gln(Trt), Glu(OtBu), Thr(tBu).

The abbreviations, within the brackets are:

Trt=triphenylmethyl t-Bu=tert. Butyl

OtBu=tert. Butylester

The amino acid derivatives was supplied by Bachem AG, Switzerland.

EXAMPLE 8

Preparation of K A L G P G A T L Q T P W T A C Q G V G-$NH_2$(SEQ ID NO: 48).

The peptide was synthesized in amide form, from corresponding starting materials according to the general description of synthesis. The purity was determined by HPLC analysis and the structure was confirmed by amino acid analysis and mass spectrometry (LDI-MS).

Purity (HPLC): 87%

EXAMPLE 9

Preparation of R A L G P A A T L Q T P W T A S L G V G (SEQ ID NO: 49).

The peptide was synthesized in amide form, from corresponding starting materials according to the general description of synthesis. The purity was determined by HPLC analysis and the structure was confirmed by amino acid analysis and mass spectrometry (LDI-MS).

Purity (HPLC): more than 95%

Molecular weight (free base): 1966

Molecular formula: $C_{88}H_{144}O_{25}N_{26}$

EXAMPLE 10

Preparation of W I I P G L N P L V G G G K L Y S P T S I L C G-$NH_2$(SEQ ID NO: 51).

The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): 95%

Mass spectral analysis: Theoretical molecular weight: 2454.9

Experimental molecular weight: 2454.8 ES+

EXAMPLE 11

Preparation of R W L L L G L N P L V G G G R L Y S P T S I L G (SEQ ID NO: 52).

The peptide was synthesized in amide form, from the corresponding starting materials according to the general description of synthesis. The purity was determined by HPLC analysis and the structure was confirmed by amino acid analysis and mass spectrometry (LDI-MS).

Purity (HPLC): more than 95%
Molecular weight (free base): 2552
Molecular formula: $C_{119}H_{195}O_{29}N_{33}$

EXAMPLE 12

Preparation of K I L L G L N P L V G G G R L Y S P T S I L G (SEQ ID NO: 53), R L L L G L N P L V G G G R L Y S P T T I L G (SEQ ID NO: 54) and N I P I P V G D I Y G G G D I Y K R W Q A L C L (SEQ ID NO: 70). The peptides are synthesized in amide form, from the corresponding starting materials according to the general description of synthesis. The purity are determined by HPLC analysis and the structures are confirmed by amino acid analysis and mass spectrometry (LDI-MS).

EXAMPLE 13

Preparation of R N I P I P V G D I Y G G G D I Y K R W Q A L C L (SEQ ID NO: 56).
The peptide was synthesized in amide form, from the corresponding starting materials according to the general description of synthesis. The purity was determined by HPLC analysis and the structure was confirmed by amino acid analysis and mass spectrometry (LDI-MS).
Purity (HPLC): 85%
Mass spectral analysis: Theoretical molecular weight: 2817.3
Experimental molecular weight: 2813.7 ES+

EXAMPLE 14

Preparation of R A I P I P A G T L L S G G G R A I Y K R W A I L G (SEQ ID NO:57).
The peptide was synthesized in amide form, from the corresponding starting materials according to the general description of synthesis. The purity was determined by HPLC analysis and the structure was confirmed by amino acid analysis and mass spectrometry (LDI-MS).
Purity (HPLC): more than 95%
Molecular weight (free base): 2707
Molecular formula: $C_{125}H_{208}O_{29}N_{38}$

EXAMPLE 15

Preparation of A L P I P A G F I Y G G G R I Y K R W Q A L G (SEQ ID NO: 58), K I P I P V G F I G G G W I Y K R W A I L G (SEQ ID NO: 59) and K I P I P V G T L L S G G G R I Y K R W A I L G (SEQ ID NO: 60). The peptides are synthesized in amide form, from the corresponding starting materials according to the general description of synthesis. The purity are determined by HPLC analysis and the structures are confirmed by amino acid analysis and mass spectrometry (LDI-MS).

EXAMPLE 16

Preparation of K F I I P N I F S A L G G A I S Y D L N T N I L N C I (SEQ ID NO: 62).
The peptide was synthesized in amide form, from the corresponding starting materials according to the general description of synthesis. NI in the sequence is Norleucine. The purity was determined by HPLC analysis and the structure was confirmed by amino acid analysis and mass spectrometry (LDI-MS).
Purity (HPLC): more than 80%
Mass spectral analysis: Theoretical molecular weight: 2783.3
Experimental molecular weight: 2783.3 ES+

EXAMPLE 17

Preparation of K F I I P N I F S A L S G G G A I S Y D L N T F L N C I G (SEQ ID NO: 63).
The peptide was synthesized in amide form, from the corresponding starting materials according to the general description of synthesis. NI in the sequence is Norleucine. The purity was determined by HPLC analysis and the structure was confirmed by amino acid analysis and mass spectrometry (LDI-MS).
Purity (HPLC): more than 80%
Mass spectral analysis: Theoretical molecular weight: 2932.4
Experimental molecular weight: 2931.8 ES+

EXAMPLE 18

Preparation of R F I I P N I F T A L S G G R R A L L Y G A T P Y A I G (SEQ ID NO:64).
The peptide was synthesized in amide form, from the corresponding starting materials according to the general description of synthesis. NI in the sequence is Norleucine. The purity was determined by HPLC analysis and the structure was confirmed by amino acid analysis and mass spectrometry (LDI-MS).
Purity (HPLC): more than 95%
Molecular weight (free base): 2894
Molecular formula: $C_{137}H_{217}O_{32}N_{37}$

EXAMPLE 19

Preparation of K I I P N I F S A L G G G R L L Y G A T P Y A I G (SEQ ID NO: 65), R I I P N I F T A L S G G G R L L Y G A T P Y A I G (SEQ ID NO: 66) and W I I P N I F S A L G G A I S Y D L N T N I L N C I (SEQ ID NO: 71). The peptides are synthesized in amide form, from the corresponding starting materials according to the general description of synthesis. The purity are determined by HPLC analysis and the structures are confirmed by amino acid analysis and mass spectrometry (LDI-MS).

EXAMPLE 20

Dimerisation Via Disulphide Bridge.
The peptide sequences of the Examples 8 and 10 were linked via an oxidation step to form a dipeptide wherein the cysteine residues formed a disulphide bridge. The bridge was formed in either ways;
A) Oxidation with $I_2$ Equal amounts of the peptides were dissolved in acetic acid/methanol (1:4) and 0.1 M $I_2$ in methanol was added yielding a mixture of the dimer.
or
B) Oxidation via [Cys(Spy)$^{16}$]-SEQ ID NO:48. 2.3 mM of the peptide of SEQ ID NO:48 dissolved in 2 M AcOH (aq) and 2-propanol (1:1) was treated with 2,2 dithiodipyridin (3 eqv) to yield [Cys(Spy)$^{16}$]-SEQ ID NO:48. Equal amounts of [Cys(Spy)$^{16}$]-SEQ ID NO:48 and peptide of SEQ ID NO:51 were dissolved in 10 mM NH$_4$Oac (aq pH=6, 5) and methanol (5:2) to yield the dimer of SEQ ID NO:67.
The purity of the peptide was determined by HPLC analysis and the peptide structure was confirmed by amino acid analysis. The peptide content (aminoacid free base) was 80%,
Purity (HPLC): 92%.

EXAMPLE 21

A vaccine comprising the peptides of the SEQ ID NO: 49, 52, 57 and 64 was prepared. The freeze-dried peptides were dissolved in sterile water at a final concentration of 4 mg/ml. The final salt concentration was 0.9%. A preparation of a granulocyte-macrophage-colony stimulating factor (GM-CSF) was also prepared, according to the manufacturers directions for use, to a final concentration of 0.3 mg/ml. The two solutions are administered intracutaneously. A typical injection dose is 100 μl.

EXAMPLE 22

An antigen solution or suspension is mixed with equal parts of Freund's adjuvant of Behring, complete or incomplete, and is then finely emulsified by being drawn up into, and vigorously pressed out of, an injection syringe, or with a homogenator. The emulsion should remain stable for at least 30 minutes. The antigen-adjuvant emulsions is best injected subcutaneously as a depot.

EXAMPLE 23

Toxicity studies were performed in mice and rats on the peptide composition of the vaccine in Example 22. The mouse was selected for the study to provide comparative data from a second commonly used rodent species. The test substance was a mixture of four peptides supplied as one vial containing lyophilised material for reconstitution with physiological saline, and dose levels were expressed in terms of total peptide load. The individual peptides was present in ratio 1:1:1:1 w/w giving dose levels of each peptide of 0.0075 mg/kg body weight, 0.075 mg/kg body weight and 0.75 mg/kg body weight, which are up to 500 fold the intended human dose. The test animals were divided into four groups of ten animals each (five males and five females); a saline control group and groups for low, intermediate and high doses. The test composition was administered once, by intravenous infusion into a tail vein at a dose rate of 3 ml/minute. The animals were killed at day 15 and 16 by intraperitoneal injection of sodium pentobarbitone.

The results of these studies indicated that the dose levels administered to the mice and rats elicited no adverse reactions and that the no effect level was in excess of 3 mg/kg.

EXAMPLE 24

Immunoassay for Detection of Antibodies Induced by HIV-1.

The magnetic particle reagents are to be prepared according to the manufacturers recommended protocol. Dynal AS, is the manufacturer of the Dynabeads, which are employed. The magnetic particles coated with ligand are called Reagent 1. A peptide according to the invention is covalently coupled to the pre-activated surface of the magnetic particles. It is also possible to physically absorb the peptide to the surface of the magnetic particles. The concentration of particles in Reagent 1 is within the range from 1 mg/ml to 15 mg/ml. The particle size varies between 0.2 μm to 15 μm. The concentration of peptides is within the range from 0.01 mg/mg particle to 1 mg/mg particle.

The anti human Ig Alkaline Phosphatase (AP) conjugated antibody reagent is prepared according to the recommended protocol of Dako AS. This protocol is a standard procedure in this field. This reagent is called Reagent 2.

The substrate solution phenolphtalein-monophosphate is to be prepared according to the recommended protocol of Fluka AG. This protocol is a standard procedure in this field. The substrate solution is called Reagent 3.

The washing and incubation buffer which is used is standard 0.05M tris-base buffer with the following additional compounds; Tween 20 (0.01% to 0.1%), glycerol (0.1% to 10%) and sodium chloride (0.2% to 0.1%).

The assay procedure comprises an incubation step wherein 1 drop of Reagent 1 is mixed with 2 drops of washing buffer in each well. After mixing, 30 μl of sample is added and the solution is incubated for 5 minutes. The magnetic particles can be trapped by a magnet and the liquid removed, before the magnet is separated. Then the wells are washed twice in 4 drops of washing solution, before incubation with Reagent 2. 1 drop of Reagent 2 is added with 2 drops of washing buffer and the solution is incubated for 5 minutes. The magnetic particles can be trapped by a magnet and the liquid removed, before the magnet is separated. Then the washing step is repeated before incubation with Reagent 3. 2 drops of Reagent 3 is added to each well and the solution is incubated for 3 minutes. The results can be read against a white background. Positive results are red (3+=strong red) whereas negative results are clearly light yellow/brown solutions as obtained in the negative control.

The immunoassay kit could be used in detection of antibodies, induced either by HIV virus or HIV-specific peptides or proteins, for instance the peptides of the present invention.

The above Examples are only meant as illustrating the invention. It must be understood that a person skilled in the art can modify the peptides, antigens and vaccines herein described without deviating from the concept and scope of this invention as set forth in the claims.

The polypeptides of the invention can be used in a combination of at least one peptide selected from each group of sequences, SEQ ID NOs: 47, 50, 55 and 61 to form antigens and the the active principle of a prophylactic or therapeutic vaccine intended to provide protection against the human immunodeficiency virus type 1 (HIV-1). The vaccine may include compounds having beneficial effects in protecting or stimulating the host's immune system (human being or vertebrate animal) for instance interleukins, interferons, granulocyte macrophage growth factors, haematopoietic growth factors or similar. Preferably the vaccine composition further contain an adjuvant or vehicle, more preferably the adjuvant or vehicle is Monophosphoryl Lipid A (MPL®) possibly with alum, Freund's adjuvant (complete or incomplete) or aluminum hydroxide. The optimal amount of adjuvant/vehicle will depend on the type(s) which is chosen.

The peptide or vaccine formulation can be freeze-dried prior to storage. The vaccine may be stored preferably at low temperature, in ampoules containing one or more dosage units, ready for use. A typical dosage unit of the peptide according to the invention is within the concentration range: 1 μg-1 mg per kg bodyweight, preferably within 2 μg-0.15 mg per kg body weight. Persons skilled in the art will appreciate that a suitable dose will depend on the body weight of the patient, the type of disease, severity of condition, administration route and several other factors. The vaccine might be administered up to twelve times and through injection, typically it will be administered about three times. In preparation of an injection solution the peptides are dissolved in sterile sodium chloride solution at a final concentration of 1 mg/ml per peptide and 0.9% sodium chloride. Typically an injection volume is 100 μl to 200 μl (2×100 μl). The peptide is preferably co-administered with a suitable adjuvant and/or a granulocyte-macrophage growth factor for instance Leucomax® <<Shering Plough>>. Suitable administration may be intracutane, subcutane, intravenous, peroral, intramuscular, intranasal, mucosal or any other suitable route. Booster administrations may be required in order to maintain protection.

EXAMPLE 25

The anti-HIV p24 immune response resulting from Vacc-4x immunization could in combination with ART potentially improve immune reconstitution in patients who have not fully regained a healthy CD4 level (>600×10$^6$/L). Potential benefits of Vacc-4x in subjects with incomplete immune reconstitution include a possible sustained improvement in the immune response to p24 and HIV.

Potential risks include the discomfort and inconvenience associated with the immunizations and the risk of known or unknown side effects of exposure to Vacc-4x and Leukine (rhu-GM-CSF) including, most commonly, local reactions at the site of injections and fatigue (likelihood not yet determined).

The results of non-clinical single-dose studies in mice and rats indicate that the dose levels of intravenous Vacc-4x elicited no adverse reactions and that the no effect level was in excess of 3 mg/kg.

In a rabbit study the effect of Vacc-4x was evaluated in the presence of concomitant GM-CSF, the adjuvant used in the clinical program. Local intradermal reactions such as erythema and edema were noted, however, similar effects were noted in control animals both macroscopically and histological. These local reactions were slightly more pronounced in the Vacc-4x treated animals. There were no systemic reactions in this study. These data indicate that Vacc-4x has no limiting toxicology in a model that is relevant to the proposed clinical study.

The therapeutic vaccine candidate Vacc-4x, has been studies in a Phase I and three Phase II clinical studies. The Phase I study enrolled 11 HIV-positive subjects, including nine subjects on ART. Subjects were maintained on ART (if entered on ART); all subjects were treated with 12 immunizations of Vacc-4x at a dose of 0.4 mg/injection over a period of 26 weeks. Immunizations were performed following injection of rhu-GM-CSF (Leucomax® [molgramostim]) as adjuvant. All subjects experienced one or more adverse events (AEs); nine subjects experienced events judged related to treatment. The adverse reactions reported were mild or moderate in severity except for severe local reactions in one subject. No subjects were withdrawn due to treatment-related AEs or toxicological reactions; no serious adverse events (SAEs) occurred. Treatment related events observed in more than one subject included painful injection (seven subjects), fatigue-vertigo (four subjects), influenza-like symptoms (two subjects), and irritated skin at injection site (two subjects).

All subjects experienced a cell-mediated immune response, measured by delayed-type hypersensitivity (DTH) skin reaction. Some cell-mediated immune response, measured by γ IFN release using enzyme-linked immunosorbent spot assay (ELISPOT), was reported for 45% of the subjects; no antibody response to Vacc-4x peptides was observed.

The Phase II dose-finding study (CTN B-HIV 2/2001) enrolled 40 HIV positive subjects, of which 38 completed the trial. Subjects were maintained on ART and treated with 10 immunizations at a dose of 0.4 mg (20 subjects) or 1.2 mg (20 subjects) per Vacc 4x injection, over a period of 26 weeks. Immunizations with Vacc 4x were performed following injection of rhu-GM-CSF (Leucomax [molgramostim]) as a local adjuvant. ART was interrupted from Week 26 to Week 30 to allow exposure to the subject's own virus (autologous immunization). ART was resumed from Week 30 to Week 38 to allow maturation of immune responses to the Vacc 4x peptides and to the subject's own virus. ART was discontinued from Week 38 to Week 52 when the study was formally concluded. Treatment-related AEs were observed in 20 subjects (8 subjects in the 0.4 mg group and 12 subjects in the 1.2 mg group). No SAEs were reported during the period of immunization. One subject experienced a transient vasovagal reaction in conjunction with immunization and the DTH test at Week 26 and Week 38. A second subject experienced a vasovagal reaction in conjunction with the DTH test at Week 52. For the laboratory parameters, vital signs, and performance status, no changes attributable to immunization were observed. Changes in HIV RNA, CD4 cell counts, and CD8 cell counts showed no safety concerns related to immunization.

Immunological responses reported as DTH positive reactions were observed for all subjects. Overall, positive responses both for induration and erythema were statistically significantly higher in the high dose (HD, 1.2 mg Vacc-4x) group compared to the low dose (LD, 0.4 mg Vacc 4x) group. The dose-dependent differences in DTH reactions were maintained throughout the study. T-cell proliferation appeared stable after Week 12 and demonstrated an HD advantage, consistent with the DTH results. ART was interrupted at Week 38 with planned restart when CD4 counts fell to less than 200/μL or when AIDS- or HIV related events were observed (i.e. clinical practice). DTH responses to Vacc-4x (high versus low response determined at Week 38) were associated with reduced viral loads and correspondingly improved CD4 counts at the end of the study (Week 52).

During the immunization period, CD4 counts were stable or increased. Interruption of ART resulted in reduction of CD4 counts. However, 14 weeks after the last interruption of ART (Week 52), the mean CD4 counts were still above 200×106 cells/L. No difference between the LD and the HD groups was observed. The majority of subjects remained off ART following completion of the study (Week 52); permission was given to follow the subjects until they resumed ART. The duration of treatment interruption was linked to immune responsiveness to the peptides. When subjects were compared to similar subjects in the Netherlands that had stopped treatment without Vacc-4x administration, a significantly slower decline in CD4 cells was noted for the Vacc-4x subjects. The median treatment interruption achieved for all the subjects that participated in the Vacc-4x Phase II clinical study was 31 months.

CTN BI Vacc-4x/2009/1 was an open-label follow-up of study CTN B-HIV-2/2001 to determine whether a re-boost with Vacc-4x could reactivate or increase the immune response obtained during the immunization performed in the CTN B-HIV-2/2001 study. The secondary objectives were to evaluate: the in vivo immunogenicity of Vacc-4x by evaluation of DTH and to compare the DTH response to DTH in the initial study; the effect of Vacc-4x on CD4 counts, CD8 counts and HIV viral RNA; and the safety and tolerability of Vacc-4x. All 26 subjects included in the study received two booster administrations of Vacc-4x.

A total of 74 AEs were reported by 23 subjects. Most adverse events (n=60) were scored as possibly/probably related to the study treatment. The majority (98%) of the related adverse events were mild. Two adverse events related to study treatment, one headache and one injection site indurations, were scored as moderate intensity. Itching (injection site pruritus) was the most frequent reported adverse event related to the study treatment. Nineteen patients (73%) reported this adverse event at least once. Ten of these patients reported itching related to both immunizations, while for the other nine patients it was only reported once. Five patients reported swelling related to the immunization. For three of these patients swelling was reported after both immunizations. No patient died during the study. No patient reported serious adverse events and no clinically relevant changes were recorded.

The study demonstrated that Vacc-4x peptides induced T cell responses lasting up to seven years. By re-boosting it was possible to increase killing markers, this again indicates that T cells had increased their potential to kill HIV-infected cells. Before re-boosting, all the patients had returned to CD4, CD8 and viral load levels that were similar to those before ART was stopped in the main study. Re-boosting had no negative effect on the CD4, CD8 and viral load of the patients. No safety concern was reported as a result of the re-boost of these patients.

The Phase II Study CT-BI Vacc-4x 2007/1 (EudraCT Number 2007-006302-13) was performed in US and Europe (UK, Germany, Spain and Italy). The study was a randomized, double-blind, multicenter, immunogenicity study of Vacc-4x versus placebo in patients infected with HIV-1 who have maintained an adequate response to ART. The primary objective was to evaluate the effect of Vacc-4x immunizations versus placebo on CD4 counts, T-cell function (ELISPOT, T-cell proliferative responses and intracellular cytokine staining) and the response to interruption of ART. The necessity to resume ART between the interruption of ART at Week 28 and the end of the study at Week 52, due to decreased CD4 count or increased viral loads, was monitored as one of the primary efficacy endpoints.

In the ITT analysis population, it was concluded that Vacc-4x did not reduce the proportion of subjects requiring resumption of ART after ART cessation at Week 28 in comparison with placebo. There was also no effect compared with placebo on the percentage change in CD4 count between Week 28 and the last CD4 assessment before resumption of ART. The time to restarting ART was similar in Vacc-4x and placebo-treated subjects.

The viral load results after ART cessation varied between subjects with evidence of favourable effects of Vacc-4x immunization over placebo. There were no significant differences in the repeated measures ANOVA for viral load over Weeks 4 to 52 when data included all evaluable subjects, irrespective of whether they were or were not taking ART. In the subgroup of subjects who remained off ART until Week 52, the average viral load was lower in the Vacc-4x-treated subjects than the placebo group. A post-hoc analysis showed the Week 52 (Last Observation Carried Forward [LOCF]) viral load to be statistically significantly lower in the Vacc-4x group than the placebo group.

The analysis of change in HIV-1 RNA from Week 28 through to Week 52 revealed a statistically significant difference between groups in favour of Vacc-4x. The AUC in those who remained off ART at Week 52 was lower in the Vacc-4x group than in the placebo group. A post-hoc analysis showed this difference in AUC to be statistically significant.

No safety concern was raised during this study. The study was supervised by a Data Safety Monitoring Board (DSMB).

EXAMPLE 26

Test of Peptides Together with IMiDs for Increased Proliferation, Polyfunctionality, IL-2 Secretion and IFN-γ Production.

Expansion of polyfunctional HIV-specific T-cells upon stimulation with Dendritic Cells, pre-incubated with peptides to be used according to the invention, may be studied by methods described by Keersmaecker et al. (J. Virol., 2012 86:9351-9360) and referenced therein, HIV proteins Gag or Nef, they are incubated with peptides to be used according to the invention, before they are used to stimulate T-cells in a co-culture.

Keersmaecker et al. found that the presence of IMiDs (Lenalidomide (IMiD3; CC-5013) and pomalidomide (IMiD1; CC-4047) during in vitro T-cell stimulation with dendritic cells presenting Gag- or Nef-specific peptides, resulted in a number of improvements in the function of the T-cells. Among these were; polyfunctional HIV specific CD8+ T cells with enhanced lytic capacity, more Gag antigen epitopes recognized and at lower antigen peptide concentrations, reduced proliferation of CD4+ T cells with increased number of polyfunctional CD4+ T-cells, increased IL-2 production by CD8 T-cells, detectable IFN-γ production by CD8+ T-cells and CD4 T-cells after antigen stimulation.

"*Expansion of Polyfunctional HIV-Specific T Cells upon Stimulation with mRNA Electroporated Dendritic Cells in the Presence of Immunomodulatory Drugs*"

Brenda De Keersmaecker, Sabine D. Allard, Patrick Lacor, Rik Schots, Kris Thielemans, and Joeri L. Aerts J. Virol. September 2012 86:9351-9360; published ahead of print 20 Jun. 2012, doi:10.1128/JVI.00472-12

EXAMPLE 27

Suggested Clinical Study Protocol for the Test of Peptide Composition Comprising 4 Peptides in Combination with Lenalidomide and HDAC Inhibitor Immunizations (four primary immunizations and two booster immunizations) at Weeks 1, 2, 3 and 4, and booster immunizations at Weeks 12 and 13 with either:

1) Peptide composition with GM-CSF as adjuvant and Lenalidomide (CC-5013), or
2) Peptide composition with GM-CSF as adjuvant and Placebo for Lenalidomide (CC-5013).
3) Placebo Suggested Doses:

Peptide composition: 0.6, 0.9, 1.2 and 1.5 mg (Equal amount of each peptide, ratio of 1:1:1:1 w/w)

Lenalidomide: 5.10, and 25 mg.

Subjects randomized to the Lenalidomide (CC-5013) arm will take a single oral dose of Lenalidomide (CC-5013) daily the two preceding days before immunization with the Peptide composition and on the day of each immunization.

The Peptide composition used according to this clinical trial setup consists of SEQ ID NO:49, SEQ ID NO:52, SEQ ID NO:57, and SEQ ID NO:64.

At week 20 subjects in all study arms will receive 20 mg panobinostat (LBH589) orally on days 1, 3, and 5 (i.e. 3 times a week) every other week for a period of 8 weeks (up to week 28) while maintaining background ART. This will be followed by a 24 week follow up period (up to week 52). Upon completion of the study, subjects may be invited to participate in an additional observational study in which ART will be interrupted to evaluate the effect of study treatment on virological control. Enrolment into this part of the study will be optional and determined by the effect of study treatments on the latent HIV-1 reservoir. (Maximum duration of treatment interruption: 16 weeks).

In Summary:
Study arm 1: Peptide composition+IMiD+HDAC (panobinostat)
Study arm 2: Peptide composition+HDAC (panobinostat)
Study arm 3: HDAC (panobinostat)

Depletion of the viral reservoir as a result of the combination treatments according to the present invention may be quantified by for instance following the procedures set forth in Lehrman et al. (The Lancet (366), 2005, pp. 549-555) and references there in. In brief, this includes measuring in samples of patient blood obtained before, during and after treatment; p24 expression from stimulated latently infected cells, plasma HIV RNA concentration (viral load), and integrated HIV DNA by realtime PCR analysis.

EXAMPLE 28

Dc/T-Cell Proliferation Assay

Dendritic cells (DC) were generated from monocytes isolated from buffy coat preparations from healthy blood donors. Briefly, peripheral blood mononuclear cells were separated by a density gradient centrifugation and the monocytes were then negatively isolated using the Dynabeads Untouched Human Monocytes (Invitrogen, Carlsbad, Calif.) following the manufacturer's instructions. The monocytes were cultured with IL-4 (20 ng/ml; Immunotools, Friesoythe; Germany) and GM-CSF (100 ng/ml; Immunotools) in X-VIVO15 medium (Lonza, Basel, Switerland) for 5-6 days to generate immature DC. Cytokines were replenished every 2-3 days. The maturation of the cells was performed for 24 hours with IFN-γ (1000 IU/ml), TNF-α (50 ng/ml), IL-1β (25 ng/ml) IFN-α (3000 IU/ml). After maturation, the DC were pulsed for 2 hours at 37° C. with peptides at 10 µg/ml, before extensive washing and co-culture with Peripheral blood mononuclear cells (PBMC) labelled with a fluorescent dye (VPD450, BD biosciences, Sam Jose, Calif.). Various ratios with DC:T cell were tested alongside with appropriate controls. IL-2 (50 U/ml) and IL-7 (50 ng/mL) (Both, Immunotools) and wells with or without IMiDs were added at the start of co-culture. At day 6-10, the level of T cell proliferation was analysed by flow cytometry. The supernatants from the co-culture wells were investigated with Luminex technology to establish any suppressor activity.

EXAMPLE 29

The peptides according to the invention used in the following examples were synthesized by Schafer-N as c-terminal amides using the Fmoc-strategy of Sheppard, (1978) J. Chem. Soc., Chem. Commun., 539.

Cell Penetration Assay

Intracellular Staining for Biotinylated Peptides 96-well U-bottom polystyrene plates (NUNC, cat no: 163320) were used for staining of human PBMCs. Briefly, 8 ul of N- or C-terminally biotinylated peptides according to the invention (i.e. 5 mM, 2.5 mM & 1.25 mM tested for each peptide) were incubated at 37° C. for 2 h with 40 ul of PBMC (12.5×106 cells/ml) from blood donors. Cells were then washed 3x with 150 ul of Cellwash (BD, cat no: 349524), followed by resuspension of each cell pellet with 100 ul of Trypsin-EDTA (Sigma, cat no: T4424), then incubated at 37° C. for 5 min. Trypsinated cells were then washed 3x with 150 ul of Cellwash (BD, cat no: 349524), followed by resuspension with BD Cytofix/Cytoperm™ plus (BD, cat no: 554715), then incubated at 4° C. for 20 min according to manufacturer. Cells were then washed 2x with 150 ul PermWash (BD, cat no: 554715). Cells were then stained with Streptavidin-APC (BD, cat no: 554067) & Anti-hCD11c (eBioscience, cat no: 12-0116) according to manufacturer at 4° C. for 30 min aiming to visualize biotinylated peptides & dendritic cells, respectively. Cells were then washed 3x with 150 ul PermWash, followed by resuspension in staining buffer (BD, cat no: 554656) before flow cytometry. Dendritic cells were gated as CD11c+ events outside lymphocyte region (i.e. higher FSC & SSC signals than lymphocytes). 200 000 total cells were acquired on a FACSCanto II flow cytometer with HTS loader, and histograms for both total cells & dendritic cells with respect to peptide-fluorescence (i.e. GeoMean) were prepared.

Extracellular Staining for Biotinylated Peptides 96-well U-bottom polystyrene plates (NUNC, cat no: 163320) were used for staining of human PBMCs. Briefly, 8 ul of N- or C-terminally biotinylated peptides according to table 1 or table 2 (i.e. 5 mM, 2.5 mM & 1.25 mM tested for each peptide; all peptides manufactured by solid phase synthesis by commercial suppliers) were incubated at 37° C. for 2 h with 40 ul of PBMC (12.5×106 cells/ml) from blood donors. Cells were then washed 3x with 150 ul of Cellwash (BD, cat no: 349524), then stained with Streptavidin-APC (BD, cat no: 554067) & Anti-hCD11c (eBioscience, cat no: 12-0116) according to manufacturer at 4° C. for 30 min aiming to visualize biotinylated peptides & dendritic cells, respectively. Cells were then washed 3x with 150 ul of Cellwash (BD, cat no: 349524), followed by resuspension in staining buffer (BD, cat no: 554656) before flow cytometry. Dendritic cells were gated as CD11c+ events outside lymphocyte region (i.e. higher FSC & SSC signals than lymphocytes). 200 000 total cells were acquired on a FACSCanto II flow cytometer with HTS loader, and histograms for both total cells & dendritic cells with respect to peptide-fluorescence (i.e. GeoMean) were prepared.

It was clearly seen that the CMI peptides according to the invention had improved ability to enter the cell compared to its native counterparts The data are geomean-value of each testet peptide, as calculated by the FACS Duva software. The Geomean values by trypsinating/Cytofix/Cytoperm:

EXAMPLE 30

Positive CTL Response May Alternatively be Assayed by ELISPOT Assay.

Human IFN-Gamma Cytotoxic T-Cell (CTL) Response by ELISPOT Assay

Briefly, at day 1, PBMC samples from HCV patients were incubated in flasks (430 000 PBMCs/cm2) for 2 h at 37° C., 5% CO2 in covering amount of culture media (RPMI 1640 Fisher Scientific; Cat No. PAAE15-039 supplemented with L-Glutamine, (MedProbe Cat. No. 13E17-605E, 10% Foetal Bovine serum (FBS), Fisher Scientific Cat. No. A15-101) and Penicillin/Streptomycin, (Fisher Acientific Cat. No. P11-010) in order to allow adherence of monocytes. Non-adherent cells were isolated, washed, and frozen in 10% V/V DMSO in FBS until further usage. Adherent cells were carefully washed with culture media, followed by incubation at 37° C. until day 3 in culture media containing 2 µg/ml final concentration of hrGM-CSF (Xiamen amoytop biotech co, cat no: 3004.9090.90) & 1 µg/ml hrIL-4 (Invitrogen, Cat no: PHC0043) and optionally an immunomodulationg agent (IMiD), and this procedure was then repeated at day 6. At day 7, cultured dendritic cells (5 000-10 000 per well) were added to ELISPOT (Millipore multiscreen HTS) plates coated with 0.5 µg/well anti-human γ Interferon together with thawed autologous non-adherent cells (200 000 per well), antigen samples (1-8 ug/ml final concentration for peptide antigens; 5 ug/ml final concentration for Concanavalin A (Sigma, Cat no: C7275) or PHA (Sigma, Cat no: L2769)) & anti-Anergy antibodies (0.03-0.05 ug/ml final concentration for both anti-PD-1 (eBioscience, cat no: 16-9989-82) & anti-PD-L1 (eBioscience, cat no: 16-5983-82)). Plates were incubated overnight and spots were developed according to manufacturer. Spots were read on ELISPOT reader (CTL-ImmunoSpot® S5 UV Analyzer).

EXAMPLE 31

ELISPOT Assay

At day one, PBMC samples from blood donors were thawed, washed with warm medium and incubated in flasks (250000PBMCs/cm2) for 24 hours at 37° C., 5% CO2 in covering amount of culture media (RPMI 1640 with ultra-glutamine, Lonza, BE12-702F701; 10% Foetal Bovine serum (FBS), Fisher Scientific Cat. No. A15-101; Penicillin/Streptomycin, Fisher Scientific Cat. No. P11-010) to allow the cells to recover after thawing. At day two, the cells were added to a Falcon Microtest Tissue Culture plate, 96 well flat bottom, at 500 000 cells per well in a volume of 200 µl total medium. Parallel wells were added the indicated stimuli in duplicate and optionally an immunomodulationg agent (IMiD), or left with medium as a control for 6 days at 37° C., 5% $CO_2$. After the six days of incubation, 100 µl of the cell suspension were transferred to an ELISPOT (Millipore multiscreen HTS) plate coated with 1 µg/ml native influenza M2e protein. After a 24 hour incubation, the plate was washed four times with PBS+0.05% Tween20, and a fifth time with PBS, 200 µl/well. A mouse Anti-human IgG or IgM biotin (Southern Biotech 9040-08 and 9020-08) was diluted in PBS with 0.5% FBS and incubated for 90 minutes at 37° C. The washing was repeated as described, before 80 µl Streptavidin-Alkaline-Phosphatase (Sigma Aldrich, S289) was added each well and incubated at 60 minutes in the dark, at room temperature. The wells were then washed 2 times with PBS+0.05% Tween20 and 4 times with PBS, 200 µl/well, before the substrate, Vector Blue Alkaline Phosphatase Substrate kit III (Vector Blue, SK-5300) was added and let to develop for 7 minutes at room temperature. The reaction was stopped with running water, the plates let dry and the sport enumerated by an ELISPOT reader (CTL-ImmunoSpot® S5 UV Analyzer).

ELISA

100 µl of antigen as indicated (pre-incubated in Coating buffer—0.05M $Na_2CO_3$ pH9.6; denoted CB—in cold at 8 µg/ml 1-3 days) or just CB (background control) was used for coating wells in microtiter plates at 4° C. The microtiter plates are then washed 3x with washing buffer (PBS+1% v/v Triton-X100; denoted WB), followed by 2 h blocking at room temperature (RT) with 200 µl/well of blocking buffer (PBS+1% w/v BSA). Plates are then washed 3x with WB, followed by 1 h incubation at 37° C. with 50-70 µl/well of added human (or rabbit or sheep) sera (serial dilutions ranging from 1:5-1:250 in dilution buffer (PBS+1% v/v Triton-X100+1% w/v BSA; denoted DB)). Plates are then washed 6x with WB, followed by 1 h incubation at RT with 70 µl/well of Alkaline Phosphatase-conjugated Protein G (3 µg/ml in DB; Calbiochem 539305) or goat anti-mouse IgG biotin (1 µg/ml, Southern Biotech, 1030-08. In case of the goat anti-mouse IgG biotin, the plates were washed one extra step as described, before addition of 100 µl Streptavidin-Alkaline-Phosphatase (1 µg/ml, Sigma Aldrich, S289) and incubated 1 hour at RT. Plates are then washed 6x with WB, followed by 10-60 min incubation at room temperature with 100 µl/well of 0.3% w/v of Phenophtalein monophosphate (Sigma P-5758). Plates are finally quenched by adding 100 µl/well of Quench solution (0.1M TRIS+0.1M EDTA+0.5M NaOH+0.01% w/v $NaN_3$; pH14), followed by a measurement with a ELISA reader (ASYS UVM 340) at 550 nm. The strength of the sera, i.e. the magnitude of the humoral immune response, is then reported as the dilution of sera that result in the described Optical Density (OD) value, or the OD value at the indicated dilution of sera.

EXAMPLE 32

CLINICAL TRIAL PROTOCOL—Phase I/IIa Study to Evaluate the Effect of Therapeutic HIV-1 Immunization using Vacc-4x+rhuGM-CSF, and HIV-1 Reactivation using Romidepsin, on the Viral Reservoir in Virologically Suppressed HIV-1 Infected Adults on cART.

The primary objective is to measure the effect of treatment with Vacc-4x+rhuGM-CSF and cyclic romidepsin treatment on the HIV-1 latent reservoir in HIV-infected patients virologically suppressed on cART.

Endpoints:

Primary Endpoints:

1) Safety and tolerability evaluation as measured by adverse events (AE), adverse reactions (AR), serious adverse events (SAE), serious adverse reactions (SAR), serious unexpected adverse reactions (SUSAR)

2) Latent reservoir size measured in CD4+ T cells by:

a) HIV-1 viral outgrowth assay (HIV-1 RNA per 106 in resting memory CD4+ T cells (RUPM))

b) Integrated HIV-1 DNA (copies per 106 CD4+ T cells)

c) Total HIV-1 DNA (copies per 106 CD4+ T cells)

Secondary Endpoints PART B

1) Time to re-initiation of cART

2) Time to detectable viremia during cessation of cART

3) HIV transcription measured as cell associated unspliced HIV-1 RNA (copies per $10^6$ CD4+ T cells)

4) HIV-specific T-cell responses as measured by ELISpot, proliferation and/or intracellular cytokine staining 5) Plasma HIV-1 viral load 6) Histone H3 acetylation as measured in lymphocytes 7) T cell count and phenotype 8) Antibody titer to Vacc-4x peptides and to p24 as measured by ELISA.

An Open Phase I/IIa Study to Evaluate the Effect of Therapeutic HIV-1 Immunization using Vacc-4x+rhuGM-CSF, and HIV-1 Reactivation using Romidepsin, on the Viral Reservoir in Virologically Suppressed HIV-1 Infected Adults on cART. The study is conducted to evaluate the safety/tolerability of Vacc-4x+rhuGM-CSF as adjunctive therapy to romidepsin and to assess the impact on the latent HIV reservoir and the ability to control viral load during an Analytical Treatment Interruption (n=20, ie. 20 patients).

Target Population: Virologically suppressed (pVL <50 copies/mL) HIV-1 infected adults currently on cART.

Study Procedures/Frequency:

1. A pre-treatment phase of 4 weeks (visit 1 to visit 2) to confirm the stability of the latent HIV-1 reservoir and determine baseline HIV-1 T lymphocyte specific immunity.

2. A therapeutic HIV-1 immunization phase of 12 weeks (from visit 2 to visit 7) in which Vacc-4x will be administered together with rhuGM-CSF at visit 2, 3, 4, 5, 6 and 7 follow by a follow-up period of 2 weeks (visit 8-visit 9).

3. A viral reactivation phase of 3 weeks (visit 10-visit 12) consisting of one cycle of romidepsin infusions at a dosing of 5 mg/m2.

4. A post-treatment observation phase of ~8 weeks (visit 13-visit 14) to assess the effect of the investigational treatment on the size of the latent HIV-1 reservoir.

5. An Analytical Treatment Interruption phase of 16 weeks (from after visit 15-34).

Investigational Medicinal Products:

Vacc-4x: 1.2 mg administered intradermally at day 0, 7, 14, 21, 77 and 84 (visit 2, 3, 4, 5, 6 and 7)

rhuGM-CSF: Leukine® (Sanofi) 0.06 mg administered intradermally, 10 min prior to Vacc-4x administration, at day 0, 7, 14, 21, 77 and 84 (visit 2, 3, 4, 5, 6 and 7)

Romidepsin: Istodax® (Celgene) 5 mg/m2 administered by 3 intravenous infusion in three consecutive weeks (day 105, 112 and 119) (visit 10, 11b and 12) (corresponding to one 28 day cycle).

Trial Design:

1. A pre-treatment phase of 4 weeks (visit 1 to visit 2) to confirm the stability of the latent HIV-1 reservoir and determine baseline HIV-1 T lymphocyte specific immunity.

2. A therapeutic HIV-1 immunization phase of 12 weeks (2 to visit 7) in which Vacc-4x will be administered together with rhuGM-CSF at visit 2, 3, 4, 5, 6 and 7 followed by a follow-up period of 2 weeks (visit 8 to visit 9).

3. A viral reactivation phase of 3 weeks (visit 10 to visit 12) consisting of one cycle of romidepsin infusions at a dosing of 5 mg/m2.

4. A post-treatment observation phase of ~8 weeks (visit 13 to visit 14) to assess the effect of the romidepsin on the size of the latent HIV-1 reservoir.

5. An Analytical Treatment Interruption phase of 16 weeks (visit 15-34).

Treatment

Vacc-4x

Vacc-4x, consists of four synthetic peptides (Vacc-10 acetate, Vacc-11 acetate, Vacc-12 acetate, and Vacc-13 acetate), each corresponding to conserved domains on the HIV-1 p24 capsid protein representing the native Gag regions with residues 166-185, 252-269, 264-284, and 335-354, respectively.

Vacc-4x is manufactured in accordance with Good Manufacturing Practice (GMP) (ref. Vacc-4x IMPD). Vacc-4x is supplied as sterile vials of freeze-dried white powder. There is no additional ingredient in the product.

RhuGM-CSF (sargramostim, Leukine®, Sanofi)

Leukine® is manufactured by Sanofi and supplied by Genzyme. It is a glycoprotein of 127 amino acids characterized by three primary molecular species having molecular masses of 19,500, 16,800 and 15,500 daltons. The liquid Leukine® presentation is formulated as a sterile, preserved (1.1% benzyl alcohol), injectable solution (500 mcg/mL) in a vial.

Lyophilized Leukine® is a sterile, white, preservative-free powder (250 mcg) that requires reconstitution with 1 mL Sterile Water for Injection, USP or 1 mL Bacteriostatic Water for Injection, USP. Liquid Leukine® has a pH range of 6.7-7.7 and lyophilized Leukine® has a pH range of 7.1-7.7.

For further information refer to IB (Leukine® prescribing information).

Romidepsin (Istodax®, Celgene)

Istodax® is manufactured by Celgene Corporation. This histone deacetylase (HDAC) inhibitor is a bicyclic depsipeptide. At room temperature, romidepsin is a white powder and is described chemically as (1S,4S,7Z,10S,16E,21R)-7-ethylidene-4,21-bis(1-methylethyl)-2-oxa-12,13-dithia-5,8,20,23-tetraazabicyclo[8.7.6] tricos-16-ene-3,6,9,19,22-pentone. The empirical formula is $C_{24}H_{36}N_4O_6S_2$. Istodax® is supplied as a kit containing two vials. Istodax® (romidepsin) for injection is a sterile lyophilized white powder and is supplied in a single-use vial containing 10 mg romidepsin and 20 mg povidone, USP. Diluent for Istodax® is a sterile clear solution and is supplied in a single-use vial containing a 2-mL deliverable volume. Diluent for Istodax® contains 80% (v/v) propylene glycol, USP and 20% (v/v) dehydrated alcohol, USP.

For further information refer to IB for romidepsin.

Vacc-4x

Each dose of Vacc-4x (0.1 mL of a 12 mg/mL solution), will be administered by intradermal injections following the intradermal administration of rhuGM-CSF (Leukine®) as adjuvant. A total of 6 Vacc-4x/rhuGM-CSF immunizations (visit 3, 4, 5, 6, 7 and 8) are planned in the HIV-1 therapeutic vaccination phase.

Approximately 10 minutes before each administration of Vacc-4x, rhuGM-CSF will be administered intradermally as an adjuvant. Vacc-4x must be administered intradermally at the same site as rhuGM-CSF, superficial to the deltoid muscle and in the same arm during the course of the study.

When administering the intradermal injection, utmost care must be taken so that no material is injected subcutaneously. If administered correctly, after puncture of the skin a small bleb should appear following the injection of only a small amount of product. An injection that is too superficial should be avoided as this will result in loss of the sample volume from the injection site during injection or after withdrawal of the needle.

RhuGM-CSF

Each dose of rhuGM-CSF (0.1 mL of 0.60 mg/mL solution) will be administered as an adjuvant by intradermal injection 10 minutes prior to the intradermal administration of Vacc-4x immunizations (visit 3, 4, 5, 6, 7 and 8) during the HIV-1 therapeutic vaccination phase. rhuGM-CSF must be administered intradermally at the same site as Vacc-4x, superficial to the deltoid muscle and in the same arm during the entire course of the study.

When administering the intradermal injection, utmost care must be taken so that no material is injected subcutaneously. If administered correctly, after puncture of the skin a small bleb should appear following the injection of only a small amount of product. An injection that is too superficial should be avoided as this will result in loss of the sample volume from the injection site during injection or after withdrawal of the needle.

Romidepsin

The dose is 5 mg/m2 administered intravenously over a 4 hour period on Days 1, 8, and 15 of a 28-day cycle (visit 10, 11 and 12).

Trial Assessment:

Laboratory Assessment

Biochemistry:

Routine biochemistry includes haematology parameters (haemoglobin, total and differential leukocyte count, platelet count), ALAT, bilirubin, alkaline phosphatase, creatinine, sodium, potassium, phosphorus, magnesium, calcium, urea, albumin and CRP.

HIV Virology:

HIV-1 viral outgrowth (HIV-1 RNA per $10^6$ resting memory CD4+ T cells (RUPM)): The gold standard assay used to measure the frequency of resting CD4+ T cells carrying latent but replication competent virus is based on co-culture of highly purified resting CD4+ T cells from the patient together with PBMCs from an HIV-negative donor and is measured as infectious units per million cells (IUPM) [Finzi 1999, Chun 2007].

Integrated HIV-1 DNA (copies per $10^6$ CD4+ T cells): Within infected cells, HIV DNA can exist as linear non-integrated forms, circular forms and as an integrated provirus. In patients receiving effective cART, the majority of HIV DNA is integrated in resting latently infected CD4+ T cells. The most widely used technique to quantify the number of cells that contain integrated virus is the Alu-LTR PCR assay [Sonza 1996].

Total HIV-1 DNA (copies per $10^6$ CD4+ T cells): Total HIV DNA quantifies integrated and non-integrated DNA as well as latent and defective virus. There is a strong correlation between total HIV DNA and integrated HIV DNA in patients on cART and therefore cell-associated HIV DNA is likely to be a good surrogate marker of the total number of latently infected cells [Koelsch 2008].

Unspliced HIV-1 RNA (copies per $10^6$ CD4+ T cells): HIV transcription is measured as copies of cell-associated unspliced HIV-1 RNA/106 CD4+ T cells using digital droplet PCR Plasma HIV-1 RNA detection by NAT screen: Measured by a transcription mediated amplification (TMA)-based methodology, usually referred to as a nucleic acid test (NAT)-screen (PROCLEIX ULTRIO Plus, Genprobe).

Plasma HIV RNA, quantitative viral load: Measured by Roche VL (routine clinical assay) Histone H3 acetylation: Measured in lymphocytes using flow cytometry with intracellular cytokine stain on fresh isolated PBMCs.

T Cell count (CD4 and CD8)
Phylogenetic Analysis
Immunology:
HIV-Specific T Cell Response as Measured by ELISpot, Proliferation and/or Intracellular Cytokine Staining

EXAMPLE 33

ELISA Assay to Determine Levels of Antibodies Against HIV Envelope Glycoprotein gp120 and/or gp41

Buffers
Coating Buffer

| 3.18 g | Na$_2$CO$_3$ |
| 5.88 g | NaHCO$_3$ |
| Purified water to 1 litre, pH 7.5 | |

Buffer 1

| 8.18 g | NaCl |
| 0.201 g | KCl |
| 2.12 g | Na$_2$HPO$_4$ × 7H$_2$O |
| 0.204 g | KH$_2$PO$_4$ |
| Purified water to 1 litre | |

Blocking Buffer

| 2 L | Buffer 1 |
| 20 g | Bovine serum albumin (BSA) |
| 19 mL | 1% NaN$_3$ |
| 0.2 mL | Antifoam |
| pH 7.5 | |

Washing Buffer

| 7.948 g | NaCl |
| 0.201 g | KCl |
| 2.1 g | Na$_2$HPO$_4$ × 7H$_2$O |
| 0.2 g | KH$_2$PO$_4$ |
| 9.5 mL | 1% NaN$_3$ |
| 10.0 mL | Triton-X-100 |
| 0.1 mL | Antifoam |
| Purified water to 1 litre, pH 7.5 | |

Dilution Buffer

| 20 g | BSA |
| 19 mL | 1% NaN$_3$ |
| 0.2 mL | Antifoam |
| 20 mL | Triton-X-100 |

Buffer 1 to 2 L

Stop-Dilution Solution

| 24.23 g | Trizma Base |
| 58.45 g | EDTA |
| 40.00 g | NaOH |
| 19 mL | 1% NaN$_3$ |
| Purified water to 2 L | |

Vacc-C5:

Dimeric peptide, which consists of C5 domain of HIV gp120 with the transmembrane domain of gp41 and/or with the constant C2 domain of gp120 with the following structure:

(H-Glycyl-L-alanyl-L-lysyl-L-arginyl-L-arginyl-L-valyl-L-valyl-glycyl-glycyl-L-cysteinyl(2-oxo-ethyl)-glycyl-glycyl-L-alanyl-L-lysyl-L-arginyl-L-arginyl-L-valyl-L-valyl-L-glutaminyl-L-arginyl-L-glutamyl-L-lysyl-L-arginyl-L-alanyl-glycyl-L-glutamyl-L-arginyl-L-glutamyl-L-lysyl-L-arginyl-L-alanyl-NH$_2$) (H-Glycyl-L-lysyl-glycyl-glycyl-L-isoleucyl-L-glutamyl-L-glutamyl-L-glutamyl-glycyl-glycyl-L-arginyl-L-aspartyl-L-arginyl-L-aspartyl-L-arginyl-glycyl-glycyl-L-glutaminyl-L-aspartyl-L-arginyl-L-aspartyl-L-arginyl-NH$_2$), acetate salt (amide bond between Cys(2-oxo-ethyl)$^{10}$ (A-chain) and Lys$^2$ (B-chain))

This compound may also be referred to as:

(H-Gly-Ala-Lys-Arg-Arg-Val-Val-Gly-Gly-Cys(2-oxo-ethyl)-Gly-Gly-Ala-Lys-Arg-Arg-Val-Val-Gln-Arg-Glu-Lys-Arg-Ala-Gly-Glu-Arg-Glu-Lys-Arg-Ala-NH$_2$) (H-Gly-Lys-Gly-Gly-Ile-Glu-Glu-Glu-Gly-Gly-Arg-Asp-Arg-Asp-Arg-Gly-Gly-Gln-Asp-Arg-Asp-Arg-NH$_2$), acetate salt (amide bond between Cys(2-oxo-ethyl)$^{10}$ (A-chain) and Lys$^2$ (B-chain))

Vacc-C5 consists of two linear peptide amide chains with 31 amino acids (A-chain) and 22 amino acids (B-chain). Each chain has a free amino group at the N-terminus and an amide group at the C-terminus. The chains are covalently linked via an amide bond between Cys(2-oxo-ethyl)$^{10}$ of the A-chain and Lys$^2$ of the B-chain. All amino acid residues except the achiral Gly are in the L-configuration.

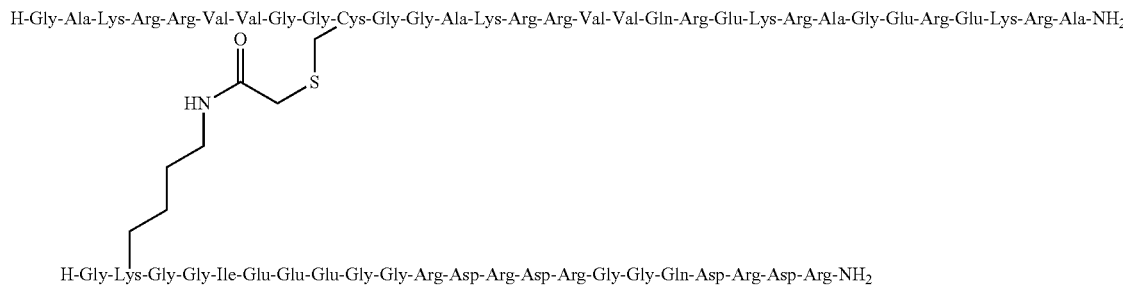

Method

ELISA plates (Nunc 249946, conical bottomed) were coated with Vacc-C5 at a final concentration of 16 µg/mL in coating buffer for 4 days at 4° C., washed three times with washing buffer (WB) and stored dried at 4° C. until required. Blocking buffer (200 µL per well) was added and the plates were incubated at room temperature for 2 hours before washing three times with WB. Serum samples were diluted using dilution buffer and stored at 2-8° C. for up to a maximum of 24 hours. Samples (100 µL) were added to the appropriate wells of the ELISA plate(s) and incubated at 37° C. for 2 hours. After washing the plates six times with WB, the bound antibody was detected using a Protein G-alkaline phosphatase conjugate (Calbiochem 539305), which binds immunoglobulin, and the substrate phenolphtalein monophosphate. The conjugate was diluted and 100 µL added to each well at a concentration of 500 µg/mL. The plates were incubated for 1 hour at room temperature before washing six times with WB. The substrate was added (100 µL per well) and incubated for 15 minutes at room temperature before colour development was stopped by the addition of stop-dilution solution. Colour changes of the substrate occur in proportion to the amount of bound serum antibody and values are reported as optical density (OD) readings taken at 550 nm/620 nm.

Each assay included a sheep anti-HIV-1 positive control serum (D7324; Aalto, Dublin, Ireland) raised against the C5 region of gp120. The concentration of anti-05 antibody in the test samples was determined by comparison to a standard curve prepared using dilutions of the positive control. As the positive control anti-05 antibodies will not be identical to the anti-C5 antibodies present in HIV-infected individuals the ELISA is regarded a semi-quantitative immunoassay. Serum samples are preferred for this assay, but plasma samples could be used with comparable results.

The samples were initially screened in duplicate at a 5x dilution and if the OD value was outside the linear part of the standard curve (i.e., OD>0.8) the plasma samples were diluted further and assayed again until an OD value within the linear range was obtained. If more than one value was within the linear range, the lowest dilution of sample (normally with an OD value of around 0.5) was used to calculate the concentration of anti-05 antibodies in the sample under test. Sera from uninfected blood donors were used to determine a cut off value for negative response of $OD_{550/620}=0.1$ (equal to three times the observed mean OD 550/620).

In order to determine the region(s) of the Vacc-C5 sequence recognised by antibodies in the plasma samples, blocking experiments were conducted. Plasma samples were diluted in the dilution buffer and incubated overnight at 2-8° C. with either 100 or 500 µM of peptide. The dilution factor used for each plasma sample was calculated to give a value in the linear range for the assay. The blocking peptides used were either complete Vacc-C5 or shorter peptide sequences from the CS region of gp120 (peptides 105, 104 and 015) or within the adjacent gp41 region (peptide 201). The amino acid sequences for the shorter peptide sequences were derived from the HIV-1 wild-type consensus sequence (www.hiv.lanl.gov). The sequences of the peptides used in the blocking assays are shown in Table 1 below and the location of the peptides within the VACC-C5 antigen is shown diagrammatically in FIG. 1.

OD values in the absence of peptide (phosphate-buffered saline (PBS) control) were taken as 100% and the percentage of blocking by each peptide calculated against this value.

Subtraction from 100 gave the % inhibition for each peptide in the sample. Negative values were set to zero.

TABLE 1

Amino acid sequences of Vacc-C5 and overlapping peptides.

| Peptide | | Sequence |
|---|---|---|
| [1]Vacc-C5 | gp120: | GAKRRVVGGCGGAKRRVVQREKRAGEREKRA |
| | gp41: | GKGGIEEEGGRDRDRGGQDRDR |
| BI400-105 | gp120: | AKRRVV |
| BI400-104 | gp120: | RVVQREK |
| BI400-015 | gp120: | APTKAKRRVVQREKR |
| BI400-201 | gp41: | DRPEGIEEEGGERDR |

[1]The two peptides contained within Vacc-C5 are linked by a thioether bond between the side-chains of the marked cysteine and lysine residues.

Results:

Patients in the Phase II Study CT-BI Vacc-4x 2007/1 (described in example 25) with high levels of pre-existing antibodies against a defined region of HIV envelope glycoprotein gp120 and/or gp41 as measured be the ELISA assay described above in this example (33) and subsequently treated with Vacc-4X had a significant lower median viral load (VL) set-point as compared to patients treated with placebo. The data indicates that the higher amount of antibodies against a specific region of HIV envelope glycoprotein gp120 and/or gp41, the lower was the median viral load set-point and the larger the difference to the group treated with placebo.

Serum samples from patients in the Phase II Study CT-BI Vacc-4x 2007/1 (N=115) at different time points (week 1, 28 and 52) were analysed for antibodies against Vacc-C5.

The effect of the level of pre-existing antibodies against Vacc-C5 at Week 1 (prior to Vacc-4x treatment and ART interruption) on median Viral Load (VL) was analyzed for 'Subgroup D' of the clinical study (LOCF population, patients that resumed ART after Week 40 that in addition had a pre-ART viral load value available). The results are summarized in Table 2. (N=71).

TABLE 2

| C5 Ab conc. | Treatment | VL set-point | | Pre-ART VL | |
|---|---|---|---|---|---|
| | | Median | Mean | Median | Mean |
| Viral load values in subgroup D and antibody cut-off at 2 µg/ml | | | | | |
| <2 µg/ml | Vacc-4x | 40050 | 71010 | 65584 | 227689 |
| | Placebo | 74425 | 86452 | 40365 | 112617 |
| >2 µg/ml | Vacc-4x | 18183 | 31711 | 48290 | 125047 |
| | Placebo | 69850 | 74428 | 42636 | 49827 |
| Viral load values in subgroup D and antibody cut-off at 5 µg/ml | | | | | |
| <5 µg/ml | Vacc-4x | 39650 | 65991 | 60470 | 209164 |
| | Placebo | 68650 | 82890 | 52940 | 110993 |
| >5 µg/ml | Vacc-4x | 9115 | 27707 | 78968 | 135710 |
| | Placebo | 107550 | 84134 | 32750 | 42792 |
| Viral load values in subgroup D and antibody cut-off at 10 µg/ml | | | | | |
| <10 µg/ml | Vacc-4x | 39650 | 63683 | 62350 | 214204 |
| | Placebo | 68650 | 79955 | 52940 | 105387 |
| >10 µg/ml | Vacc-4x | 5520 | 18723 | 49180 | 50623 |
| | Placebo | 111500 | 103550 | 32750 | 32831 |

EXAMPLE 34

Alternative ELISA Assay to Determine Levels of Antibodies Against HIV Envelope Glycoprotein Gp120 and/or Gp41, and its Application to a Comparison of Matrix Effects.

Preparation of Buffers and Working Solutions

5 M Hydrochloric Acid

Add approximately 500 mL of ultra-high purified water to a 1 liter volumetric flask. Slowly add 182.3 mL of hydrochloric acid. Make up to 1 liter with ultra-high purified water and mix gently by inversion. Store for up to 1 year at room temperature.

5 M Sodium Hydroxide

This is an exothermic reaction. Add 750 mL of ultra-high purified water to a 2 liter volumetric flask. Store this flask in a room temperature water bath. Slowly add 200 g of NaOH to the flask. During this process stir the solution with a glass rod. Allow the solution to cool down and then make up to 2 liters with ultra-high purified water and mix gently by inversion. Store for up to 1 year at room temperature.

Sodium Azide (10% w/v)

Sodium azide must be handled in a fume cupboard. Dissolve 1 g of sodium azide in water to give a final concentration of 10% sodium azide. Mix gently by inversion ensuring the sodium azide is fully dissolved. Store at 2-8° C. for up to 1 year.

Working Conjugate Solution 3.00 µg/mL

72 µL of conjugate+11,928 µL of dilution buffer. Mix gently for at least 30 minutes prior to use (using a rota-mixer).

Coating Buffer pH 9.5±0.1

Add 900 mL of water to a 1 liter volumetric flask. Then add:3.18 g of NaCO$_3$, 5.88 g of NaHCO3. Mix using a magnetic stirrer and adjust pH to 9.5±0.1 using 5 M Sodium hydroxide/5 M Hydrochloric acid solution. Make up to 1 liter with ultra-high purified water.

Blocking Buffer 20 g of BSA, 1 PBS tablet, 200 mL of water, Mix using a magnetic stirrer.

Dilution Buffer

1 PBS tablet, 2 g BSA, 2 mL Triton X100, 200 mL water. Mix using a magnetic stirrer.

Washing Buffer

5 PBS tablet, 1000 mL water, 1 mL Triton X 100. Mix using a magnetic stirrer.

Stop Solution

Add the following to a 2 liter volumetric flask: 24.23 g Trizma Base, 58.45 g EDTA, 40.00 g NaOH, 19 mL of 1% NaN$_3$, Add 1.8 liters of water. Mix using a magnetic stirrer. Make up to 2 liters using ultra-high purified water. Measure pH (acceptable value range 12-13). Expires after 1 year.

Primary Positive Control Standard Stock (2.0 mg/mL)

Reconstitute Sheep anti-HIV-1 gp120 antibody raised against the C5 region of gp120 (D7324; Aalto, Dublin, Ireland) with 1 mL of ultra-high purified water. Mix gently using a vortex mixer ensuring material has been resuspended. Centrifuge for 5 minutes at 3000 rpm. Separate the resulting supernatant into 60 µL aliquots and store at −20° C. for future use.

Secondary Positive Control Standard Stock (100 µg/mL)

50 µL of primary positive control+950 µL dilution buffer. Mix by vortex mixer. Use on day of preparation.

Working Standards

Dilute secondary stock 1:20 with dilution buffer, and then by 2:1 serial dilution (5000-78 ng/ml range).

Method

ELISA plates (Nunc 249946, conical bottomed) were coated with Vacc-C5 at a final concentration of 16 µg/mL in coating buffer for 4 days at 4° C., washed three times with washing buffer (WB) and stored dried at 4° C. until required.

Immunoassay Procedure

1. Remove from storage the number of dried plates or strips that are needed for the assay.

2. Add washing buffer 300 µL per well then aspirate. Repeat twice more (3 times in total). Aspirate the last wash and blot the plate dry by inverting over absorbent towel.

3. Add 200 µL blocking buffer to each well. Cover with plate sealer and incubate at room temperature for 2 hours, no shaking.

4. Dilute all matrix samples minimally 1 in 5 with dilution buffer (as per section 10).

5. Wash 3 times (as per step 2), with washing buffer, 300 µL per well. Remove all liquid from the wells by inverting over absorbent towel.

6. Add 100 µL of controls, standards and samples to coated plate in duplicate.

7. Cover with plate sealer and incubate at 37° C. for 2 hours in a damp box.

8. Prepare protein G/AP (working conjugate) dilution at a concentration of 3.00 μg/mL. Perform preparation at least 30 minutes prior to use.

9. Wash 6 times with washing buffer, 300 μL per well. Remove all liquid from the wells by inverting over absorbent towel.

10. Add 100 μL protein G/AP solution to each well, cover with plate sealer and incubate at room temperature for 1 hour, no shaking.

11. Wash 6 times (as per step 2) with washing buffer, 300 μL per well. Remove all liquid from the wells by inverting over absorbent towel.

12. Add 100 μL of pNPP solution to each well. Cover with plate sealer and incubate at room temperature for 15 minutes, no shaking.

13. Add 200 μL stop solution to each well. If the colour is green or does not appear uniform within the well, gently shake the plate to mix thoroughly.

14. Measure the absorbance at 405 nm, reference 540 nm.

15. Process raw data, using a 5PL (auto-estimate) algorithm, with a weighting factor of 1/Y.

Vacc-C5:

Dimeric peptide, which consists of C5 domain of HIV gp120 with the transmembrane domain of gp41 and/or with the constant C2 domain of gp120 with the following structure:

(H-Glycyl-L-alanyl-L-lysyl-L-arginyl-L-arginyl-L-valyl-L-valyl-glycyl-glycyl-L-cysteinyl(2-oxo-ethyl)-glycyl-glycyl-L-alanyl-L-lysyl-L-arginyl-L-arginyl-L-valyl-L-valyl-L-glutaminyl-L-arginyl-L-glutamyl-L-lysyl-L-arginyl-L-alanyl-glycyl-L-glutamyl-L-arginyl-L-glutamyl-L-lysyl-L-arginyl-L-alanyl-NH$_2$) (H-Glycyl-L-lysyl-glycyl-glycyl-L-isoleucyl-L-glutamyl-L-glutamyl-L-glutamyl-glycyl-glycyl-L-arginyl-L-aspartyl-L-arginyl-L-aspartyl-L-arginyl-glycyl-glycyl-L-glutaminyl-L-aspartyl-L-arginyl-L-aspartyl-L-arginyl-NH$_2$), acetate salt (amide bond between Cys(2-oxo-ethyl)$^{10}$ (A-chain) and Lys$^2$ (B-chain))

This compound may also be referred to as:

(H-Gly-Ala-Lys-Arg-Arg-Val-Val-Gly-Gly-Cys(2-oxo-ethyl)-Gly-Gly-Ala-Lys-Arg-Arg-Val-Val-Gln-Arg-Glu-Lys-Arg-Ala-Gly-Glu-Arg-Glu-Lys-Arg-Ala-NH$_2$) (H-Gly-Lys-Gly-Gly-Ile-Glu-Glu-Glu-Gly-Gly-Arg-Asp-Arg-Asp-Arg-Gly-Gly-Gln-Asp-Arg-Asp-Arg-NH$_2$), acetate salt (amide bond between Cys(2-oxo-ethyl)$^{10}$ (A-chain) and Lys$^2$ (B-chain))

Vacc-C5 consists of two linear peptide amide chains with 31 amino acids (A-chain) and 22 amino acids (B-chain). Each chain has a free amino group at the N-terminus and an amide group at the C-terminus. The chains are covalently linked via an amide bond between Cys(2-oxo-ethyl)$^{10}$ of the A-chain and Lys$^2$ of the B-chain. All amino acid residues except the achiral Gly are in the L-configuration.

H-Gly-Ala-Lys-Arg-Arg-Val-Val-Gly-Gly-Cys-Gly-Gly-Ala-Lys-Arg-Arg-Val-Val-Gln-Arg-Glu-Lys-Arg-Ala-Gly-Glu-Arg-Glu-Lys-Arg-Ala-NH$_2$

H-Gly-Lys-Gly-Gly-Ile-Glu-Glu-Glu-Gly-Gly-Arg-Asp-Arg-Asp-Arg-Gly-Gly-Gln-Asp-Arg-Asp-Arg-NH$_2$

Results

To investigate the effect of different matrices the concentrations in eight human serum samples spiked at low and ten human plasma samples spiked at low (2500 ng/mL) and high (10000 ng/mL) concentrations of either Sheep anti-HIV-1 gp120 antibody raised against the C5 region of gp120 (D7324; Aalto, Dublin, Ireland), or biobank samples with previously determined concentration. Matched unspiked samples were also analyzed to confirm absence of background. The recovery was found to be comparable between spiked serum and plasma samples (summary table below).

| Matrix | Serum (N = 8) | | | | Plasma (N = 10) | | | |
|---|---|---|---|---|---|---|---|---|
| Spike | Sheep Ab | | Biobank Sample | | Sheep Ab | | Biobank Sample | |
| Target conc. (ng/ml) | 2500 | 10000 | 2500 | 10000 | 2500 | 10000 | 2500 | 10000 |
| Mean recovery (%) | 81 | 71.8 | 80.9 | 73.6 | 82 | 80.4 | 83 | 91.8 |
| SD (%) | 18.1 | 10.7 | 21.7 | 12.4 | 16.8 | 10.9 | 4.7 | 12.8 |

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

The invention claimed is:

1. A method for reducing and/or delaying one or more pathological effects of human immunodeficiency virus I (HIV) or for reducing the risk of developing acquired immunodeficiency syndrome (AIDS) in a human infected with HIV, the method comprising the steps of:

a) measuring in a biological sample, from a human infected with HIV the amount of antibodies against one or more epitope of HIV envelope glycoproteins gp120 and/or gp41 in a suitable assay;
b) selecting a subgroup of humans from a), wherein the amount of said measured antibodies corresponds to an amount of above background level of uninfected humans;
c) treating said humans infected with HIV selected under b) with one or more peptide(s) comprising an amino acid sequence selected from SEQ ID NO:49, SEQ ID NO:52, SEQ ID NO:57 and SEQ ID NO:64 to stimulate a cell-mediated immune response and/or a peptide dimer with the structure (H-Gly-Ala-Lys-Arg-Arg-Val-Val-Gly-Gly-Cys(2-oxo-ethyl)-Gly-Gly-Ala-Lys-Arg-Arg-Val-Val-Gln-Arg-Glu-Lys-Arg-Ala-Gly-Glu-Arg-Glu-Lys-Arg-Ala-NH2) (H-Gly-Lys-Gly-Gly-Ile-Glu-Glu-Glu-Gly-Gly-Arg-Asp-Arg-Asp-Arg-Gly-Gly-Gln-Asp-Arg-Asp-Arg-NH2), acetate salt (amide bond between Cys(2-oxo-ethyl)10 (A-chain) and Lys2 (B-chain)) to stimulate a humoral response in said human.

2. The method according to claim 1, which method further comprises the administration of an immunomodulatory compound and/or a reservoir purging agent, and/or an

```
                              SEQUENCE LISTING

<160> NUMBER OF SEQ ID NOS: 71

<210> SEQ ID NO 1
<211> LENGTH: 17
<212> TYPE: PRT
<213> ORGANISM: HIV

<400> SEQUENCE: 1

Ala Pro Thr Lys Ala Lys Arg Arg Val Val Gln Arg Glu Lys Arg Ala
1               5                   10                  15

Val

<210> SEQ ID NO 2
<211> LENGTH: 17
<212> TYPE: PRT
<213> ORGANISM: HIV

<400> SEQUENCE: 2

Ala Pro Thr Lys Ala Lys Arg Arg Val Val Glu Arg Glu Lys Arg Ala
1               5                   10                  15

Val

<210> SEQ ID NO 3
<211> LENGTH: 17
<212> TYPE: PRT
<213> ORGANISM: HIV

<400> SEQUENCE: 3

Ala Pro Thr Arg Ala Lys Arg Arg Val Val Gln Arg Glu Lys Arg Ala
1               5                   10                  15

Val

<210> SEQ ID NO 4
<211> LENGTH: 17
<212> TYPE: PRT
<213> ORGANISM: HIV

<400> SEQUENCE: 4

Ala Pro Thr Arg Ala Lys Arg Arg Val Val Glu Arg Glu Lys Arg Ala
1               5                   10                  15

Val

<210> SEQ ID NO 5
<211> LENGTH: 17
<212> TYPE: PRT
<213> ORGANISM: HIV

<400> SEQUENCE: 5

Ala Pro Thr Glu Ala Lys Arg Arg Val Val Glu Arg Glu Lys Arg Ala
1               5                   10                  15

Val
```

```
<210> SEQ ID NO 6
<211> LENGTH: 15
<212> TYPE: PRT
<213> ORGANISM: HIV
<220> FEATURE:
<221> NAME/KEY: MISC_FEATURE
<222> LOCATION: (4)..(4)
<223> OTHER INFORMATION: Glu can be Gly
<220> FEATURE:
<221> NAME/KEY: MISC_FEATURE
<222> LOCATION: (5)..(5)
<223> OTHER INFORMATION: Gly can be Arg
<220> FEATURE:
<221> NAME/KEY: MISC_FEATURE
<222> LOCATION: (13)..(13)
<223> OTHER INFORMATION: Arg can be Gln
<220> FEATURE:
<221> NAME/KEY: MISC_FEATURE
<222> LOCATION: (14)..(14)
<223> OTHER INFORMATION: Asp can be Gly
<220> FEATURE:
<221> NAME/KEY: MISC_FEATURE
<222> LOCATION: (15)..(15)
<223> OTHER INFORMATION: Arg can be Lys

<400> SEQUENCE: 6

Asp Arg Pro Glu Gly Ile Glu Glu Gly Gly Glu Arg Asp Arg
1               5                   10                  15

<210> SEQ ID NO 7
<211> LENGTH: 15
<212> TYPE: PRT
<213> ORGANISM: HIV
<220> FEATURE:
<221> NAME/KEY: MISC_FEATURE
<222> LOCATION: (4)..(4)
<223> OTHER INFORMATION: Glu can be Gly
<220> FEATURE:
<221> NAME/KEY: MISC_FEATURE
<222> LOCATION: (5)..(5)
<223> OTHER INFORMATION: Gly can be Arg
<220> FEATURE:
<221> NAME/KEY: MISC_FEATURE
<222> LOCATION: (13)..(13)
<223> OTHER INFORMATION: Arg can be Gln
<220> FEATURE:
<221> NAME/KEY: MISC_FEATURE
<222> LOCATION: (14)..(14)
<223> OTHER INFORMATION: Asp can be Gly
<220> FEATURE:
<221> NAME/KEY: MISC_FEATURE
<222> LOCATION: (15)..(15)
<223> OTHER INFORMATION: Arg can be Lys

<400> SEQUENCE: 7

Asp Arg Pro Glu Gly Ile Glu Asn Asn Gly Gly Glu Arg Asp Arg
1               5                   10                  15

<210> SEQ ID NO 8
<211> LENGTH: 12
<212> TYPE: PRT
<213> ORGANISM: HIV

<400> SEQUENCE: 8

Val Glu Arg Tyr Leu Lys Asp Gln Gln Leu Leu Gly
1               5                   10

<210> SEQ ID NO 9
<211> LENGTH: 12
<212> TYPE: PRT
<213> ORGANISM: HIV

<400> SEQUENCE: 9
```

Val Glu Arg Tyr Leu Lys Asp Glu Glu Leu Leu Gly
1               5                   10

<210> SEQ ID NO 10
<211> LENGTH: 12
<212> TYPE: PRT
<213> ORGANISM: HIV

<400> SEQUENCE: 10

Val Glu Arg Tyr Leu Lys Asp Asn Asn Leu Leu Gly
1               5                   10

<210> SEQ ID NO 11
<211> LENGTH: 15
<212> TYPE: PRT
<213> ORGANISM: HIV

<400> SEQUENCE: 11

Gln Leu Leu Leu Asn Gly Ser Leu Ala Glu Glu Glu Ile Val Ile
1               5                   10                  15

<210> SEQ ID NO 12
<211> LENGTH: 15
<212> TYPE: PRT
<213> ORGANISM: HIV

<400> SEQUENCE: 12

Gln Leu Leu Leu Asn Gly Ser Leu Ala Glu Glu Val Val Ile
1               5                   10                  15

<210> SEQ ID NO 13
<211> LENGTH: 14
<212> TYPE: PRT
<213> ORGANISM: HIV

<400> SEQUENCE: 13

Gln Leu Leu Leu Asn Ser Leu Ala Glu Glu Glu Val Val Ile
1               5                   10

<210> SEQ ID NO 14
<211> LENGTH: 27
<212> TYPE: PRT
<213> ORGANISM: artificial sequence
<220> FEATURE:
<223> OTHER INFORMATION: Synthetic peptide

<400> SEQUENCE: 14

Ala Pro Thr Lys Ala Lys Arg Gly Gly Gly Ala Pro Thr Arg Ala Lys
1               5                   10                  15

Arg Gly Gly Gly Ala Pro Thr Glu Ala Lys Arg
                20                  25

<210> SEQ ID NO 15
<211> LENGTH: 26
<212> TYPE: PRT
<213> ORGANISM: artificial sequence
<220> FEATURE:
<223> OTHER INFORMATION: Synthetic peptide

<400> SEQUENCE: 15

Arg Val Val Glu Arg Glu Lys Gly Gly Gly Ala Lys Arg Arg Val Val
1               5                   10                  15

Gly Gly Gly Arg Val Val Gln Arg Glu Lys
                20                  25

<210> SEQ ID NO 16
<211> LENGTH: 24
<212> TYPE: PRT
<213> ORGANISM: artificial sequence
<220> FEATURE:
<223> OTHER INFORMATION: Synthetic peptide

<400> SEQUENCE: 16

Gly Gly Ala Lys Arg Arg Val Val Gly Gly Ala Lys Arg Arg Val Val
1               5                   10                  15

Gly Gln Arg Glu Lys Arg Ala Val
            20

<210> SEQ ID NO 17
<211> LENGTH: 25
<212> TYPE: PRT
<213> ORGANISM: artificial sequence
<220> FEATURE:
<223> OTHER INFORMATION: Synthetic peptide

<400> SEQUENCE: 17

Cys Gly Gly Ala Lys Arg Arg Val Val Gly Gly Ala Lys Arg Arg Val
1               5                   10                  15

Val Gly Gln Arg Glu Lys Arg Ala Val
            20                  25

<210> SEQ ID NO 18
<211> LENGTH: 23
<212> TYPE: PRT
<213> ORGANISM: artificial sequence
<220> FEATURE:
<223> OTHER INFORMATION: Synthetic peptide

<400> SEQUENCE: 18

Gly Gly Ala Lys Arg Arg Val Val Gly Gly Ala Lys Arg Arg Val Val
1               5                   10                  15

Gly Gly Gln Arg Glu Lys Arg
            20

<210> SEQ ID NO 19
<211> LENGTH: 24
<212> TYPE: PRT
<213> ORGANISM: artificial sequence
<220> FEATURE:
<223> OTHER INFORMATION: Synthetic peptide

<400> SEQUENCE: 19

Cys Gly Gly Ala Lys Arg Arg Val Val Gly Gly Ala Lys Arg Arg Val
1               5                   10                  15

Val Gly Gly Gln Arg Glu Lys Arg
            20

<210> SEQ ID NO 20
<211> LENGTH: 16
<212> TYPE: PRT
<213> ORGANISM: artificial sequence
<220> FEATURE:
<223> OTHER INFORMATION: Synthetic peptide

<400> SEQUENCE: 20

Gly Gly Ala Lys Arg Arg Val Val Gly Gly Ala Lys Arg Arg Val Val
1               5                   10                  15

```
<210> SEQ ID NO 21
<211> LENGTH: 17
<212> TYPE: PRT
<213> ORGANISM: artificial sequence
<220> FEATURE:
<223> OTHER INFORMATION: Synthetic peptide

<400> SEQUENCE: 21

Gly Cys Gly Ala Lys Arg Arg Val Val Gly Gly Ala Lys Arg Arg Val
1               5                   10                  15

Val

<210> SEQ ID NO 22
<211> LENGTH: 30
<212> TYPE: PRT
<213> ORGANISM: artificial sequence
<220> FEATURE:
<223> OTHER INFORMATION: Synthetic peptide

<400> SEQUENCE: 22

Gly Gly Gly Asp Gln Gln Leu Leu Gly Gly Ala Glu Glu Glu Ile Val
1               5                   10                  15

Gly Gly Ile Glu Glu Glu Gly Gly Glu Arg Asp Arg Asp Arg
            20                  25                  30

<210> SEQ ID NO 23
<211> LENGTH: 31
<212> TYPE: PRT
<213> ORGANISM: artificial sequence
<220> FEATURE:
<223> OTHER INFORMATION: Synthetic peptide

<400> SEQUENCE: 23

Cys Gly Gly Gly Asp Gln Gln Leu Leu Gly Gly Ala Glu Glu Glu Ile
1               5                   10                  15

Val Gly Gly Ile Glu Glu Glu Gly Gly Glu Arg Asp Arg Asp Arg
            20                  25                  30

<210> SEQ ID NO 24
<211> LENGTH: 22
<212> TYPE: PRT
<213> ORGANISM: artificial sequence
<220> FEATURE:
<223> OTHER INFORMATION: Synthetic peptide

<400> SEQUENCE: 24

Gly Gly Asp Gln Gln Leu Leu Gly Gly Ala Glu Glu Glu Ile Val Gly
1               5                   10                  15

Gly Gly Glu Arg Asp Arg
            20

<210> SEQ ID NO 25
<211> LENGTH: 25
<212> TYPE: PRT
<213> ORGANISM: artificial sequence
<220> FEATURE:
<223> OTHER INFORMATION: Synthetic peptide

<400> SEQUENCE: 25

Cys Gly Gly Gly Asp Gln Gln Leu Leu Gly Gly Ala Glu Glu Glu Ile
1               5                   10                  15

Val Gly Gly Ile Glu Glu Glu Gly Gly
            20                  25
```

-continued

```
<210> SEQ ID NO 26
<211> LENGTH: 15
<212> TYPE: PRT
<213> ORGANISM: artificial sequence
<220> FEATURE:
<223> OTHER INFORMATION: Synthetic peptide

<400> SEQUENCE: 26

Gly Gly Ala Glu Glu Val Val Gly Gly Asp Gln Gln Leu Leu
1               5                   10                  15

<210> SEQ ID NO 27
<211> LENGTH: 16
<212> TYPE: PRT
<213> ORGANISM: artificial sequence
<220> FEATURE:
<223> OTHER INFORMATION: Synthetic peptide

<400> SEQUENCE: 27

Cys Gly Gly Ala Glu Glu Glu Val Val Gly Gly Asp Gln Gln Leu Leu
1               5                   10                  15

<210> SEQ ID NO 28
<211> LENGTH: 25
<212> TYPE: PRT
<213> ORGANISM: artificial sequence
<220> FEATURE:
<223> OTHER INFORMATION: Synthetic peptide

<400> SEQUENCE: 28

Cys Gly Gly Ala Lys Arg Arg Val Val Gly Gly Ala Lys Arg Arg Val
1               5                   10                  15

Val Gly Gln Arg Glu Lys Arg Ala Val
            20                  25

<210> SEQ ID NO 29
<211> LENGTH: 31
<212> TYPE: PRT
<213> ORGANISM: artificial sequence
<220> FEATURE:
<223> OTHER INFORMATION: Synthetic peptide

<400> SEQUENCE: 29

Cys Gly Gly Gly Asp Gln Gln Leu Leu Gly Gly Ala Glu Glu Glu Ile
1               5                   10                  15

Val Gly Gly Ile Glu Glu Glu Gly Gly Glu Arg Asp Arg Asp Arg
            20                  25                  30

<210> SEQ ID NO 30
<211> LENGTH: 24
<212> TYPE: PRT
<213> ORGANISM: artificial sequence
<220> FEATURE:
<223> OTHER INFORMATION: Synthetic peptide

<400> SEQUENCE: 30

Cys Gly Gly Ala Lys Arg Arg Val Val Gly Gly Ala Lys Arg Arg Val
1               5                   10                  15

Val Gly Gly Gln Arg Glu Lys Arg
            20

<210> SEQ ID NO 31
<211> LENGTH: 25
<212> TYPE: PRT
<213> ORGANISM: artificial sequence
<220> FEATURE:
```

<223> OTHER INFORMATION: Synthetic peptide

<400> SEQUENCE: 31

Cys Gly Gly Gly Asp Gln Gln Leu Leu Gly Gly Ala Glu Glu Glu Ile
1               5                   10                  15

Val Gly Gly Ile Glu Glu Glu Gly Gly
            20                  25

<210> SEQ ID NO 32
<211> LENGTH: 16
<212> TYPE: PRT
<213> ORGANISM: artificial sequence
<220> FEATURE:
<223> OTHER INFORMATION: Synthetic peptide

<400> SEQUENCE: 32

Cys Gly Gly Ala Glu Glu Glu Val Val Gly Gly Asp Gln Gln Leu Leu
1               5                   10                  15

<210> SEQ ID NO 33
<211> LENGTH: 18
<212> TYPE: PRT
<213> ORGANISM: artificial sequence
<220> FEATURE:
<223> OTHER INFORMATION: Synthetic peptide

<400> SEQUENCE: 33

Gly Cys Gly Gly Ala Lys Arg Arg Val Val Gly Gly Ala Lys Arg Arg
1               5                   10                  15

Val Val

<210> SEQ ID NO 34
<211> LENGTH: 5
<212> TYPE: PRT
<213> ORGANISM: artificial sequence
<220> FEATURE:
<223> OTHER INFORMATION: Synthetic peptide

<400> SEQUENCE: 34

Asp Gln Gln Leu Leu
1               5

<210> SEQ ID NO 35
<211> LENGTH: 6
<212> TYPE: PRT
<213> ORGANISM: artificial sequence
<220> FEATURE:
<223> OTHER INFORMATION: Synthetic peptide

<400> SEQUENCE: 35

Ala Lys Arg Arg Val Val
1               5

<210> SEQ ID NO 36
<211> LENGTH: 6
<212> TYPE: PRT
<213> ORGANISM: artificial sequence
<220> FEATURE:
<223> OTHER INFORMATION: Synthetic peptide

<400> SEQUENCE: 36

Ala Glu Glu Glu Val Val
1               5

<210> SEQ ID NO 37

```
<211> LENGTH: 16
<212> TYPE: PRT
<213> ORGANISM: Artificial sequence
<220> FEATURE:
<223> OTHER INFORMATION: Synthetic peptide

<400> SEQUENCE: 37

Gly Gly Ala Ile Val Asn Gly Ser Leu Ala Asp Asp Asp Ile Val Ile
1               5                   10                  15

<210> SEQ ID NO 38
<211> LENGTH: 31
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: Cys may be linked to Lys in position 2 in SEQ
      ID NO: 39 or 40 or 42 or 43

<400> SEQUENCE: 38

Gly Ala Lys Arg Arg Val Val Gly Gly Cys Gly Gly Ala Lys Arg Arg
1               5                   10                  15

Val Val Gln Arg Glu Lys Arg Ala Gly Glu Arg Glu Lys Arg Ala
            20                  25                  30

<210> SEQ ID NO 39
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MUTAGEN
<222> LOCATION: (2)..(2)
<223> OTHER INFORMATION: Lys may be linked to Cys in position 10 in SEQ
      ID NO: 38 or 41

<400> SEQUENCE: 39

Gly Lys Gly Gly Ile Glu Glu Glu Gly Gly Arg Asp Arg Asp Arg Gly
1               5                   10                  15

Gly Glu Gln Asp Arg Asp Arg
            20

<210> SEQ ID NO 40
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Lys may be linked to Cys in position 10 in SEQ
      ID NO: 38 or 41

<400> SEQUENCE: 40

Gly Lys Gly Gly Ile Glu Glu Glu Gly Gly Glu Arg Asp Arg Asp Arg
1               5                   10                  15

Gly Gly Gln Asp Arg Asp Arg
            20

<210> SEQ ID NO 41
<211> LENGTH: 31
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: Cys may be linked to Lys in position 2 in SEQ
      ID NO: 39 or 40 or 42 or 43

<400> SEQUENCE: 41

Gly Ala Lys Arg Arg Val Val Gly Gly Cys Gly Gly Ala Lys Arg Arg
1               5                   10                  15

Val Val Glu Arg Glu Lys Arg Ala Gly Gln Arg Glu Lys Arg Ala
            20                  25                  30

<210> SEQ ID NO 42
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Lys may be linked to Cys in position 10 in SEQ
      ID NO: 38 or 41

<400> SEQUENCE: 42

Gly Lys Gly Gly Ile Glu Glu Glu Gly Gly Gln Asp Arg Asp Arg Gly
1               5                   10                  15

Gly Arg Asp Arg Asp Arg
            20

<210> SEQ ID NO 43
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Lys may be linked to Cys in position 10 in SEQ
      ID NO: 38 or 41

<400> SEQUENCE: 43

Gly Lys Gly Gly Ile Glu Glu Glu Gly Gly Glu Gln Asp Arg Asp Arg
1               5                   10                  15

Gly Gly Glu Arg Asp Arg Asp
            20

<210> SEQ ID NO 44
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Trp may be D-Trp
<220> FEATURE:
<221> NAME/KEY: DISULFID
<222> LOCATION: (4)..(10)
<220> FEATURE:
<221> NAME/KEY: MISC_FEATURE
<222> LOCATION: (24)..(24)
<223> OTHER INFORMATION: Carboxyterminal may be amidated

<400> SEQUENCE: 44
```

Trp Trp Gly Cys Ala Lys Arg Arg Val Cys Gly Gly Ala Lys Arg Arg
1               5                   10                  15

Val Val Gln Arg Glu Lys Arg Ala
            20

<210> SEQ ID NO 45
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Trp may be D-Trp
<220> FEATURE:
<221> NAME/KEY: DISULFID
<222> LOCATION: (4)..(10)
<220> FEATURE:
<221> NAME/KEY: MISC_FEATURE
<222> LOCATION: (22)..(22)
<223> OTHER INFORMATION: Carboxyterminus may be amidated

<400> SEQUENCE: 45

Trp Trp Gly Cys Ile Glu Glu Glu Gly Cys Gly Gly Ile Glu Glu Glu
1               5                   10                  15

Gly Gly Glu Arg Asp Arg
            20

<210> SEQ ID NO 46
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Glu can be Gly
<220> FEATURE:
<221> NAME/KEY: MISC_FEATURE
<222> LOCATION: (5)..(5)
<223> OTHER INFORMATION: Gly can be Arg
<220> FEATURE:
<221> NAME/KEY: MISC_FEATURE
<222> LOCATION: (13)..(13)
<223> OTHER INFORMATION: Arg can be Gln
<220> FEATURE:
<221> NAME/KEY: MISC_FEATURE
<222> LOCATION: (14)..(14)
<223> OTHER INFORMATION: Asp can be Gly
<220> FEATURE:
<221> NAME/KEY: MISC_FEATURE
<222> LOCATION: (15)..(15)
<223> OTHER INFORMATION: Arg can be Lys
<220> FEATURE:
<221> NAME/KEY: MISC_FEATURE
<222> LOCATION: (16)..(16)
<223> OTHER INFORMATION: Asp can be Gly

<400> SEQUENCE: 46

Asp Arg Pro Glu Gly Ile Glu Asn Asn Gly Gly Glu Arg Asp Arg Asp
1               5                   10                  15

Arg

<210> SEQ ID NO 47
<211> LENGTH: 20
<212> TYPE: PRT
<213> ORGANISM: Artificial Sequence
<220> FEATURE:
<223> OTHER INFORMATION: Synthetic peptide -continued

```
<220> FEATURE:
<221> NAME/KEY: MISC_FEATURE
<222> LOCATION: (1)..(1)
<223> OTHER INFORMATION: Xaa in position 1 is Lys or Arg
<220> FEATURE:
<221> NAME/KEY: MISC_FEATURE
<222> LOCATION: (2)..(2)
<223> OTHER INFORMATION: Xaa in position 2 is Ala, Gly, Ser or Arg
<220> FEATURE:
<221> NAME/KEY: MISC_FEATURE
<222> LOCATION: (3)..(3)
<223> OTHER INFORMATION: Xaa in position 3 is Leu or Met
<220> FEATURE:
<221> NAME/KEY: MISC_FEATURE
<222> LOCATION: (4)..(4)
<223> OTHER INFORMATION: Xaa in position 4 is Gly or Arg
<220> FEATURE:
<221> NAME/KEY: MISC_FEATURE
<222> LOCATION: (5)..(5)
<223> OTHER INFORMATION: Xaa in position 5 is Pro, Thr, Val, Ser, Gln or
      Ala
<220> FEATURE:
<221> NAME/KEY: MISC_FEATURE
<222> LOCATION: (6)..(6)
<223> OTHER INFORMATION: Xaa in position 6 is Gly, Ala, Lys, Arg, Gln or
      Glu
<220> FEATURE:
<221> NAME/KEY: MISC_FEATURE
<222> LOCATION: (8)..(8)
<223> OTHER INFORMATION: Xaa in position 8 is Thr or Ser
<220> FEATURE:
<221> NAME/KEY: MISC_FEATURE
<222> LOCATION: (9)..(9)
<223> OTHER INFORMATION: Xaa in position 9 is Leu or Ile
<220> FEATURE:
<221> NAME/KEY: MISC_FEATURE
<222> LOCATION: (14)..(14)
<223> OTHER INFORMATION: Xaa in position 14 is Thr, Ser or Val
<220> FEATURE:
<221> NAME/KEY: MISC_FEATURE
<222> LOCATION: (15)..(15)
<223> OTHER INFORMATION: Xaa in position 15 is Ala or Ser
<220> FEATURE:
<221> NAME/KEY: MISC_FEATURE
<222> LOCATION: (16)..(16)
<223> OTHER INFORMATION: Xaa in position 16 is Cys or Ser
<220> FEATURE:
<221> NAME/KEY: MISC_FEATURE
<222> LOCATION: (17)..(17)
<223> OTHER INFORMATION: Xaa in position 17 is Gln or Leu
<220> FEATURE:
<221> NAME/KEY: MISC_FEATURE
<222> LOCATION: (18)..(18)
<223> OTHER INFORMATION: Xaa in position 18 is Gly, Glu or Arg
<220> FEATURE:
<221> NAME/KEY: MISC_FEATURE
<222> LOCATION: (20)..(20)
<223> OTHER INFORMATION: Xaa in position 20 is Gly or Arg

<400> SEQUENCE: 47

Xaa Xaa Xaa Xaa Xaa Xaa Ala Xaa Xaa Gln Thr Pro Trp Xaa Xaa Xaa
1               5                   10                  15

Xaa Xaa Val Xaa
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic peptide

<400> SEQUENCE: 48

Lys Ala Leu Gly Pro Gly Ala Thr Leu Gln Thr Pro Trp Thr Ala Cys
1               5                   10                  15
```

Gln Gly Val Gly
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic peptide

<400> SEQUENCE: 49

Arg Ala Leu Gly Pro Ala Ala Thr Leu Gln Thr Pro Trp Thr Ala Ser
1               5                   10                  15

Leu Gly Val Gly
            20

<210> SEQ ID NO 50
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa in position 1 is Arg, Lys, Asp or none
<220> FEATURE:
<221> NAME/KEY: MISC_FEATURE
<222> LOCATION: (2)..(2)
<223> OTHER INFORMATION: Xaa in position 2 is Trp, Gly, Lys or Arg
<220> FEATURE:
<221> NAME/KEY: MISC_FEATURE
<222> LOCATION: (3)..(3)
<223> OTHER INFORMATION: Xaa in position 3 is Ile, Leu, Val or Met
<220> FEATURE:
<221> NAME/KEY: MISC_FEATURE
<222> LOCATION: (4)..(4)
<223> OTHER INFORMATION: Xaa in position 4 is Ile, Val or Leu
<220> FEATURE:
<221> NAME/KEY: MISC_FEATURE
<222> LOCATION: (5)..(5)
<223> OTHER INFORMATION: Xaa in position 5 Leu, Met, Val or Pro
<220> FEATURE:
<221> NAME/KEY: MISC_FEATURE
<222> LOCATION: (12)..(12)
<223> OTHER INFORMATION: Xaa in position 12 is  0, 1, 2 or 3 Gly
      residues
<220> FEATURE:
<221> NAME/KEY: MISC_FEATURE
<222> LOCATION: (13)..(13)
<223> OTHER INFORMATION: Xaa in position 13 is Arg or Lys
<220> FEATURE:
<221> NAME/KEY: MISC_FEATURE
<222> LOCATION: (14)..(14)
<223> OTHER INFORMATION: Xaa in position 14 is Met or Leu
<220> FEATURE:
<221> NAME/KEY: MISC_FEATURE
<222> LOCATION: (16)..(16)
<223> OTHER INFORMATION: Xaa in position 16 is Ser, Cys or Gln
<220> FEATURE:
<221> NAME/KEY: MISC_FEATURE
<222> LOCATION: (18)..(18)
<223> OTHER INFORMATION: Xaa in position 18 is Thr, Val, Ile, Ser or Ala
<220> FEATURE:
<221> NAME/KEY: MISC_FEATURE
<222> LOCATION: (19)..(19)
<223> OTHER INFORMATION: Xaa in position 19 is Ser, Gly or Thr
<220> FEATURE:
<221> NAME/KEY: MISC_FEATURE
<222> LOCATION: (22)..(22)
<223> OTHER INFORMATION: Xaa in position 22 is Asp, Glu, Cys or Gly
<220> FEATURE:
<221> NAME/KEY: MISC_FEATURE
<222> LOCATION: (23)..(23)

<223> OTHER INFORMATION: Xaa in position 22 is Gly or none

<400> SEQUENCE: 50

Xaa Xaa Xaa Xaa Xaa Gly Leu Asn Pro Leu Val Xaa Xaa Xaa Tyr Xaa
1               5                   10                  15

Pro Xaa Xaa Ile Leu Xaa Xaa
            20

<210> SEQ ID NO 51
<211> LENGTH: 24
<212> TYPE: PRT
<213> ORGANISM: Artificial Sequence
<220> FEATURE:
<223> OTHER INFORMATION: Synthetic peptide

<400> SEQUENCE: 51

Trp Ile Ile Pro Gly Leu Asn Pro Leu Val Gly Gly Gly Lys Leu Tyr
1               5                   10                  15

Ser Pro Thr Ser Ile Leu Cys Gly
            20

<210> SEQ ID NO 52
<211> LENGTH: 24
<212> TYPE: PRT
<213> ORGANISM: Artificial Sequence
<220> FEATURE:
<223> OTHER INFORMATION: Synthetic peptide

<400> SEQUENCE: 52

Arg Trp Leu Leu Leu Gly Leu Asn Pro Leu Val Gly Gly Gly Arg Leu
1               5                   10                  15

Tyr Ser Pro Thr Ser Ile Leu Gly
            20

<210> SEQ ID NO 53
<211> LENGTH: 23
<212> TYPE: PRT
<213> ORGANISM: Artificial Sequence
<220> FEATURE:
<223> OTHER INFORMATION: Synthetic peptide

<400> SEQUENCE: 53

Lys Ile Leu Leu Gly Leu Asn Pro Leu Val Gly Gly Gly Arg Leu Tyr
1               5                   10                  15

Ser Pro Thr Ser Ile Leu Gly
            20

<210> SEQ ID NO 54
<211> LENGTH: 23
<212> TYPE: PRT
<213> ORGANISM: Artificial Sequence
<220> FEATURE:
<223> OTHER INFORMATION: Synthetic peptide

<400> SEQUENCE: 54

Arg Leu Leu Leu Gly Leu Asn Pro Leu Val Gly Gly Gly Arg Leu Tyr
1               5                   10                  15

Ser Pro Thr Thr Ile Leu Gly
            20

<210> SEQ ID NO 55
<211> LENGTH: 25
<212> TYPE: PRT
<213> ORGANISM: Artificial Sequence

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa in position 1 is Asn, Ser, Gly, His, Ala,
      Pro, Arg or none
<220> FEATURE:
<221> NAME/KEY: MISC_FEATURE
<222> LOCATION: (2)..(2)
<223> OTHER INFORMATION: Xaa in position 2 is Asn, Ala or Lys
<220> FEATURE:
<221> NAME/KEY: MISC_FEATURE
<222> LOCATION: (3)..(3)
<223> OTHER INFORMATION: Xaa in position 3 is Pro, Gln, Gly, Ile or Leu
<220> FEATURE:
<221> NAME/KEY: MISC_FEATURE
<222> LOCATION: (7)..(7)
<223> OTHER INFORMATION: Xaa in position 7 is Val or Ala
<220> FEATURE:
<221> NAME/KEY: MISC_FEATURE
<222> LOCATION: (8)..(8)
<223> OTHER INFORMATION: Xaa in position 8 is Gly or Lys
<220> FEATURE:
<221> NAME/KEY: MISC_FEATURE
<222> LOCATION: (9)..(9)
<223> OTHER INFORMATION: Xaa in position 9 is Glu, Asp, Lys, Phe or Thr
<220> FEATURE:
<221> NAME/KEY: MISC_FEATURE
<222> LOCATION: (10)..(10)
<223> OTHER INFORMATION: Xaa in position 10 is Ile, Met, Val or Leu
<220> FEATURE:
<221> NAME/KEY: MISC_FEATURE
<222> LOCATION: (11)..(11)
<223> OTHER INFORMATION: Xaa in position 11 is Tyr, Leu or none
<220> FEATURE:
<221> NAME/KEY: MISC_FEATURE
<222> LOCATION: (12)..(12)
<223> OTHER INFORMATION: Xaa in position 12 is Ser or none
<220> FEATURE:
<221> NAME/KEY: MISC_FEATURE
<222> LOCATION: (13)..(13)
<223> OTHER INFORMATION: Xaa in position 13 is 1, 2 or 3 Gly residues
<220> FEATURE:
<221> NAME/KEY: MISC_FEATURE
<222> LOCATION: (14)..(14)
<223> OTHER INFORMATION: Xaa in position 14 is Arg or none
<220> FEATURE:
<221> NAME/KEY: MISC_FEATURE
<222> LOCATION: (15)..(15)
<223> OTHER INFORMATION: Xaa in position 15 is Asp, Arg, Trp, Ala or
      none
<220> FEATURE:
<221> NAME/KEY: MISC_FEATURE
<222> LOCATION: (16)..(16)
<223> OTHER INFORMATION: Xaa in position 16 is Ile or none
<220> FEATURE:
<221> NAME/KEY: MISC_FEATURE
<222> LOCATION: (17)..(17)
<223> OTHER INFORMATION: Xaa in position 17 is Tyr or none
<220> FEATURE:
<221> NAME/KEY: MISC_FEATURE
<222> LOCATION: (18)..(18)
<223> OTHER INFORMATION: Xaa in position 18 is Lys or Arg
<220> FEATURE:
<221> NAME/KEY: MISC_FEATURE
<222> LOCATION: (19)..(19)
<223> OTHER INFORMATION: Xaa in position 19 is Arg, Lys or Asp
<220> FEATURE:
<221> NAME/KEY: MISC_FEATURE
<222> LOCATION: (20)..(20)
<223> OTHER INFORMATION: Xaa in position 20 is Trp or Gly
<220> FEATURE:
<221> NAME/KEY: MISC_FEATURE
<222> LOCATION: (21)..(21)
<223> OTHER INFORMATION: Xaa in position 21 is Ile, Met, Val, Gln or Ala
<220> FEATURE:
<221> NAME/KEY: MISC_FEATURE
<222> LOCATION: (22)..(22)
```

```
<223> OTHER INFORMATION: Xaa in position 22 is Ile, Val or Ala
<220> FEATURE:
<221> NAME/KEY: MISC_FEATURE
<222> LOCATION: (23)..(23)
<223> OTHER INFORMATION: Xaa in position 23 is Leu, Met or Val
<220> FEATURE:
<221> NAME/KEY: MISC_FEATURE
<222> LOCATION: (24)..(24)
<223> OTHER INFORMATION: Xaa in position 24 is Gly or Cys
<220> FEATURE:
<221> NAME/KEY: MISC_FEATURE
<222> LOCATION: (25)..(25)
<223> OTHER INFORMATION: Xaa in position 25 is Leu or none

<400> SEQUENCE: 55

Xaa Xaa Xaa Pro Ile Pro Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 56
<211> LENGTH: 25
<212> TYPE: PRT
<213> ORGANISM: Artificial Sequence
<220> FEATURE:
<223> OTHER INFORMATION: Synthetic peptide

<400> SEQUENCE: 56

Arg Asn Ile Pro Ile Pro Val Gly Asp Ile Tyr Gly Gly Gly Asp Ile
1               5                   10                  15

Tyr Lys Arg Trp Gln Ala Leu Cys Leu
            20                  25

<210> SEQ ID NO 57
<211> LENGTH: 26
<212> TYPE: PRT
<213> ORGANISM: Artificial Sequence
<220> FEATURE:
<223> OTHER INFORMATION: Synthetic peptide

<400> SEQUENCE: 57

Arg Ala Ile Pro Ile Pro Ala Gly Thr Leu Leu Ser Gly Gly Gly Arg
1               5                   10                  15

Ala Ile Tyr Lys Arg Trp Ala Ile Leu Gly
            20                  25

<210> SEQ ID NO 58
<211> LENGTH: 23
<212> TYPE: PRT
<213> ORGANISM: Artificial Sequence
<220> FEATURE:
<223> OTHER INFORMATION: Synthetic peptide

<400> SEQUENCE: 58

Ala Leu Pro Ile Pro Ala Gly Phe Ile Tyr Gly Gly Gly Arg Ile Tyr
1               5                   10                  15

Lys Arg Trp Gln Ala Leu Gly
            20

<210> SEQ ID NO 59
<211> LENGTH: 22
<212> TYPE: PRT
<213> ORGANISM: Artificial Sequence
<220> FEATURE:
<223> OTHER INFORMATION: Synthetic peptide

<400> SEQUENCE: 59
```

```
Lys Ile Pro Ile Pro Val Gly Phe Ile Gly Gly Gly Trp Ile Tyr Lys
1               5                   10                  15

Arg Trp Ala Ile Leu Gly
            20

<210> SEQ ID NO 60
<211> LENGTH: 24
<212> TYPE: PRT
<213> ORGANISM: Artificial Sequence
<220> FEATURE:
<223> OTHER INFORMATION: Synthetic peptide

<400> SEQUENCE: 60

Lys Ile Pro Ile Pro Val Gly Thr Leu Leu Ser Gly Gly Gly Arg Ile
1               5                   10                  15

Tyr Lys Arg Trp Ala Ile Leu Gly
            20

<210> SEQ ID NO 61
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa in position 1 is Pro, Lys, Arg or none
<220> FEATURE:
<221> NAME/KEY: MISC_FEATURE
<222> LOCATION: (2)..(2)
<223> OTHER INFORMATION: Xaa in position 2 is Glu, Arg, Phe or Lys
<220> FEATURE:
<221> NAME/KEY: MISC_FEATURE
<222> LOCATION: (5)..(5)
<223> OTHER INFORMATION: Xaa in position 5 is Pro or Thr
<220> FEATURE:
<221> NAME/KEY: MISC_FEATURE
<222> LOCATION: (6)..(6)
<223> OTHER INFORMATION: Xaa in position 6 is Met, Thr or Nleu
<220> FEATURE:
<221> NAME/KEY: MISC_FEATURE
<222> LOCATION: (7)..(7)
<223> OTHER INFORMATION: Xaa in position 7 is Phe or Leu
<220> FEATURE:
<221> NAME/KEY: MISC_FEATURE
<222> LOCATION: (8)..(8)
<223> OTHER INFORMATION: Xaa in position 8 is Ser, Thr, Ala or Met
<220> FEATURE:
<221> NAME/KEY: MISC_FEATURE
<222> LOCATION: (9)..(9)
<223> OTHER INFORMATION: Xaa in position 9 is Ala, Glu or Leu
<220> FEATURE:
<221> NAME/KEY: MISC_FEATURE
<222> LOCATION: (11)..(11)
<223> OTHER INFORMATION: Xaa in position 11 is Ser or none
<220> FEATURE:
<221> NAME/KEY: MISC_FEATURE
<222> LOCATION: (12)..(12)
<223> OTHER INFORMATION: Xaa in position 12 is 1, 2 or 3 Gly residues
<220> FEATURE:
<221> NAME/KEY: MISC_FEATURE
<222> LOCATION: (13)..(13)
<223> OTHER INFORMATION: Xaa in position 12 is 0, 1, 2 or 3 Arg residues
<220> FEATURE:
<221> NAME/KEY: MISC_FEATURE
<222> LOCATION: (14)..(14)
<223> OTHER INFORMATION: Xaa in position 14 is Ala, Arg or none
<220> FEATURE:
<221> NAME/KEY: MISC_FEATURE
<222> LOCATION: (15)..(15)
<223> OTHER INFORMATION: Xaa in position 15 is Ile, Leu or none
<220> FEATURE:
```

```
<221> NAME/KEY: MISC_FEATURE
<222> LOCATION: (16)..(16)
<223> OTHER INFORMATION: Xaa in position 16 is Ser, Ala, Leu or none
<220> FEATURE:
<221> NAME/KEY: MISC_FEATURE
<222> LOCATION: (17)..(17)
<223> OTHER INFORMATION: Xaa in position 17 is Tyr, Glu or Asp
<220> FEATURE:
<221> NAME/KEY: MISC_FEATURE
<222> LOCATION: (18)..(18)
<223> OTHER INFORMATION: Xaa in position 18 is Gly or Asp
<220> FEATURE:
<221> NAME/KEY: MISC_FEATURE
<222> LOCATION: (19)..(19)
<223> OTHER INFORMATION: Xaa in position 19 is Ala or Leu
<220> FEATURE:
<221> NAME/KEY: MISC_FEATURE
<222> LOCATION: (20)..(20)
<223> OTHER INFORMATION: Xaa in position 20 is Thr, Ile, Val, Leu or Asn
<220> FEATURE:
<221> NAME/KEY: MISC_FEATURE
<222> LOCATION: (21)..(21)
<223> OTHER INFORMATION: Xaa in position 21 is Pro, Thr or Ser
<220> FEATURE:
<221> NAME/KEY: MISC_FEATURE
<222> LOCATION: (22)..(22)
<223> OTHER INFORMATION: Xaa in position 22 is Tyr, Phe, Nleu, His or
     Gln
<220> FEATURE:
<221> NAME/KEY: MISC_FEATURE
<222> LOCATION: (23)..(23)
<223> OTHER INFORMATION: Xaa in position 23 is Asp, Asn, Leu or Ala
<220> FEATURE:
<221> NAME/KEY: MISC_FEATURE
<222> LOCATION: (24)..(24)
<223> OTHER INFORMATION: Xaa in position 24 is Leu, Ile, Val or Asn
<220> FEATURE:
<221> NAME/KEY: MISC_FEATURE
<222> LOCATION: (25)..(25)
<223> OTHER INFORMATION: Xaa in position 25 is Asn, Tyr, Cys or Gly
<220> FEATURE:
<221> NAME/KEY: MISC_FEATURE
<222> LOCATION: (26)..(26)
<223> OTHER INFORMATION: Xaa in position 26 is Thr, Met, Ile, Ala, Val
     or none
<220> FEATURE:
<221> NAME/KEY: MISC_FEATURE
<222> LOCATION: (27)..(27)
<223> OTHER INFORMATION: Xaa in postion 27 is Gly or none

<400> SEQUENCE: 61

Xaa Xaa Ile Ile Xaa Xaa Xaa Xaa Xaa Leu Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 62
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa in position 6 is Norleucine
<220> FEATURE:
<221> NAME/KEY: MISC_FEATURE
<222> LOCATION: (21)..(21)
<223> OTHER INFORMATION: Xaa in position 21 is Norleucine

<400> SEQUENCE: 62

Lys Phe Ile Ile Pro Xaa Phe Ser Ala Leu Gly Gly Ala Ile Ser Tyr
1               5                   10                  15
```

Asp Leu Asn Thr Xaa Leu Asn Cys Ile
            20                  25

<210> SEQ ID NO 63
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa in position 6 is Norleucine

<400> SEQUENCE: 63

Lys Phe Ile Ile Pro Xaa Phe Ser Ala Leu Ser Gly Gly Gly Ala Ile
1               5                   10                  15

Ser Tyr Asp Leu Asn Thr Phe Leu Asn Cys Ile Gly
            20                  25

<210> SEQ ID NO 64
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa in position 6 is Norleucine

<400> SEQUENCE: 64

Arg Phe Ile Ile Pro Xaa Phe Thr Ala Leu Ser Gly Gly Arg Arg Ala
1               5                   10                  15

Leu Leu Tyr Gly Ala Thr Pro Tyr Ala Ile Gly
            20                  25

<210> SEQ ID NO 65
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa in position 5 is Norleucine

<400> SEQUENCE: 65

Lys Ile Ile Pro Xaa Phe Ser Ala Leu Gly Gly Gly Arg Leu Leu Tyr
1               5                   10                  15

Gly Ala Thr Pro Tyr Ala Ile Gly
            20

<210> SEQ ID NO 66
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa in position 5 is Norleucine

<400> SEQUENCE: 66

Arg Ile Ile Pro Xaa Phe Thr Ala Leu Ser Gly Gly Gly Arg Leu Leu
1               5                   10                  15

```
<210> SEQ ID NO 67

<400> SEQUENCE: 67

000

<210> SEQ ID NO 68
<211> LENGTH: 22
<212> TYPE: PRT
<213> ORGANISM: Artificial Sequence
<220> FEATURE:
<223> OTHER INFORMATION: Synthetic peptide

<400> SEQUENCE: 68

Gly Lys Gly Gly Ile Glu Glu Glu Gly Gly Arg Asp Arg Asp Arg Gly
1               5                   10                  15

Gly Gln Asp Arg Asp Arg
            20

<210> SEQ ID NO 69

<400> SEQUENCE: 69

000

<210> SEQ ID NO 70
<211> LENGTH: 24
<212> TYPE: PRT
<213> ORGANISM: Artificial Sequence
<220> FEATURE:
<223> OTHER INFORMATION: Synthetic peptide

<400> SEQUENCE: 70

Asn Ile Pro Ile Pro Val Gly Asp Ile Tyr Gly Gly Gly Asp Ile Tyr
1               5                   10                  15

Lys Arg Trp Gln Ala Leu Cys Leu
            20

<210> SEQ ID NO 71
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa in position 5 is Norleucine
<220> FEATURE:
<221> NAME/KEY: MISC_FEATURE
<222> LOCATION: (20)..(20)
<223> OTHER INFORMATION: Xaa in position 20 is Norleucine

<400> SEQUENCE: 71

Trp Ile Ile Pro Xaa Phe Ser Ala Leu Gly Gly Ala Ile Ser Tyr Asp
1               5                   10                  15

Leu Asn Thr Xaa Leu Asn Cys Ile
            20
```